US006492531B1

(12) United States Patent
Woodruff

(10) Patent No.: US 6,492,531 B1
(45) Date of Patent: Dec. 10, 2002

(54) METHOD OF TREATING COGNITIVE DISORDERS

(75) Inventor: Geoffrey Neil Woodruff, Herts (GB)

(73) Assignee: Warner-Lambert Company, Morris Plains, NJ (US)

(*) Notice: Subject to any disclaimer, the term of this patent is extended or adjusted under 35 U.S.C. 154(b) by 0 days.

(21) Appl. No.: 08/372,727

(22) Filed: Jan. 17, 1995

Related U.S. Application Data

(63) Continuation of application No. 08/149,168, filed on Nov. 8, 1993, now abandoned, which is a continuation of application No. 07/837,186, filed on Feb. 18, 1992, now abandoned.

(51) Int. Cl.$^7$ ............................................. C07D 209/20
(52) U.S. Cl. ...................... 548/496; 514/19; 562/445; 568/818; 548/496
(58) Field of Search ................ 514/18, 19; 562/445; 568/818; 548/496

(56) References Cited

U.S. PATENT DOCUMENTS 5,278,316 A * 1/1994 Horwell ...................... 548/496

FOREIGN PATENT DOCUMENTS

EP 0405537 1/1991 .................. 209/20

OTHER PUBLICATIONS

Ann. Rev. Pharmacol. Toxicol., 31:469–501 (1991), G. Woodruff et al., "Cholecystokinin Antagonists".

Proc. Natl. Acad. Sci., 87:6728–6732 (1990), J. Hughes et al., "Development of a Class of Selective Cholecystokinin . . ." ibid., 88:1130–1133 (1991), L. Singh et al., "Evidence for an involvement of the brain cholecystokinin . . . ".

Montgomery, K.C., *J Comp Physiol Psych*, 1952, 43:3, "A Test of Two Explanations of Spontaneous Alternation."

* cited by examiner

*Primary Examiner*—Christopher S. F. Low
*Assistant Examiner*—David Lukton
(74) *Attorney, Agent, or Firm*—Elizabeth M. Anderson; Charles Ashbrook

(57) ABSTRACT

The invention concerns cholecystokinin (CCK) antagonists useful in the treatment of cognitive disorders. Especially useful are $CCK_B$ antagonists such as CI-988.

4 Claims, 5 Drawing Sheets

METHOD OF TREATING COGNITIVE DISORDERS

This application is a continuation of application Ser. No. 08/149,68, filed Nov. 8, 1993, now abandoned, which is a continuation of application Ser. No. 07/837186, filed Feb. 18, 1992, now abandoned.

BACKGROUND OF THE INVENTION

Cholecystokinin (CCK) is a neuropeptide with a widespread distribution in brain. CCK receptors are classified into two types; $CCK_A$ and $CCK_B$, both of which are present in brain (Woodruff, G. N. and Hughes, J., 1991, *Ann. Rev. Pharmacol.* 31, 469–501).

CI-988, the chemical name is: [R-(R*,R*)]-4-[[2-[[3-(1H-indol-3-yl)-2-methyl-1-oxo-2-[[[(tricyclo[3.3.1.1$^{3,7}$]dec-2-yloxy)carbonyl]amino]propyl]amino]-1-phenylethyl]amino)-4-oxobutanoic acid, and the structure is:

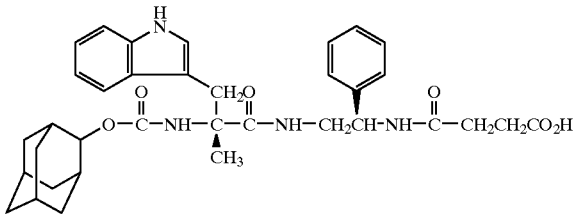

It is a potent $CCK_B$ antagonist with high selectivity for $CCK_B$ receptors (Hughes, J., et al, 1990, *Proc. Natl. Acad. Sci.,* USA, 87 6728–6732). $CCK_B$ antagonists have been shown to have anxiolytic-like activity in animal models of anxiety (Hughes, J., et al, *Proc. Natl. Acad. Sci.,* USA, 87, 6728–6732; Singl, L., Lewis, A. S., Field, M. J., Hughes, J., and Woodruff, G. N., 1991, *Proc. Natl. Acad. Sci.,* USA, 88, 1130–1133), suggesting a physiological role for CCK in anxiety. It has also been suggested that CCK may be involved in the control of food intake and in analgesic responses (Woodruff, G. N. and Hughes, J., 1991, *Ann. Rev. Pharmacol.* 31, 469–501).

The above compound and other CCK antagonists have been described in EPA 0405537. These antagonists are also described in U.S. application Ser. No. 07/629,809, filed Dec. 19, 1990, now U.S. Pat. No. 5,278,316 the disclosure of which is hereby incorporated by reference.

Other CCK antagonists have been described in U.S. application Ser. No. 07/726,656, now U.S. Pat. No. 5,331,006; Ser. No. 07/726,655, now abandoned; application Ser. Nos. 07/839,647; 07/726,654 now U.S. Pat. Nos. 5,244,915, 5,397,788, and 5,523,306; Ser. No. 07/726,653 now U.S. Pat. No. 5,340,825; Ser. No. 07/726,652 now U.S. Pat. No. 5,264,419; and, Ser. No. 07/726,651 now U.S. Pat. No. 5,244,905, the disclosures of which are also hereby incorporated by reference.

The above patents and applications cover the compounds of the instant invention, methods for preparing them, and several uses thereof.

The above references do not disclose the use of $CCK_B$ antagonists for treating cognitive disorders.

The present invention concerns medical methods of treatment. More particularly, the invention concerns the use of CCK-B ligands for the treatment of the symptoms of cognitive decline or deficiencies such as in the loss of memory or in an elderly patient suffering from Alzhemier's disease.

Disorders of cognition are generally characterized by symptoms of forgetfulness, confusion, memory loss, attentional deficits and/or, in some cases, affective disturbances. These symptoms may arise as a result of the general aging process and/or from organic brain disease, cerebrovascular disease, head injury or developmental or genetic defects.

The general decrease in cognitive function which accompanies the aging process is well known. The same phenomenon has been observed and documented in many lower mammals, including those routinely employed in pharmacological testing programs for screening and predicting usefulness for particular drugs in higher animals, including humans.

Although disorders of cognition often accompany the general aging process, presenile and senile primary degenerative dementia are the most common accepted causes of mental deterioration in the elderly. It has been estimated that at least ten percent of persons over sixty years of age will eventually suffer severe mental deterioration. A much larger number will experience cognitive decline of sufficient severity to impede their activities.

SUMMARY OF THE INVENTION AND DETAILED DESCRIPTION

The present invention relates to a novel therapeutic use of known compounds, $CCK_B$ antagonists, their derivatives, and pharmaceutically acceptable salts. The present invention concerns a method for treating cognitive disorders in a mammal in need of such treatment.

This invention provides a method of treating disorders of cognition using $CCK_B$ receptor antagonists. The results presented herein indicate that such compounds improve basal cognition and inhibit the impairments in performance caused by cholinergic deficits. Thus the compounds with CCK-B receptor antagonist activity are expected to be useful in diseases such as senile cognitive decline, Alzheimer's disease, myasthenia gravis, tardive dyskinesia and dementia associated with Down's syndrome or Parkinson's disease.

The treatment comprises administering in unit dosage form an amount effective to treat the cognitive disorder of a $CCK_B$ antagonist or a pharmaceutically acceptable salt thereof to a mammal in need of such treatment.

Preferred compounds include but are not limited to:

1. [1S-[1α,2β[S*[S*(E)]],4α]]-4-[[2-[[3-(1H-indol-3-yl)-2-methyl-1-oxo-2-[[[(1,7,7-trimethylbicyclo[2.2.1]hept-2-yl)oxy]carbonyl]amino]propyl]amino]-1-phenylethyl]amino]-4-oxo-2-butenoic acid,
2. [1S-[1α,2β[S*(S*)],4α]]-4-[[2-[[3-(1H-indol-3-yl)-2-methyl-1-oxo-2-[[[(1,7,7-trimethylbicyclo-[2.2.1]hept-2-yl)oxy]carbonyl]amino]propyl]methylamino]-1-phenylethyl]amino]-4-oxobutanoic acid,
3. [1S-[1α,2β[S*(S*)],4α]]-4-[[2-[[3-(1H-indol-3-yl-2-methyl-1-oxo-2-[[[(1,7,7-trimethylbicyclo[2.2.1]-hept-2-yl)amino]carbonyl]amino]propyl]amino]-1-phenylethyl]amino]-4-oxobutanoic acid,
4. [R-(R*,R*)]-4-[[2-[[3-(1H-indol-3-yl)-2-methyl-1-oxo-2-[(tricyclo[3.3.1.1$^{3,7}$]dec-2-ylsulfonyl)amino]propyl]amino]-1-phenylethyl]amino]-4-oxobutanoic acid,
5. [R-(R*,S*)]-4-[[2-[[3-(1H-indol-3-yl)-2-methyl-1-oxo-2-[(tricyclo[3.3.1.1$^{3,7}$]dec-2-ylsulfonyl)amino]propyl]amino]-3-phenylpropyl]amino]-4-oxobutanoic acid,
6. [1R-[1α[R*(S*)],2β]] and [1S-[1α[S*(R*)],2β]]-4-[[2-[[2-[[[(2-fluorocyclohexyl)oxy]carbonyl]amino]-3-(1H-indol-3-yl)-2-methyl-1-oxopropyl]amino]-3-phenylpropyl]amino]-4-oxobutanoic acid,
7. [1R-(1α[R*(S*)],2β]] and [1S-[1α[S*(R*)],2β]]-4-[[2-[[2-[[[(2-fluorocyclohexyl)oxy]carbonyl]amino]-3-(1H- indol-3-yl)-2-methyl-1-oxopropyl]methylamino]-3-phenylpropyl]amino]-4-oxobutanoic acid, 8. [1R-[1α[R*(S*)],2β]] and [1S-[1α[S*(R*)],2β]-4-[[2-[[3-(1H-indol-3-yl)-2-methyl-1-oxo-2-[[[[2-(trifluoromethyl)cyclohexyl]oxy]carbonyl]amino]propyl]amino]-3-phenylpropyl]amino]-4-oxobutanoic acid, 9. [1R-[1α[R*(S*)],2β]] and [1S-[1α[S*(R*)],2β]-4-[[2-[[3-(1H-indol-3-yl)-2-methyl-1-oxo-2-[[[[2-(trifluoromethyl)cyclohexyl]oxy]carbonyl]amino]propyl]methylamino]-3-phenylpropyl]amino]-4-oxobutanoic acid, 10. [R-(R*,S*)]-4-[[2-[[3-(1H-indol-3-yl)-2-methyl-1-oxo-2-[[(tricyclo[3.3.1.1$^{3,7}$]dec-2-yloxy)carbonyl]amino]propyl]methylamino]-3-phenylpropyl]amino]-4-oxobutanoic acid, 11. [1S-[1α,2β[S*(R*)],4α]]-[1-(1H-indol-3-ylmethyl)-1-methyl-2-oxo-2-[[2-[[1-oxo-3-(1H-tetrazol-5-yl)propyl]amino]-1-(phenylmethyl)ethyl]amino]ethyl]carbamic acid, 1,7,7-trimethylbicyclo[2.2.1]hept-2-yl ester, 12. [1S-[1α,2β[S*,R*)]-[1-(1H-indol-3-ylmethyl)-1-methyl-2-oxo-2-[[2-[[1-oxo-3-(1H-tetrazol-5-yl)propyl]amino]-2-phenylethyl]amino]ethyl]carbamic acid, 1,7,7-trimethylbicyclo[2.2.1]hept-2-yl ester, 13. N-[2-methyl-N-[(tricyclo[3.3.1.1$^{3,7}$]dec-2-yloxy)carbonyl]-D-tryptophyl]-L-phenylalanylglycine, 14. N-[2-methyl-N-[(tricyclo[3.3.1.1$^{3,7}$]dec-2-yloxy)carbonyl]-D-tryptophyl]-L-phenylalanyl-β-alanine, and 15. (R)-tricyclo[3.3.1.1$^{3,7}$]dec-2-yl [1-(1H-indol-3-ylmethyl)-1-methyl-2-[methyl(2-phenylethyl)amino]-2-oxo-ethylcarbamate.

In addition preferred compounds of the instant invention are:

16. (±)-trans-2-chlorocyclohexyl [1-(1H-indol-3-ylmethyl)-1-methyl-2-oxo-2-[(2-phenylethyl)amino]ethyl]carbamate, 17. 2-chorocyclohexyl [2-[[1-(hydroxymethyl)-2-phenylethyl]amino]-1-(1H-indol-3-ylmethyl)-1-methyl-2-oxoethyl]carbamate, 18. 2-[[2-[[[(2-chlorocyclohexyl)oxy]carbonyl]amino]-3-(1H-indol-3-yl)-2-methyl-1-oxopropyl)amino]-3-phenylpropyl butanedioate, 19. 2-[[2-[[[(2-methylcyclohexyl)oxy]carbonyl]amino]3-(1H-indol-3-yl)-2-methyl-1-oxopropyl]amino]-3-phenylpropyl butanedioate, 20. (±)-tricyclo[3.3.1.1$^{3,7}$]dec-2-yl[1-(1H-indol-3-ylmethyl)-1-methyl-2-oxo-2-[(2-phenylethyl)amino]ethyl]carbamate, 21. tricyclo[3.3.1.1$^{3,7}$]dec-2-yl[2-[[1-(hydroxymethyl)-2-phenylethyl]amino]-1-(1H-indol-3-ylmethyl)-1-methyl-2-oxoethyl]carbamate, 22. 2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl butanedioate, 23. 2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl butanedioate, 24. [R-(R*,R*)]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxobutanoic acid, 25. [1S-[[1α,2β[S*(S*)],4α]]-4-[[2-[3-(1H-indol-3-yl)-2-methyl-1-oxo-2-[[[(1,7,7-trimethylbicyclo-2.2.1]hept-2-yloxy)carbonyl]amino]propyl]amino]-1-phenylethyl]amino]-4-oxobutanoic acid, 26. [R-[R*,S*-(E)]]-4-[[2-[[3-(1H-indol-3-yl)-2-methyl-1-oxo-2-[[(tricyclo[3.3.1.1$^{3,7}$]dec-2-yloxy)carbonyl) amino]propyl]amino]-3-phenylpropyl]amino]-4-oxo-2-butenoic acid, 27. [R-(R*,S*)]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-4-oxobutanoic acid, 28. (R)-tricyclo[3.3.1.1$^{3,7}$]dec-2-yl [1-(1H-indol-3-ylmethyl)-1-methyl-2-[methyl(2-phenylethyl)amino]-2-oxoethylcarbamate, 29. [R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]sulfinyl]acetic acid, ethyl ester, 30. [R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]sulfonyl]acetic acid, ethyl ester, 31. [R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]sulfinyl]acetic acid, 32. [R-[R*,R*-(E)]]-4-[[2-[[3-(1H-indol-3-yl)-2-methyl-1-oxo-2-[[(tricyclo[3.3.1.1$^{3,7}$]dec-2-yloxy)]carbonyl]amino]propyl]amino]-1-phenylethyl]amino]-4-oxo-2-butenoic acid, 33. [R-(R*,S*)]-[[2-[2-[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]thio]acetic acid, 34. [1S-[1α,2β[S*[S*(E)]],4α]]-4-[[2-[[3-(1H-indol-3-yl)-2-methyl-1-oxo-2-[[[(1,7,7-trimethylbicyclo[2.2.1]hept-2 acid, methyl ester, (Bicyclo system is 1S-endo), 35. [1S-[1α,2β[S*[S*(E)]],4α]]-4-[[2-[[3-(1H-indol-3-yl)-2-methyl-1-oxo-2-[[[(1,7,7-trimethylbicyclo-[2.2.1]hept- acid, (Bicyclo system is 1S-endo), 36. [R-(R*,R*)]-3-[[2-[[3-(1H-indol-3-yl)-2-methyl-1-oxo-3-[[(tricyclo[3.3.1.1$^{3,7}$]dec-2-yloxy)]carbonyl]amino]propyl]amino)-1-phenylethyl]amino]-3-oxopropanoic acid, 37. [R-(R*,S*))-3-(1H-indol-3-ylmethyl)-3-methyl-4,10-dioxo-6-(phenylmethyl)-11-oxo-8-thia-2,5-diazatridecanoic acid, tricyclo[3.3.1.1$^{3,7}$]dec-2-yl or ester, 38. [R-(R*,S*)]-β-[[3-(1H-indol-3-yl)-2-methyl-1-oxo-2-[[(tricyclo[3.3.1.1$^{3,7}$]dec-2-yloxy)]carbonyl]amino]propyl]amino]benzenebutanoic acid, 39. [R-(R*,S*))-N-[3-[[3-(1H-indol-3-yl)-2-methyl-1-oxo-2-[[(tricyclo[3.3.1.1$^{3,7}$]dec-2-yloxy)]carbonyl]amino]propyl]amino]-4-phenylbutyl]glycine, 40. (R-[R*,S*-(E)]]-4-[[2-[[3-(1H-indol-3-yl)-2-methyl-2-[[(bicyclo[3.3.1]non-9-yloxy)carbonyl]amino acid, 41. mono[R-(R*,R*)]-2-[[3-(1H-indol-3-yl)-2-methyl-1-oxo-2-[[(tricyclo[3.3.1.1$^{3,7}$]dec-2-yloxy)carbonyl]butanedioate, 42. 3-[[3-[[3-(1H-indol-3-yl)-2-methyl-1-oxo-2-[[(tricyclo[3.3.1.1$^{3,7}$]dec-2-yloxy)carbonyl]amino]propyl]amino]-1-oxo-2-phenylprophl]amino]propanoic acid (TRP is R, other center is RS), 43. [1R-[1α(R*(S*)],2β]]-4-[[2-[[3-(1H-indol-3-yl)-2-methyl-2-[[[(2-methyl-1-cyclohexyl)oxy]carbonyl]amino]propyl]amino]-1-phenylethyl acid, (-)-Isomer, 44. [1R-[1α[R*(S*)],2β]]-4-[[2-[[3-(1H-indol-3-yl)-2-methyl-2-[[[(2-methyl-1-cyclohexyl)oxy]carbonyl]amino]propyl]amino]-1-phenylethyl]amino]-4-oxobutanoic acid, (Same), 45. [1R-[1α[R*(S*)],2β]]-4-[[2-[[3-(1H-indol-3-yl)-2-methyl-2-[[[(2-methyl-1-cyclohexyl)oxy]carbonyl]amino]propyl]amino]-1-phenylethyl]amino]-4

46. [1R-[1α[R*(S*)],2β]]-4-[[2-[[3-(1H-indol-3-yl)-2-methyl-2-[[[(2-methyl-1-cyclohexyl)oxy]carbonyl]amino acid, (-)-Isomer, 47. 2-methylcyclohexyl-[1R-[1α[R*(S*)]],2β]-[2-[[1-(hydroxymethyl)-2-phenylethyl]amino]-1-(1H-indol-3-ylmethyl)-1-methyl-2-oxoethyl]carbamate, 48. [R-[R*,S*-(E,E)]]-6-[[3-(1H-indol-3-yl)-2-methyl-1-oxo-2-[[(tricyclo[3.3.1.1$^{3,7}$]dec-2-yloxy)carbonyl]amino]propyl]amino]-7-phenyl-2,4-heptadienoic acid, 49. [R-(R*,R*)]-[2-[[2-[[1,4-dioxo-4-(1H-tetrazol-5-ylamino)butyl]amino]-2-phenylethyl]amino]-1-(1H-indol-3-ylmethyl)-1-methyl-2-oxoethyl]carbamic acid,
50. tricyclo[3.3.1.1$^{3,7}$]dec-2-yl-[S-[R*,S*-(E)]]-12-(1H-indol-3-ylmethyl)-12-methyl-3,11-dioxo-9-(phenylmethyl)-2-oxa-7,10,13-triazatetradec-4-en-14-oate,
51. [R-(R*,S*)]-3-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-3-oxopropanoic acid,
52. ethyl [R-(R*,S*)]-[[2-[[2-[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]thio]acetate,
53. [R-(R*,S*)]-β-[[3-(1H-indol-3-yl) -2-methyl-1-oxo-2-[[tricyclo[3.3.1.1$^{3,7}$]dec-2-yloxy)carbonyl]amino]propyl]amino]-4-iodo-benzenebutanoic acid,
54. [R-(R*,R*)]-[2-[[3-(1H-indol-3-yl)-2-methyl-1-oxo-2-[[(1(tricyclo[[(3.3.1.1$^{3,7}$]dec-2-yloxy)carbonyl]amino]propyl]amino]-1-phenylethoxy]acetic acid,
55. [[3-[[3-(1H-indol-3-yl)-2-methyl-1-oxo-3-[[tricyclo(3.3.1.1$^{3,7}$]dec-2-yloxy)carbonyl]amino]propyl]amino]-1-oxo-2-phenylpropyl]amino]acetic acid (TRP center is R, other center is RS),
56. (R)-[[[2-[[3-(1H-indol-3-yl)-1-oxo-2-methyl-2-[[(tricyclo[3.3.1.1$^{3,7}$]dec-2-yloxy)carbonyl]amino]propyl]amino]-1-phenylethylidene]amino]oxy]acetic acid,
57. [R-(R*,S*)]-β-[[3-(1H-indol-3-yl)-2-methyl-1-oxo-2-[[(tricyclo[3.3.1.1$^{3,7}$]dec-2-yloxy)carbonyl]amino]propyl]amino]benzenebutanoic acid,
58. [R-(R*,S*)]-N-[3-[[3-(1H-indol-3-yl)-2-methyl-1-oxo-2-[[(tricyclo[3.3.1.1$^{3,7}$]dec-2-yloxy)carbonyl]propyl]amino]-4-phenylbutyl]glycine,
59. 2-[[[2-[[3-(1H-indol-3-yl)-2-methyl-1-oxo-2-[[(tricyclo[3.3.1.1$^{3,7}$]dec-2-yloxy)carbonyl]amino]propyl]amino)-1-phenylethyl]amino]carbonyl]cyclopropanecarboxylic acid (cyclopropane ring is trans-(±), other centers are R),
60. carbamic acid, [1-(1H-indol-3-ylmethyl)-1-methyl-2-oxo-2-[[2-[[1-oxo-3-(1H-tetrazol-5-yl)propyl]amino]-2-phenylethyl]amino]ethyl-, tricyclo[3.3.1.1$^{3,7}$]dec-2-yl ester, [R,(R*,S*)]-,
61. benzeneheptanoic acid, α-[[3-(1H-indol-3-yl)-2-methyl-1-oxo-2-[[(tricyclo[3.3.1.1$^{3,7}$]dec-2-yloxy)carbonyl]amino]propyl]amino]-,[R-(R*,S*)]-,
62. methyl-(±)-β-[[(2-phenylethyl)amino]carbonyl]-1β-[[(tricyclo[3.3.1.1$^{3,7}$]dec-2-yloxy)carbonyl]amino]-1H-indole-3-butanoate,
63. [R-(R*,S*)]-4-[[2-(1H-indol-3-yl)-2-methyl-1-oxo-2-[[tricyclo[3.3.1.1$^{3,7}$]dec-2-yloxycarbonyl]amino]propyl]amino]-3-phenylpropyl]amino]-4-oxo-2-butenoic acid,
64. bicyclo[2.2.1]heptane-2-acetic acid, 3-[[[[2-[[1-(hydroxymethyl)-2-phenylethyl]amino]-1-(1H-indol-3-ylmethyl)-1-methyl-2-oxoethyl]amino]carbonyl]oxy]-4,7,7-trimethyl-, [1R-[1α,2β,3α[R*(S*)],4α]]-,
65. butanoic acid, 4-[[2-[[3-(1H-indol-3-yl)-2-methyl-2-[[[(2-methyl-1-cyclohexyl)oxy]carbonyl]amino]-1-oxopropyl]amino)-1-phenylethyl]amino]-4-oxo-[1R-1α[R*(R*)]2β]]-((–)-isomer),
66. 2-butenoic acid, 4-[[2-[[3-(1H-indol-3-yl)-2-methyl-2-[[[(2-methyl-1-cyclohexyl)oxy]carbonyl]amino]-1-oxopropyl]amino]-1-phenylethyl]amino]-4-oxo-, [1R-[1α[R*(R*))],2β]]-((–) -isomer),
67. butanoic acid, 4-[[2-[[3-(1H-indol-3-yl)-2-methyl-2-[[[(2-methyl-1-cyclohexyl)oxy]carbonyl]amino]-1-oxopropyl]amino]-3-phenylpropyl]amino]-4-oxo-[1R-[1α[R*(S*)],2β]]-((–)-isomer), and
68. 2-butenoic acid, 4-[[2-[[3-(1H-indol-3-yl)-2-methyl-2-[[[(2-methyl-1-cyclohexyl)oxy]carbonyl]amino]-1-oxopropyl]amino]-3-phenylpropyl]amino]-4-oxo-[IR[1α[R*(S*)],2β]]-((–)-isomer).

Additionally preferred are the compounds:

69. [[3-[[3-(1H-indol-3-yl)-2-methyl-1-oxo-2-[[tricyclo[3.3.1.1$^{3,7}$]dec-2-yloxy)carbonyl]amino]propyl]amino]-1-oxo-2-phenylpropyl]amino]acetic acid,
70. [R-(R*,R*)]-[2-([3-(1H-indol-3-yl)-2-methyl-1-oxo-2-[[(tricyclo[3.3.1.1$^{3,7}$]dec-2-yloxy)carbonyl]amino]propyl]amino]-1-phenylethoxy]acetic acid,
71. [1R-(1α,2β[R*(R*)]]]-2-[[[2-[[3-(1H-indol-3-yl)-2-methyl-1-oxo-2-[[(tricyclo[3.3.1.1$^{3,7}$)]dec-2-yloxy)carbonyl]amino]propyl]amino)-1-phenylethyl]amino]carbonyl]cyclopropane carboxylic acid,
72. [1S-[1α,2β[S*(S*)]]]-2-[[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl)amino]carbonyl]cyclopropane carboxylic acid,
73. pR-R*,R*)]-3-[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethoxy]propanoic acid,
74. [R-(R*,R*)]-mono 2-[[3-(1H-indol-3-yl)-2-methyl-1-oxo-2-[[(tricyclo[3.3.1.1$^{3,7}$]dec-2-yloxy)carbonyl]amino]-1-phenylethyl butanedioic acid,
75. 3-[[3-[[3-(1H-indol-3-yl)-2-methyl-1-oxo-2-[[(tricyclo[3.3.1.1$^{3,7}$]dec-2-yloxy)carbonyl]amino]propyl]amino]-1-oxo-2-phenylpropyllamino]propanoic acid,
76. [R-(R*,S*)]-β-[[3-(1H-indol-3-yl)-2-methyl-1-oxo-2-[[(tricyclo[3.3.1.1$^{3,7}$]dec-2-yloxy)carbonyl]amino]propyl]amino]-4-iodobenzenebutanoic acid,
77. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]amino]-3-phenylpropyl]amino]-4-oxo-2-butenoic acid,
78. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]amino]-3-phenylpropyl]amino]-4-oxobutanoic acid, ((–)-isomer),
79. [1R -[1α[R*(R*)],2β]]-4-[[2-[[3-(1H-indol-3-yl)-2-methyl-2-[[[(2-methyl-1-cyclohexyl)oxy]carbonyl]amino]-1-oxopropyl]amino]-1-phenylethyl]amino]-4-oxo-2-butenoic acid,
80. 1R-[1α[R*(R*)],2β]]-4-[[2-[[3-(1H-indol-3-yl)-2-methyl-2-[[[(2-methyl-1-cyclohexyl)oxy]carbonyl]amino]-1-oxopropyl]amino]-1-phenylethyl]amino]-4-oxobutanoic acid, ((–)-isomer),
81. [R-(R*,S*)]-lg/-[[3-(1H-indol-3-yl)-2-methyl-1-oxo-2-[[(tricyclo[3.3.1.1$^{3,7}$]dec-2-yloxy)carbonyl]amino]propyl]amino]benzeneheptanoic acid,
82. 2-[[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]carbonyl-cyclopropanecarboxylic acid (cyclopropyl ring is trans-(±), other centers are R),
83. 2-methylcyclohexyl [1R-[1α[R*(S*)]],2β]-[[1-(hydroxymethyl)-2-phenylethyl]amino]-1-(1H-indol-3-ylmethyl) -1-methyl-2-oxoethyl]carbamate,
84. [R-[R*,S*-(E<E)][[-6-[[3-(1H-indol-3-yl)-2-methyl-1-oxo-2-[[(tricyclo[3.3.1.1$^{3,7}$]dec-2-yloxy)carbonyl]amino]propyl]amino]-7-phenyl-2,4-heptadienoic acid,
85. tricyclo[3.3.1.1$^{3,7}$]dec-2-yl [2-[[1-(hydroxymethyl)-2-hydroxy-2-phenylethyl]amino]-1-(1H-indol-3-ylmethyl)-1-methylethyl]carbamate,
86. tricyclo[3.3.1.1$^{3,7}$]dec-2-yl [R-(R*,R*)]-[1-(1H-indol-3-ylmethyl) -1-methyl-2-oxo-2-[2-[[1-oxo-3-(1H-tetrazol-5-yl)propyl]amino]-2-phenylethyl]amino]ethyl]carbamate, 87. [R-(R*,S*)]-2-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]sulfinyl]acetic acid,
88. [R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]sulfonyl]acetic acid,
89. ethyl (R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]sulfonyl]acetate,
90. 2-chlorocyclohexyl [2-[[1-(hydroxymethyl)-2-phenylethyl]amino]-1-(1H-indol-3-ylmethyl)-1-methyl-2-oxoethyl carbamate.

Isomer II
Ring Centers are trans, trp center is D, other center is S, ((−) or (+) form)

91. [R-[R*,R*(E)]]-4-[[2-[[3-(1H-indol-3-yl)-2-methyl-1-oxo-2-[[(tricyclo[3.3.1.1$^{3,7}$]dec-2-ylamino)carbonyl]amino]propyl]amino]-1-phenylethyl]amino]-4-oxo-2-butenoic acid,
92. [R-(R*,R*)]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxobutanoic acid,
93. [R-(R*,S*)-mono[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]butanedioate,
94. tricyclo[3.3.1.1$^{3,7}$]dec-2-yl [R-(R*,S*)-[2-[[1-(hydroxymethyl)-2-phenylethyl]amino]-1-(1H-indol-3-ylmethyl)-1-methyl-2-oxoethyl]carbamate,
95. [1S-[1α,2β[S*[S(E)]],4α]]-4-[[2-[[3-(1H-indol-3-yl)-2-methyl-1-oxo-2-[[[(1,7,7-trimethylbicyclo[2.2.1]hept-2-yl)oxy]carbonyl]amino]propyl]amino]-1-phenylethyl]amino]-4-oxo-2-butenoic acid,
96. [1S-[1α,2β[S*(S*)],4α]]-4-[[2-[[3-(1H-indol-3-yl)-2-methyl-1-oxo-[[[(1,7,7-trimethylbicyclo[2.2.1]-hept-2-yl)oxy]carbonyl]amino]propyl]amino]-1-phenylethyl]amino]-4-oxo-2-butenoic acid, (bicyclo system is 1S-endo),
97. [R-[R*,S*-(E)]]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-4-oxo-2-butenoic acid,
98. N-[2-methyl-N-[(tricyclo[3.3.1.1$^{3,7}$]dec-2-yloxy)carbonyl]-D-tryptophyl]-L-phenylalanylglycine,
99. [R-(R*,S*)[-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-4-oxobutanoic acid,
100. [R-(R*,R*)]-2-[[2-[[1,4-dioxo-4-(1H-tetrazol-5-ylamino)butyl]amino]-2-phenylethyl]amino]-1-(1H-indol-3-ylmethyl)-1-methyl-2-oxoethyl]carbamic acid,
101. [R-(R*,R*)]-3-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-3-oxopropanoic acid,
102. [R-(R*,S*)]-3-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-3-oxopropanoic acid,
103. [R-[R*,S*-(E)]]-4-[[2-[[3-(1H-indol-3-yl)-2-methyl-2-[[(bicyclo[3.3.1]non-9-yloxy)carbonyl]amino]-1-oxopropyl]amino]-3-phenylpropyl]amino]-4-oxo-2-butenoic acid,
104. [R-(R*,S*)]-5-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-5-oxopentanoic acid,
105. ethyl [R-(R*,S*)]-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]-sulfinyl]acetate,
106. [R-[R*,R*-(E)]]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxo-2-butenoic acid,
107. [R-(R*,S*)]-N-[3-[[3-(1H-indol-3-yl)-2-methyl-1-oxo-2-[[(tricyclo[3.3.1.1$^{3,7}$]dec-2-yloxy)carbonyl]amino]propyl]amino]-1-oxo-4-phenylbutyl]-β-alanine,
108. N-[N-[α-methyl-N-[(tricyclo[3.3.1.1$^{3,7}$]dec-2-yloxy)carbonyl]-D-tryotophyl]-L-phenylalanyl]-L-alanine,
109. [R-R*,S*)]-3-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]thio]propanoic acid,
110. [R-(R*,S*)]-[[2-[[2-[3-(1H-indol-3-yl)-2-methyl-1-oxo-2-[[(tricyclo[3.3.1.1$^{3,7}$]dec-2-yloxy)carbonyl]amino]propyl]amion]-3-phenylpropyl]thio]acetic acid,
111. [R-(R*,S*)]-β-[[3-(1H-indol-3-yl)-2-methyl-1-oxo-2-[[(tricyclo[3.3.1.1$^{3,7}$]dec-2-yloxy)carbonyl]amino]propyl]amino]benzenebutanoic acid,
112. tricyclo[3.3.1.1$^{3,7}$]dec-2-yl [R-(R*,S*)]-3-(1H-indol-3-ylmethyl)-3-methyl-4,10-dioxo-6-(phenylmethyl)-11-oxa-8-thia-2,5-diazatridecanoic acid,
113. [2-[[2-hydroxy-1-(hydroxymethyl)-2-phenylethyl]amino]-1-(hydroxymethyl)-1-(1H-indol-3-ylmethyl)-2-oxoethyl]-, tricyclo[3.3.1.1$^{3,7}$]dec-2-yl ester,
114. N-[α-methyl-N-[(tricyclo[3.3.1.1$^{3,7}$]dec-2-yloxy)carbonyl]-L-tryptophyl)-D-3-(phenylmethyl)-β-alanine,
115. (1R-trans)-N-[α-methyl-N-[[(2-methylcyclohexyl)oxy]carbonyl]-L-tryptophyl]-D-3(phenylmethyl) ((1R,2R)-N-[[(2-methylcyclohexyl)oxy]carbonyl]) ((α/-Me)LTrp-(D-3-Bzl)bAla-β-alanine ((−)-isomer), and
116. (1S-trans)-N-[α-methyl-N-[[(2-methylcyclohexyl)oxy]carbonyl]-D-tryptophyl]-L-3-(phenylmethyl)-β-alanine.

The more preferred compound is CI-988.
The most preferred compound is the N-methylglucamine salt of CI-988.
Pharmaceutical compositions of a compound of the present invention or its salts are produced by formulating the active compound in dosage unit form with a pharmaceutical carrier. Some examples of dosage unit forms are tablets, capsules, pills, powders, aqueous and nonaqueous oral solutions and suspensions, and parenteral solutions packaged in containers containing either one or some larger number of dosage units and capable of being subdivided into individual doses. Some examples of suitable pharmaceutical carriers, including pharmaceutical diluents, are gelatin capsules; sugars such as lactose and sucrose; starches such as corn starch and potato starch, cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma, propylene glycol, glycerin; sorbitol; polyethylene glycol; water; agar; alginic acid; isotonic saline, and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits but for practical purposes it is preferably present in a concentration of at least 10% in a solid composition and at least 2% in a primary liquid composition. The more satisfactory compositions are those in which a much higher proportion of the active ingredient is present.

Routes of administration of a subject compound or its salts are oral or parenteral. For example, a useful intravenous dose is between 100 and 800 mg and a useful oral dosage is between 200 and 800 mg.

A unit dosage form of the instant invention may also comprise other compounds useful in the therapy of depression.

A typical dose is, for example, from 600 to 2400 mg per day given in three individual doses.

A skilled physician will be able to determine the appropriate situation in which subjects are in need of such medication suffering from a cognitive disorder and will determine the appropriate route for administration by methods of the present invention.

The advantages of using the compounds of the invention are the compounds are well tolerated, are easily administered IV, are not metabolized in the body, do not cause sedation, and do not cause a withdrawal reaction. There are no cardiovascular side effects and the compounds do not potentiate the action of alcohol or of barbiturates.

Compounds useful in the method of treating cognitive disorders of the instant invention are those of formula

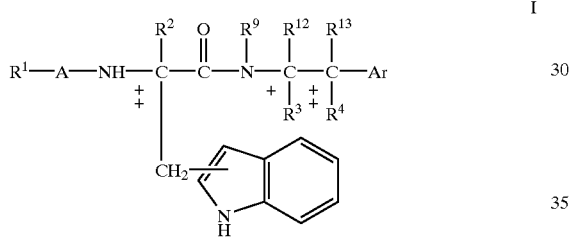

I or a pharmaceutically acceptable salt thereof wherein:

$R^1$ is a cycloalkyl or polycycloalkyl hydrocarbon of from three to twelve carbon atoms with from zero to four substituents each independently selected from the group consisting of a straight or branched alkyl of from one to about six carbon atoms, halogen, CN, OR*, SR*, $CO_2R^*$, $CF_3$, $NR^5R^6$, and —$(CH_2)_nOR^5$ wherein R* is hydrogen or a straight or branched alkyl of from one to six carbon atoms, $R^5$ and $R^6$ are each independently hydrogen or alkyl of from one to about six carbon atoms and n is an integer from zero to six;

A is —$(CH_2)_nCO$—, —$SO_2$—, —$S(=O)$—, —NHCO—,

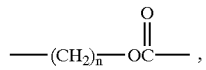

HO—SCO—, —O—$(CH_2)_nCO$— or —HC=CHCO— wherein n is an integer from zero to six;

$R^2$ is a straight or branched alkyl of from one to about six carbon atoms, —$HC=CH_2$, —C≡CH, —$CH_2$—CH=$CH_2$, —$CH_2C$≡CH, —$(CH_2)_nAr$, —$(CH_2)_nOR^*$, $(CH_2)_nOAr$, —$(CH_2)_nCO_2R^*$, or —$(CH_2)_nNR^5R^6$ wherein n, R*, $R^5$ and $R^6$ are as defined above and Ar is as defined below;

$R^3$ and $R^4$ are each independently selected from hydrogen, $R^2$ and —$(CH_2)_{n'}$—B—D wherein:
n' is an integer of from zero to three;
B is a bond, —OCO$(CH_2)_n$—,
—O$(CH_2)_n$—,
—$SO_2NH(CH_2)_n$—,
—$NHSO_2(CH_2)_n$—,
—$NHCO(CH_2)_n$—,
—$CONH(CH_2)_n$—,
—NHCOCH=CH—,
—COO$(CH_2)_n$—,
—CO$(CH_2)_n$—,
—S—$(CH_2)_n$—,
—S(=O)—$(CH_2)_n$—,
—$SO_2$—$(CH_2)_n$—,

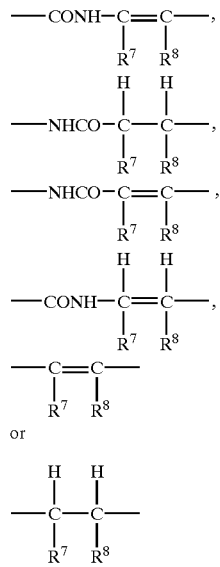

or wherein $R^7$ and $R^8$ are independently selected from hydrogen and $R^2$ or together form a ring $(CH_2)_m$ wherein m is an integer of from 1 to 5 and n is as defined above;

D is
—COOR*,
—$CH_2OR^*$,
—$CHR^2OR^*$,
—$CH_2SR^*$,
—$CHR^2SR^*$,
—$CONR^5R^6$,
—CN,
—$NR^5R^6$,
—OH,
—H and acid replacements tetrazole,

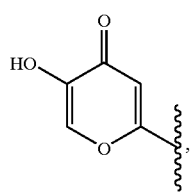 , 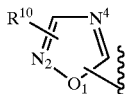

1,2,4 oxadiazole $R^{10}$ is OH, $NH_2$, $CH_3$ or Cl

or wherein

R*, $R^2$, $R^5$, and $R^6$ are as defined above;

$R^9$ is hydrogen or a straight or branched alkyl of from one to about six carbon atoms, —$(CH_2)_nCO_2R^*$, —$(CH_2)_nOAr'$, —$(CH_2)_nAr'$ or $(CH_2)_nNR^5R^6$, wherein n, R*, $R^5$, and $R^6$ are as defined above or taken from $R^3$ and Ar' is taken from Ar as defined below;

$R^{12}$ and $R^{13}$ are each independently hydrogen or are each independently taken with $R^3$ and $R^4$ respectively to form a moiety doubly bonded to the carbon atom; and Ar is a mono- or polycyclic unsubstituted or substituted carbo- or heterocyclic aromatic or hydroaromatic moiety.

Especially useful are compounds selected from:

1. [1S-[2α,2β[S*[S*(E)]],4α]]-4-[[2-[[3-(1H-indol-3-yl)-2-methyl-1-oxo-2-[[[((1,7,7-trimethylbicyclo-[2.2.1]hept-2-yl)oxy]carbonyl]amino]propyl]amino]-1-phenylethyl]amino]-4-oxo-2-butenoic acid,
2. [1S-[1α,2β[S*(S*)],4α]]-4-[[2-[[3-(1H-indol-3-yl)-2-methyl-1-oxo-2-[[[1,7,7-trimethylbicyclo-[2.2.1]hept-2-yl)oxy]carbonyl]amino]propyl]methylamino]-3-1-phenylethyl]amino]-4-oxobutanoic acid,
3. [1S-[1α,2β[S*(S*)],4α]]-4-[[2-[[3-(1H-indol-3-yl-2-methyl-1-oxo-2-[[[(1,7,7-trimethylbicyclo[2.2.1]-hept-2-yl)amino)carbonyl]amino]propyl]amino]-1-phenylethyl]amino]-4-oxobutanoic acid,
4. [R-(R*,R*)]-4-[[2-[[3-(1H-indol-3-yl)-2-methyl-1-oxo-2-[(tricyclo[3.3.1.1$^{3,7}$]dec-2-ylsulfonyl)amino]propyl]amino]-1-phenylethyl]amino]-4-oxobutanoic acid,
5. [R-(R*,S*)]-4-[[2-[[3-(1H-indol-3-yl)-2-methyl-1-oxo-2-[(tricyclo[3.3.1.1$^{3,7}$]dec-2-ylsulfonyl)amino]propyl]amino]-3-phenylpropyl]amino]-4-oxobutanoic acid,
6. [1R-[1α[R*(S*)],2β]] and [1S-[1α[S*(R*)),2β]]-4-[[2-[[2-[[[(2-fluorocyclohexyl)oxy]carbonyl]amino]-3-(1H-indol-3-yl)-2-methyl-1-oxopropyl]amino]-3-phenylpropyl]amino]-4-oxobutanoic acid,
7. [1R-[1α[R*(S*)],2β]] and [1S-[1α[S*(R*)],2β]]-4-[[2-[[2-[[[(2-fluorocyclohexyl)oxy]carbonyl]amino]-3-(1H-indol-3-yl)-2-methyl-1-oxopropyl]methylamino]-3-phenylpropyl]amino]-4-oxobutanoic acid,
8. [1R-[1α[R*(S*)],2β]] and [1S-[1α[S*(R*)],2β]]-4-[[2-[[3-(1H-indol-3-yl)-2-methyl-1-oxo-2-[[[[2-(trifluoromethyl)cyclohexyloxy]carbonyl]amino]propyl]amino]-3-phenylpropyl]amino]-4-oxobutanoic acid,
9. [1R-[1α[R*(S*)],2β]] and [1S-[1α[S*(R*)],2β]]-4-[[2-[[3-(1H-indol-3-yl)-2-methyl-1-oxo-2-[[[[2-(trifluoromethyl)cyclohexyl]oxy]carbonyl]amino]propyl]methylamino]-3-phenylpropyl]amino]-4-oxobutanoic acid,
10. [R-(R*,S*)]-4-[[2-[[3-(1H-indol-3-yl)-2-methyl-1-oxo-2-[[(tricyclo[3.3.1.1$^{3,7}$]dec-2-yloxy)carbonyl]amino]propyl]methylamino]-3-phenylpropyl]amino]-4-oxobutanoic acid,
11. [1S-[1α,2β[S*(R*)],4α]]-[1-(1H-indol-3-ylmethyl)-1-methyl-2-oxo-2-[[2-[[1-oxo-3-(1H-tetrazol-5-yl)propyl]amino]-1-(phenylmethyl)ethyl]amino]ethyl]carbamic acid, 1,7,7-trimethylbicyclo[2.2.1]hept-2-yl ester,
12. [1S-[1α,2β[S*,R*)]]-[1-(1H-indol-3-ylmethyl)-1-methyl-2-oxo-2-[[2-[[1-oxo-3-(1H-tetrazol-5-yl)propyl]amino]-2-phenylethyl)amino]ethyl]carbamic acid, 1,7,7-trimethylbicyclo[2.2.1]hept-2-yl ester,
13. N-[2-methyl-N-[(tricyclo[3.3.1.1$^{3,7}$]dec-2-yloxy)carbonyl]-D-tryptophyl]-L-phenylalanylglycine,
14. N-[2-methyl-N-[(tricyclo[3.3.1.1$^{3,7}$]dec-2-yloxy)carbonyl]-D-tryptophyl]-L-phenylalanyl-β-alanine, and
15. (R)-tricyclo[3.3.1.1$^{3,7}$]dec-2-yl [1-(1H-indol-3-ylmethyl)-1-methyl-2-[methyl(2-phenylethyl)amino]-2-oxo-ethylcarbamate.

In addition preferred compounds of the instant invention are:

16. (±)-trans-2-chlorocyclohexyl [1-(1H-indol-3-ylmethyl)-1-methyl-2-oxo-2-[(2-phenylethyl)amino]ethyl]ca
17. 2-chorocyclohexyl [2-[[1-(hydroxymethyl)-2-phenylethyl]amino]-1-(1H-indol-3-ylmethyl)-1-methyl-2-oxoethyl]carbamate,
18. 2-[[2-[[[(2-chlorocyclohexyl)oxy]carbonyl]amino]-3-[1H-indol-3-yl)-2-methyl-1-oxopropyl]amino]-3-phenylpropyl butanedioate,
19. 2-[[2-[[[(2-methylcyclohexyl)oxy]carbonyl]amino]-3-(1H-indol-3-yl)-2-methyl-1-oxopropyl]amino]-3-phenylpropyl butanedioate,
20. (±)-tricyclo[3.3.1.1$^{3,7}$]dec-2-yl[1-(1H-indol-3-ylmethyl)-1-methyl-2-oxo-2-[(2-phenylethyl)amino]ethylca
21. tricyclo[3.3.1.1$^{3,7}$]dec-2-yl[2-[[1-(hydroxymethyl)-2-phenylethyl]amino]-1-(1H-indol-3-ylmethyl)-1-methyl-2-oxoethyl]carbamate,
22. 2-[[3-(1H-indol-3-yl)-2-methyl-1-oxo-2-[[(tricyclo[3.3.1.1$^{3,7}$]dec-2-yloxy)carb butanedioate,
23. 2-[[3-(1H-indol-3-yl)-2-methyl-1-oxo-2-[[(tricyclo[3.3.1.1$^{3,7}$]dec-2-yloxy)carb butanedioate, 24. [R-(R*,R*)]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-4-oxo-2-butanoic acid, 25. [1S-[1α, 2β[S*(S*)],4α]]-4-[[2-[[3-(1H-indol-3-yl)-2-methyl-1-oxo-2-[[[(1,7,7-trimethylbicyclo-2.2.1]hept-2-yloxy)carbonyl]amino]propyl]amino]-3-phenylpropyl]amino]-4-oxo-2-butanoic acid, 26. [R-[R*,S*-(E)]]-4-[[2-[[3-(1H-indol-3-yl)-2-methyl-1-oxo-2-[[tricyclo[3.3.1.1$^{3,7}$]dec-2-yloxy)carbonyl]amino]propyl]amino]-3-phenylpropyl]amino]-4-oxo-2-butenoic acid, 27. [R-(R*,S*)]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-4oxobutanoic acid, 28. (R)-tricyclo[3.3.1.1$^{3,7}$]dec-2-yl [1-(1H-indol-3-ylmethyl)-1-methyl-2-[methyl(2-phenylethyl)amino]-2-oxoethylcarbamate, 29. [R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]sulfinyl]acetic acid, ethyl ester, 30. [R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]sulfonyl]acetic acid, ethyl ester, 31. [R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]sulfinyl]acetic acid, 32. [R-[R*,R*-(E)]]-4-[[2-[[3-(1H-indol-3-yl)-2-methyl-1-oxo-2-[[(tricyclo[3.3.1.1$^{3,7}$]dec-2-yloxy)]carbonyl]amino]propyl]amino]-1-phenylethyl]amino]-4-oxo-2-butenoic acid, b 33. [R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]thio]acetic acid, 34. [1S-[1α,2β[S*[S*(E)]],4α]]-4-[[2-[[3-(1H-indol-3-yl)-2-methyl-1-oxo-2-[[[(1,7,7-trimethylbicyclo[2.2.1]hept-2-yloxy)carbonyl]amino]propyl]amino]-1-phenylethyl]amino]-4-oxo-2-butenoic acid, methyl ester, (Bicyclo system is 1S-endo), 35. [1S-[1α, 2β[S*[S*(E)]],4α]]-4-[[2-[[3-(1H-indol-3-yl)-2-methyl-1-oxo-2-[[[(1,7,7-trimethylbicyclo-[2.2.1]hept-2-yloxy)carbonyl]amino]propyl]amino]-1-phenylethyl]amino]-4-oxo-2-butenoic acid, (Bicyclo system is 1S-endo), 36. [R-(R*,R*)]-3-[[2-[[3-(1H-indol-3-yl)-2-methyl-1-oxo-3-[[(tricyclo[3.3.1.1$^{3,7}$]dec-2-yloxy)carbonyl]amino]propyl]amino]-1-phenylethyl]amino]-3-oxo-propanoic acid, 37. [R-(R*,S*)]-3-(1H-indol-3-ylmethyl)-3-methyl-4,10-dioxo-6-(phenylmethyl)-11-oxo-8-thia-2,5-diazatridecanoic acid, tricyclo[3.3.1.1$^{3,7}$]dec-2-yl or ester, 38. [R-(R*,S*)]-β-[[3-(1H-indol-3-yl)-2-methyl-1-oxo-2-[[(tricyclo[3.3.1.1$^{3,7}$]dec-2-yloxy)]carbonyl]amino]propyl]amino]benzenebutanoic acid, 39. [R-(R*,S*)]-N-[3-[[3-(1H-indol-3-yl)-2-methyl-1-oxo-2-[[(tricyclo[3.3.1.1$^{3,7}$]dec-2-yloxy)carbonyl]amino]propyl]amino]-4-phenylbutyl]glycine, 40. [R-[R*,S*-(E)]]-4-[[2-[[3-(1H-indol-3-yl)-2-methyl-2-[[(bicyclo[3.3.1]non-9-yloxy)carbonyl]amino]propyl]amino]-1-phenylethyl]amino]-4-oxo-2-butenoic acid, 41. mono [R-(R*,R*)]-2-[[3-(1H-indol-3-yl)-2-methyl-1-oxo-2-[[(tricyclo[3.3.1.1$^{3,7}$]dec-2-yloxy)carbonyl]amino]propyl]amino]-4-[R-(R*,S*)]-butanedioate, 42. 3-[[3-[[3-(1H-indol-3-yl)-2-methyl-1-oxo-2-[[(tricyclo[3.3.1.1$^{3,7}$]dec-2-yloxy)]carbonyl]amino]propyl]amino]-1-oxo-2-phenylprophl]amino]propanoic acid (TRP is R, other center is RS), 43. [1R-[1α[R*(S*)],2β]]-4-[[2-[[3-(1H-indol-3-yl)-2-methyl-2-[[[(2-methyl-1-cyclohexyl)oxy]carbonyl]amino]propyl]amino]-1-phenylethyl]amino]-4-oxo-2-butenoic acid, (−)-Isomer, 44. [1R-[1α[R*(S*)],2β]]-4-[[2-[[3-(1H-indol-3-yl)-2-methyl-2-[[[(2-methyl-1-cyclohexyl)oxy]carbonyl]amino]propyl]amino]-1-phenylethyl]amino]-4-oxo-2-butenoic acid, (−)-Isomer, 45. [1R-[1α[R*(S*)],2β]]-4-[[2-[[3-(1H-indol-3-yl)-2-methyl-2-[[[(2-methyl-1-cyclohexyl)oxy]carbonyl]amino]propyl]amino]-1-phenylethyl]amino]-4-oxo-2-butenoic acid, (−)-Isomer, 46. [1R-[1α[R*(S*)],2β]]-4-[[2-[[3-(1H-indol-3-yl)-2-methyl-2-[[[(2-methyl-1-cyclohexyl)oxy]carbonyl]-amino]propyl]amino]-1-phenylethyl]amino]-4-oxo-2-butenoic acid, (−)-Isomer, 47. 2-methylcyclohexyl-[1R-[1α[R*(S*)]],2β]-[2-[[1-(hydroxymethyl)-2-phenylethyl]amino]-1-(1H-indol-3-ylmethyl)-1-methyl-2-oxoethyl]carbamate, 48. [R-[R*,S*-(E,E)]]-6-[[3-(1H-indol-3-yl)-2-methyl-1-oxo-2-[[(tricyclo[3.3.1.1$^{3,7}$]dec-2-yloxy)carbonyl]amino]propyl]amino]-7-phenyl-2,4-heptadienoic acid, 49. [R-(R*,R*)]-2-[[2-[[1,4-dioxo-4-(1H-tetrazol-5-ylamino)butyl]amino]-2-phenylethyl]amino]-1-(1H-indol-3-ylmethyl)-1-methyl-2-oxoethyl]carbamic acid, 50. tricyclo[3.3.1.1$^{3,7}$]dec-2-yl-[S-[R*,S*-(E)]]-12-(1H-indol-3-ylmethyl)-12-methyl-3,11-dioxo-9-(phenylmethyl)-2-oxa-7,10,13-triazatetradec-4-en-14-oate, 51. [R-(R*,S*)]-3-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-3-oxopropanoic acid, 52. ethyl [R-(R*,S*)]-[[2-[[2-[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]thio]-acetate, b 53. [R-(R*,S*)]-β-[[3-(1H-indol-3-yl)-2-methyl-1-oxo-2-[[(tricyclo[3.3.1.1$^{3,7}$]dec-2-yloxy)carbonyl]amino]propyl]amino]-4-iodo-benzenebutanoic acid, 54. [R-(R*,R*)]-2-[[3-(1H-indol-3-yl)-2-methyl-1-oxo-2-[[(1(tricyclo[[(3.3.1.1$^{3,7}$]dec-2-yloxy)carbonyl]amino]propyl]amino]-1-phenylethoxy]acetic acid, 55. [[3-[[3-(1H-indol-3-yl)-2-methyl-1-oxo-3-[[tricyclo(3.3.1.1$^{3,7}$]dec-2-yloxy)carbonyl]amino]propyl]amino]-1-oxo-2-phenylpropyl]amino] acid ((TRP)-phenylethyl]amino]-4-R, other center is RS), 56. (R)-[[[2-[[3-(1H-indol-3-yl)-1-oxo-2-methyl-2-[[(tricyclo[3.3.1.1$^{3,7}$]dec-2-yloxy)carbonyl]amino]propyl]amino]-1-phenylethylidene]amino]oxy]acetic acid, 57. [R-(R*,S*)]-β-[[3-(1H-indol-3-yl)-2-methyl-1-oxo-2-[[(tricyclo[3.3.1.1$^{3,7}$]dec-2-yloxy)carbonyl]amino]propyl]amino]benzenebutanoic acid, 58. [R-(R*,S*)]-N-[3-[[3-(1H-indol-3-yl)-2-methyl-1-oxo-2-[[(tricyclo[3.3.1.1$^{3,7}$]dec-2-yloxy)carbonyl]propyl]amino]-4-phenylbutyl]glycine, 59. 2-[[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]carbonyl]cyclopropanecarboxylic acid (cyclopropane ring is trans-(±), other centers are R), 60. carbamic acid, [1-(1H-indol-3-ylmethyl)-1-methyl-2-oxo-2-[[2-[[1-oxo-3-(1H-tetrazol-5-yl)propyl]amino]-2-phenylethyl]amino]ethyl-, tricyclo[3.3.1.1$^{3,7}$]dec-2-yl ester,[R-(R*,S*)], 61. benzeneheptanoic acid, α-[[3-(1H-indol-3-yl)-2-methyl-1-oxo-2-[[(tricyclo[3.3.1.1$^{3,7}$]dec-2-yloxy)carbonyl]amino]propyl]amino]-,[R-(R*,S*)]-, 62. methyl-(±)-β-[[[(2-phenylethyl)amino]carbonyl]-1β-[[(tricyclo[3.3.1.1$^{3,7}$]dec-2-yloxy)carbonyl]amino]-1H-indole-3-butanoate, 63. (R-(R*,S*))-4-[[2-(1H-indol-3-yl)-2-methyl-1-oxo-2-[[tricyclo[3.3.1.1$^{3,7}$]dec-2-yloxycarbonyl]amino]propyl]amino]-3-phenylpropyl]amino]-4-oxo-2-butenoic acid, 64. [bicyclo[2.2.2]oct-2-yl]amino-1-phenylpropyl]-[R*,S*]-4-oxo-2-butenoic (hydroxymethyl)-2-phenylethyl]amino]-1-(1H-indol-3- ylmethyl)-1-methyl-2-oxoethyl]amino]carbonyl]oxy]-4, 7,7-trimethyl-, [1R-[1α,2β,3α[R*(S*)],4α]]-,
65. butanoic acid, 4-[[2-[[3-(1H-indol-3-yl)-2-methyl-2-[[[(2-methyl-1-cyclohexyl)oxy]carbonyl]amino]-1-oxopropyl]amino]-1-phenylethyl]amino]-4-oxo-[1R-1α[R*(R*)]2β]]-((−)-isomer),
66. 2-butenoic acid, 4-[[2-[[3-(1H-indol-3-yl)-2-methyl-2-[[[(2-methyl-1-cyclohexyl)oxy]carbonyl]amino]-1-oxopropyl]amino]-1-phenylethyl]amino]-4-oxo-, [1R-[1α[R*(R*)],2β]]-((−)-isomer),
67. butanoic acid, 4-[[2-[[3-(1H-indol-3-yl)-2-methyl-2-[[[(2-methyl-1-cyclohexyl)oxy]carbonyl]amino]-1-oxopropyl]amino]-3-phenylpropyl]amino]-4-oxo-[1R-[1α[R*(S*)],2β]]-((−)-isomer), and
68. 2-butenoic acid, 4-[[2-[[3-(1H-indol-3-yl)-2-methyl-2-[[[(2-methyl-1-cyclohexyl)oxy]carbonyl]amino]-1-oxopropyl]amino]-3-phenylpropyl]amino]-4-oxo-[1R[1α[R*(S*)],2β]]-((−)-isomer).

Additionally preferred are the compounds:

69. [[3-[[3-(1H-indol-3-yl)-2-methyl-1-oxo-2-[[tricyclo[3.3.1.1$^{3,7}$]dec-2-yloxy)carbonyl]amino]propyl]amino]-1-oxo-2-phenylpropyl]amino]acetic acid,
70. [R-(R*,R*)]-[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethoxy]acetic acid,
71. [1R-[1α,2β[R*(R*)]]]-2-[[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]carbonyl]cyclopropane carboxylic acid,
72. [1S-[1α,2β[S*(S*)]]]-2-[[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]carbonyl]cyclopropane carboxylic acid,
73. pR-R*,R*)]-3-[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethoxy]propanoic acid,
74. [R-(R*,R*)]-mono 2-[[3-(1H-indol-3-yl)-2-methyl-1-oxo-2-[[(tricyclo[3.3.1.1$^{3,7}$]dec-2-yloxy)carbonyl]amino]-1-phenylethyl butanedioic acid,
75. 3-[[3-[[3-(1H-indol-3-yl)-2-methyl-1-oxo-2-[[(tricyclo3.3.1.1$^{3,7}$]dec-2-yloxy)carbonyl]amino]propyl]amino]-1-oxo-2-phenylpropyl]amino]propanoic acid,
76. [R-(R*,S*)]-β-[[3-(1H-indol-3-yl)-2-methyl-1-oxo-2-[[(tricyclo[3.3.1.1$^{3,7}$]dec-2-yloxy)carbonyl]amino]propyl]amino]-4-iodobenzenebutanoic acid,
77. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]amino]-3-phenylpropyl]amino]-4-oxo-2-butenoic acid,
78. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]amino]-3-phenylpropyl]amino]-4-oxobutanoic acid, ((−)-isomer),
79. [1R-[1α[R*(R*)],2β]]-4-[[2-[[3-(1H-indol-3-yl)-2-methyl-2-[[[(2-methyl-1-cyclohexyl)oxy]carbonyl]amino]-1-oxopropyl]amino]-1-phenylethyl]amino]-4-oxo-2-butenoic acid,
80. 1R-[1α[R*(R*)],2β]]-4-[[2-[[3-(1H-indol-3-yl)-2-methyl-2-[[[(2-methyl-1-cyclohexyl)oxy]carbonyl]amino]-1-oxopropyl]amino]-1-phenylethyl]amino]-4-oxobutanoic acid, ((−)-isomer),
81. [R-(R*,S*)]-lg/-[[3-(1H-indol-3-yl)-2-methyl-1-oxo-2-[[(tricyclo[3.3.1.1$^{3,7}$]dec-2-yloxy)carbonyl]amino]propyl]amino]benzeneheptanoic acid,
82. 2-[[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]carbonyl]cyclopropanecarboxylic acid (cyclopropyl ring is trans-(±), other centers are R),
83. 2-methylcyclohexyl [1R-[1α[R*(S*)]],2β]-[[1-(hydroxymethyl)-2-phenylethyl]amino]-1-(1H-indol-3-ylmethyl)-1-methyl-2-oxoethyl]carbamate,
84. [R-[R*,S*-(E<E)][,-6-[[3-(1H-indol-3-yl)-2-methyl-1-oxo-2-[[(tricyclo[3.3.1.1$^{3,7}$]dec-2-yloxy)carbonyl]amino]propyl]amino]-7-phenyl-2,4-heptadienoic acid,
85. tricyclo[3.3.1.1$^{3,7}$]dec-2-yl [2-[[1-(hydroxymethyl)-2-hydroxy-2-phenylethyl]amino]-1-(1H-indol-3-ylmethyl)-1-methylethyl]carbamate,
86. tricyclo[3.3.1.1$^{3,7}$]dec-2-yl [R-(R*,R*)]-[1-(1H-indol-3-ylmethyl)-1-methyl-2-oxo-2-[[2-[[1-oxo-3-(1H-tetrazol-5-yl)propyl]amino]-2-phenylethyl]amino]ethyl] carbamate,
87. [R-(R*,S*)]-2-[[2-[[3-(1H-indol-3-yl)-2-methyl-1-oxo-2-[[(tricyclo[3.3.1.1$^{3,7}$]dec-2-yloxy)carbonyl]amino)propyl]amino]-3-phenylpropyl]sulfinyl]acetic acid,
88. [R-(R*,S*)]-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]sulfonyl]acetic acid,
89. ethyl [R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]sulfonyl]acetate,
90. 2-chlorocyclohexyl [2-[[1-(hydroxymethyl)-2-phenylethyl]amino]-1-(1H-indol-3-ylmethyl)-1-methyl-2-oxoethyl]carbamate,
91. [R-[R*,R*(E)]]-4-[[2-[[3-(1H-indol-3-yl)-2-methyl-1-oxo-2-[[(tricyclo[3.3.1.1$^{3,7}$]dec-2-ylamino)carbonyl]amino]propyl]amino]-1-phenylethyl]amino]-4-oxo-2-butenoic acid,
92. [R-(R*,R*)]-4-[[2-[[3-(1H-indol-3-yl)-2-methyl-1-oxo-2-[[(tricyclo [3.3.1.1$^{3,7}$]dec-2-yloxy)carbonyl]amino]propyl]amino]-1-phenylethyl]amino]-4-oxobutanoic acid,
93. [R-(R*,S*)]-mono[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]butanedioate,
94. tricyclo[3.3.1.1$^{3,7}$]dec-2-yl [R-(R*,S*)-[2-[[1-(hydroxymethyl)-2-phenylethyl]amino]-1-(1H-indol-3-ylmethyl)-1-methyl-2-oxoethyl]carbamate,
95. [1S-[1α, 2β[S*[S(E)]],4α]]-4-[[2-[[3-(1H-indol-3-yl)-2-methyl-1-oxo-2-[[[(1,7,7-trimethylbicyclo[2.2.1]hept-2-yl)oxy]carbonyl]amino]propyl]amino]-1-phenylethyl]amino]-4-oxo-2-butenoic acid,
96. [1S-[1α,2β[S*(S*)],4α]]-4-[[2-[[3-(1H-indol-3-yl)-2-methyl-1-oxo-[[[(1,7,7-trimethylbicyclo[2.2.1]-hept-2-yl)oxy]carbonyl]amino]propyl]amino]-1-phenylethyl]amino]-4-oxo-2-butenoic acid, (bicyclo system is 1S-endo),
97. [R-[R*,S*-(E)]]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-4-oxo-2-butenoic acid,
98. N-[2-methyl-N-[(tricyclo[3.3.1.1$^{3,7}$]dec-2-yloxy)carbonyl]-D-tryptophyl]-L-phenylalanylglycine,
99. [R-(R*,S*)[-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-4-oxobutanoic acid,
100. [R-(R*,R*)]-2-[[2-[[1,4-dioxo-4-(1H-tetrazol-5-ylamino)butyl]amino]-2-phenylethyl]amino]-1-(1H-indol-3-ylmethyl)-1-methyl-2-oxoethyl]carbamic acid,
101. [R-(R*,R*)]-3-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-3-oxopropanoic acid, 102. [R-(R*,S*)]-3-[[2-[[3-(1H-indol-3-yl)-2-methyl-1-oxo-2-[[(tricyclo[3.3.1.1³,⁷]dec-2-yloxy)carbonyl]amino]propyl]amino]-3-phenylpropyl]amino]-3-oxopropanoic acid,
103. [R-[R*,S*-(E)]]-4-[[2-[[3-(1H-indol-3-yl)-2-methyl-2-[[(bicyclo[3.3.1]non-9-yloxy)carbonyl]amino]-1-oxopropyl]amino]-3-phenylpropyl]amino]-4-oxo-2-butenoic acid,
104. [R-(R*,S*)]-5-[[2-[[3-(1H-indol-3-yl)-2-methyl-1-oxo-2-[[(tricyclo[3.3.1.1³,⁷]dec-2-yloxy)carbonyl]amino]propyl]amino]-3-phenylpropyl]amino]-5-oxopentanoic acid,
105. ethyl [R-(R*,S*)]-[[2-[[3-(1H-indol-3-yl)-2-methyl-1-oxo-2-[[(tricyclo[3.3.1.1³,⁷]dec-2-yloxy)carbonyl]amino]propyl]amino]-3-phenylpropylsulfinyl]acetate,
106. [R-[R*,R*-(E)]]-4-[[2-[[3-(1H-indol-3-yl)-2-methyl-1-oxo-2-[[(tricyclo[3.3.1.1³,⁷]dec-2-yloxy)carbonyl]amino]propyl]amino]-1-phenylethyl]amino]-4-oxo-2-butenoic acid,
107. [R-(R*,S*)]-N-[3-[[3-(1H-indol-3-yl)-2-methyl-1-oxo-2-[[(tricyclo[3.3.1.1³,⁷]dec-2-yloxy)carbonyl]amino]propyl]amino]-1-oxo-4-phenylbutyl]-β-alanine,
108. N-[N-[α-methyl-N-[(tricyclo[3.3.1.1³,⁷]dec-2-yloxy)carbonyl]-D-tryotophyl]-L-phenylalanyl]-L-alanine,
109. [R-R*,S*)]-3-[[2-[[3-(1H-indol-3-yl)-2-methyl-1-oxo-2-[[(tricyclo[3.3.1.1³,⁷]dec-2-yloxy)carbonyl]amino]propyl]amino]-3-phenylpropyl]thio]propanoic acid,
110. [R-(R*,S*)]-[[2-[[2-[3-(1H-indol-3-yl)-2-methyl-1-oxo-2-[[(tricyclo[3.3.1.1³,⁷]dec-2-yloxy)carbonyl]amino]propyl]amion]-3-phenylpropyl]thio]acetic acid,
111. [R-(R*,S*)]-β-[[3-(1H-indol-3-yl)-2-methyl-1-oxo-2-[[(tricyclo[3.3.1.1³,⁷]dec-2-yloxy)carbonyl]amino]propyl]amino]benzenebutanoic acid,
112. tricyclo[3.3.1.1³,⁷]dec-2-yl (R-(R*,S*)]-3-(1H-indol-3-ylmethyl)-3-methyl-4,10-dioxo-6-(phenylmethyl)-11-oxa-8-thia-2,5-diazatridecanoic acid,
113. [2-[[2-hydroxy-1-(hydroxymethyl)-2-phenylethyl]amino]-1-(hydroxymethyl)-1-(1H-indol-3-ylmethyl)-2-oxoethyl]-, tricyclo[3.3.1.1³,⁷]dec-2-yl ester,
114. N-[α-methyl-N-[(tricyclo[3.3.1.1³,⁷]dec-2-yloxy)carbonyl]-L-tryptophyl]-D-3-(phenylmethyl)-β-alanine,
115. (1R-trans)-N-[α-methyl-N-[[(2-methylcyclohexyl)oxy]carbonyl]-L-tryptophyl]-D-3-(phenylmethyl) ((1R,2R)-N-[[(2-methylcyclohexyl)oxy]-carbonyl])(α/-Me)LTrp-(D-3-Bzl)bAla-β-alanine ((−)-isomer), and
116. (1S-trans)-N-[α-methyl-N-[[(2-methylcyclohexyl)oxy]carbonyl]-D-tryptophyl]-L-3-(phenylmethyl)-β-alanine.

Other compounds useful in the method of treating cognitive disorders of the instant invention are those of formula

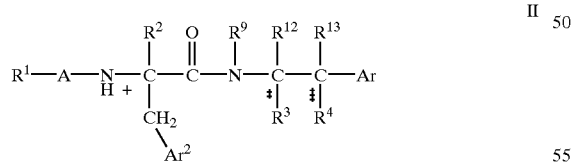

or a pharmaceutically acceptable salt thereof wherein:

$R^1$ is a cycloalkyl or polycycloalkyl hydrocarbon of from three to twelve carbon atoms with from zero to four substituents each independently selected from the group consisting of a straight or branched alkyl of from one to about six carbon atoms, halogen, CN, OR*, SR*, $CO_2R^*$, $CF_3$, $NR^5R^6$, and $—(CH_2)_nOR^5$ wherein R* is hydrogen or a straight or branched alkyl of from one to six carbon atoms, $R^5$ and $R^6$ are each independently hydrogen or alkyl of from one to about six carbon atoms and n is an integer from zero to six;

A is $—(CH_2)_nCO—$, $—SO_2—$, $—S(=O)—$, $—NHCO—$,

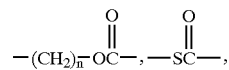

$—O—(CH_2)_nCO—$, or $—HC=CHCO—$ wherein n is an integer from zero to six;

$R^2$ is a straight or branched alkyl of from one to about six carbon atoms, $—HC=CH_2$, $—C\equiv CH_2$, $—(CH_2)_n—CH=CH$, $—(CH_2)_nC\equiv CH$, $—(CH_2)_nAr$, $—(CH_2)_nOR^*$, $—(CH_2)_nOAr$, $—(CH_2)_nCO_2R^*$, or $—(CH_2)_nNR^5R^6$ wherein n, R*, $R^5$, and $R^6$ are as defined above and Ar is as defined below;

$R^3$ and $R^4$ are each independently selected from hydrogen, $R^2$ and $—(CH_2)_n—B—D$ wherein:

n' is an integer of from zero to three;

B is a bond,
—OCO(CH_2)_n—,
—O(CH_2)_n—,
—NHCO(CH_2)_n—,
—CONH(CH_2)_n—,
—NHCOCH=CH—,
—COO(CH_2)_n—,
—CO(CH_2)_n—,
—S—(CH_2)_n—,
—S(=O)—(CH_2)_n—,
—SO_2—(CH_2)_n—,
—NHSO_2—(CH_2)_n—,
—SO_2NH(CH_2)_n—,

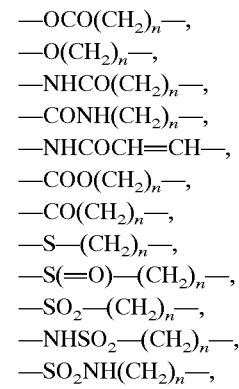

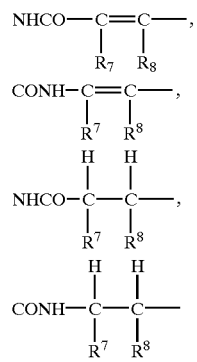

wherein $R^7$ or $R^8$ are independently selected from hydrogen and $R^2$ or together form a ring $(CH_2)_m$ wherein m is an integer of from 1 to 5 and n is as defined above;

D is
—COOR*,
—CH_2OR*,
—CHR^2OR*,
—CH_2SR*,
—CHR^2SR*,
—CONR^5R^6,
—CN,
—NR^5R^6,
—OH,

—H and acid replacements such as tetrazole

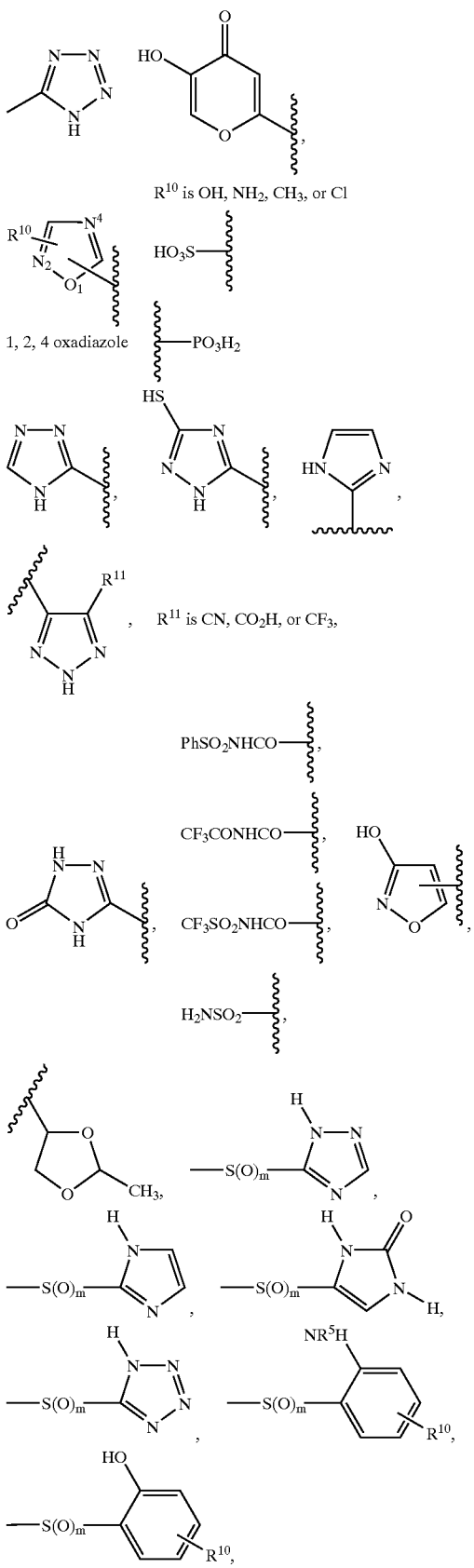

wherein
m is an integer of from 0 to 2, wherein R*, $R^2$, $R^5$, and $R^6$ are as defined above;
$R^9$ is hydrogen or a straight or branched alkyl of from one to about six carbon atoms, —$(CH_2)_nCO_2R^*$, —$(CH_2)_nOAr'$, —$(CH_2)_nNR^5R^6$, wherein n, R*, $R^5$, and $R^6$ are as defined above or taken from $R^3$ and Ar' is taken from Ar as defined below;
$R^{12}$ and $R^{13}$ are each independently hydrogen or are each independently taken with $R^3$ and $R^4$, respectively, to form a moiety doubly bonded to the carbon atom;
Ar is a mono- or polycyclic unsubstituted or substituted carbo- or heteroaromatic or carbo- or heterohydroaromatic moiety; and
$Ar^2$ can be selected from Ar as defined above or the $CH_2Ar^2$ moiety of formula I is the sidechain of a biologically significant amino acid, with the proviso that $Ar^2$ cannot be $Ar^2$ is also —$(CH_2)_2NHC(=NH)NHNO_2$, —$(CH_2)_2NMe_2$, or —$CH_2CO_2CH_3$.

Especially useful are compounds selected from

Tricyclo[3.3.1.1$^{3,7}$]dec-2-yl[2-[[1-(hydroxymethyl)-2-phenylethyl]amino]-1-methyl-2-oxo-1-(9H-pyrido[3,4-b]indol-3-ylmethyl)ethyl]-carbamate (alanine center is RS, other center is S), Tricyclo[3.3.1.1$^{3,7}$]dec-2-yl[1-methyl-1-[[9-(methylsulfonyl)-9H-pyrido[3,4-b]indol-3-yl]methyl]-2-oxo-2-[(2-phenylethyl)amino]ethyl]-carbamate, Tricyclo[3.3.1.1$^{3,7}$]dec-2-yl[2-[[1-(hydroxymethyl)-2-phenylethyl]amino]-1-methyl-1-[[9-(methylsulfonyl)-9H-pyrido[3,4-b]indol-3-yl]methyl]-2-oxoethyl]carbamate (phenylmethyl center S, other center RS), Tricyclo[3.3.1.1$^{3,7}$]dec-2-yl[2-[[1-(hydroxymethyl)-2-phenylethyl]amino]-1-methyl-1-(1-naphthalenylmethyl)-2-oxoethyl]carbamate (naphthalenylmethyl center is RS, other center is S), Tricyclo[3.3.1.1$^{3,7}$]dec-2-yl[2-[[1-hydroxymethyl)-2-phenylethyl]amino]-1-methyl-1-(2-naphthalenylmethyl)-2-oxoethyl]carbamate (naphthalene center is RS, hydroxymethyl center is S), Tricyclo[3.3.1.1$^{3,7}$]dec-2-yl(±)-[1-methyl-1-(1-naphthalenylmethyl)-2-oxo-2-[(2-phenylethyl)amino]ethyl]carbamate, Tricyclo[3.3.1.1$^{3,7}$]dec-2-yl(±)-[1-methyl-1-(2-naphthalenylmethyl)-2-oxo-2-[(2-phenylethyl)amino]ethyl]carbamate, Tricyclo[3.3.1.1$^{3,7}$]dec-2-yl[2-[[1-(hydroxymethyl)-2-phenylethyl]amino]-1-methyl-1-(2-naphthalenylmethyl)-2-oxoethyl]carbamate (hydroxy center is S, other center is R or S) (Isomer I), Tricyclo[3.3.1.1$^{3,7}$]dec-2-yl(±) [1-(3-benzofuranylmethyl)-1-methyl-2-oxo-2-[(2-phenylethyl)amino]ethyl]carbamate, Tricyclo[3.3.1.1$^{3,7}$]dec-2-yl[1-(3-benzofuranylmethyl)-2-[[1-(hydroxymethyl)-2-phenylethyl]amino]-1-methyl-2-oxoethyl[carbamate (benzofuranylmethyl center is RS, other center is S), Tricyclo[3.3.1.1$^{3,7}$]dec-2-yl[1-[(2-bromo-3-benzofuranyl)methyl]-2-[[1-(hydroxymethyl)-2-phenylethyl]amino]-1- methyl-2-oxoethyl]carbamate (benzofuran center is RS, hydroxymethyl center is S), Tricyclo[3.3.1.1³,⁷]dec-2-yl(±)-[1-[(2-bromo-3-benzofuranyl)methyl]-1-methyl-2-oxo-2-[(2-phenylethyl)amino]ethyl]carbamate, 2-Methylpropyl 2-[[2-methyl-1-oxo-3-(3-pyridinyl)-2-[[(tricyclo[3.3.1.1³,⁷]dec-2-yloxy)carbonyl]amino] propyl]amino]-3-phenylpropyl carbonate (pyridine center is RS, other center is S), Tricyclo[3.3.1.1³,⁷]dec-2-yl[2-[[1-hydroxymethyl)-2-phenylethyl]amino]-1-methyl-2-oxo-1-(3-pyridinylmethyl)ethyl]carbamate (hydroxymethyl center is S, other is (±)) (Diastereomer I), Tricyclo[3.3.1.1³,⁷]dec-2-yl(±)-[1-methyl-2-oxo-2[(2-phenylethyl)amino]-1-(4-pyridinylmethyl)ethyl] carbamate, Tricyclo[3.3.1.1³,⁷]dec-2-yl [2-[[1-(hydroxymethyl)-2-phenylethyl]amino]-1-methyl-2-oxo-1-(2-pyridinylmethyl)ethyl]carbamate (hydroxymethyl center is S, other center is R or S) (Diastereomer I), Tricyclo[3.3.1.1³,⁷]dec-2-yl(±)-[1-methyl-2-oxo-2-[(2-phenylethyl)amino]-1-(2-pyridinyl)methyl)ethyl] carbamate, Tricyclo[3.3.1.1³,⁷]dec-2-yl(±)-[-[(2-aminophenyl)methyl]-1-methyl-2-oxo-2-[(2-phenylethyl)amino]ethyl] carbamate, Tricyclo[3.3.1.1³,⁷]dec-2-yl(±)-[1-[(2-hydroxyphenyl)methyl]-1-methyl-2-oxo-2-[(2-phenylethyl)amino]ethyl] carbamate, Tricyclo[3.3.1.1³,⁷]dec-2-yl(±)-[1-methyl-2-oxo-2-[(2-phenylethyl)amino]-1-[(2-quinolinyl)methyl]ethyl] carbamate, Tricyclo[3.3.1.1³,⁷]dec-2-yl[2-[[1-(hydroxymethyl)-2-phenylethyl]amino]-1-methyl-2-oxo-1-(4-quinolinylmethyl)ethyl]carbamate (hydroxymethyl center is S, other center is RS), Tricyclo[3.3.1.1³,⁷]dec-2-yl) (±)-[1-methyl-2-oxo-2-[(2-phenylethyl)-amino]-1-(4-quinolinylmethyl)ethyl] carbamic acid, Tricyclo[3.3.1.1³,⁷]dec-2-yl(±)-[1-methyl-2-oxo-2-[(2-phenylmethyl)amino]-1-(3-quinolinylmethyl)ethyl] carbamate, Tricyclo[3.3.1.1³,⁷]dec-2-yl[2-[[1-(hydroxymethyl)-2-phenylethyl]amino]-1-methyl-2-oxo-1-(2-quinolinylmethyl)ethyl[carbamate (alanine center is RS, other center is S), Tricyclo[3.3.1.1³,⁷]dec-2-yl [2-[(2-amino-2-phenylethyl)amino]-1-(1H-indazol-3-ylmethyl)-1-methyl-2-oxoethyl] carbamate, 4-[[2-[[2-methyl-1-oxo-3-(1,2,3,4-tetrahydro-2-quinolinyl)-2-[[(tricyclo[3.3.1.1³,⁷]dec-2-yloxy)carbonyl]amino] propyl]amino]-1-phenylethyl]amino]-4-oxobutanoic acid compd. with 1-deoxy-1-(methylamino)-D-glucitol, 4-[[2-[[3-(1,2-dihydro-2-quinolinyl)-2-methyl-1-oxo-2-[[(tricyclo[3.3.1.1³,⁷]dec-2-yloxy)carbonyl]amino] propyl]amino]-1-phenylethyl]amino]-4-oxobutanoic acid compd. with 1-deoxy-1-(methylamino)-D-glucitol, 4-[[2-[[2-methyl-1-oxo-3-(4-quinolinyl)-2-[[(tricyclo [3.3.1.1³,⁷]dec-2-yloxy)carbonyl]amino]propyl]amino]-1-phenylethyl]amino]-4-oxobutanoic acid compd. with 1-deoxy-1-(methylamino)-D-glucitol, Tricyclo[3.3.1.1³,⁷]dec-2-yl(±)-[1-(1H-indazol-3-ylmethyl)-1-methyl-2-oxo-2-[(2-phenylethyl)amino]ethyl] carbamate, Tricyclo[3.3.1.1³,⁷]dec-2-yl [2-[[1-(hydroxymethyl)-2-phenylethyl]amino]-1-(1H-indazol-3-ylmethyl)-1-methyl-2-oxoethyl]carbamate (hydroxymethyl center is S, other center is RS), 4-[[2-[3-(1H-indazol-3-yl)-2-methyl-1-oxo-2-[[(tricyclo [3.3.1.1³,⁷]dec-2-yloxy) carbonyl]amino]propyl]amino]-1-phenylethyl]amino]-4-oxobutanoic acid (mixture of isomers), Tricyclo[3.3.1.1³,⁷]dec-2-yl(±)-1-[1-(1H-benzimidazol-2-ylmethyl)-1-methyl-2-oxo-2-[(2-phenylethyl)amino] ethyl]carbamate, Tricyclo[3.3.1.1³,⁷]dec-2-yl[1-(1H-benzimidazol-2-ylmethyl)-2-[[1-(hydroxymethyl)-2-phenylethyl]amino]-1-methyl-2-oxoethyl]carbamate (hydroxy center is S, other center is RS), Tricyclo [3.3.1.1³,⁷]dec-2-yl[1-(benzo[b]thien-3-ylmethyl)-2-[[1-(hydroxymethyl)-2-phenylethyl]amino]-1-methyl-2-oxoethyl]-carbamate (benzothiophene center is RS, hydroxymethyl center is S), Tricyclo[3.3.1.1³,⁷]dec-2-yl(±)-[1-(benzo[b]thien-3-ylmethyl)-1-methyl-2-oxo-2-[(2-phenylethyl)amino] ethyl]carbamate, Tricyclo[3.3.1.1³,⁷]dec-2-yl-(R or S,R)-[2-[[2-(2,5-dioxo-1-pyrrolidinyl)-2-phenylethyl]amino]-1-(1H-indazol-3-ylmethyl)-1-methyl-2-oxoethyl]carbamate, Tricyclo[3.3.1.1³,⁷]dec-2-yl-(S or R,R)-[2-[[2-(2,5-dioxo-1-pyrrolidinyl)-2-phenylethyl]amino]-1-(1H-indazol-3-ylmethyl)-1-methyl-2-oxoethyl]carbamate, Tricyclo[3.3.1.1³,⁷]dec-2-yl [2-[[2-hydroxy-1-(hydroxymethyl)-2-phenylethyl]amino]-1-methyl-2-oxo-1-[[4-(phenylmethoxy)phenyl]methyl]ethyl]carbamate, Tricyclo[3.3.1.1³,⁷]dec-2-yl [2-[[2-hydroxy-1-(hydroxymethyl)-2-phenylethyl]amino]-1-[(4-hydroxyphenyl)methyl]-1-methyl-2-oxoethyl]carbamate (Mixture of [1S-[1R*(R*),2R*]] and [1S-[1R*(S*),2R*]] isomers), Tricyclo[3.3.1.1³,⁷]dec-2-yl [2-[[2-hydroxy-1-(hydroxymethyl)-2-phenylethyl]amino]-1-[(4-methoxyphenyl)methyl]-1-methyl-2-oxoethyl]carbamate (Mixture of [1S-[1R*(R*),2R*)]] and [1S-[1R*(S*), 2R*]]isomers), Tricyclo[3.3.1.1³,⁷]dec-1-yl [2-[[2-hydroxy-1-(hydroxymethyl)-2-phenylethyl]amino]-1-methyl-2-oxo-1-[[4-(phenylmethoxy)phenyl]methyl]ethyl]carbamate (Mixture of [1S-[1R*(R*),2R*]] and [1S-[1R*(S*),2R*]] isomers), Tricyclo[3.3.1.1³,⁷]dec-2-yl (±)-[1-[(3,5-dimethyl-4-isoxazolyl)methyl]-1-methyl-2-oxo-2-[(2-phenylethyl) amino]ethyl]carbamate, Tricyclo[3.3.1.1³,⁷]dec-2-yl (±)-[l-[[2-(acetylamino)-4-thiazolyl]methyl]-1-methyl-2-oxo-2-[(2-phenylethyl) amino]ethyl]carbamate, Tricyclo[3.3.1.1³,⁷]dec-2-yl (±)-[1-(1H-benzotriazol-1-ylmethyl)-1-methyl-2-oxo-2-[(2-phenylethyl)amino] ethyl]carbamate, Tricyclo[3.3.1.1³,⁷]dec-2-yl (RS,S) [2-[[1-(hydroxymethyl)-2-phenylethyl]amino]-1-methyl-2-oxo-1-[[4-(1,2,3-thiadiazol-4-yl)phenyl]methyl]ethyl]carbamate, Tricyclo[3.3.1.1³,⁷]dec-2-yl (S or R, S)-[2-[[2-hydroxy-1-(hydroxymethyl)-2-phenylethyl]amino]-1-methyl-2-oxo-1-[[4-(1,2,3-thiadiazol-4-yl)phenyl]methyl]ethyl] carbamate, Tricyclo[3.3.1.1³,⁷]dec-2-yl-(S or R,R)-[2-[[2-(2,5-dioxo-1-pyrrolidinyl)-2-phenylethyl]amino]-1-(1H-indazol-3-ylmethyl)-1-methyl-2-oxoethyl]carbamate, 4-[[2-[[2-Methyl-1-oxo-3-(4-pyridinyl)-2-[[(tricyclo [3.3.1.1³,⁷]dec-2-yloxy)carbonyl]amino]propyl]amino]-1-phenylethyl]amino]-4-oxobutanoic acid, 4-[[2-[[3-(2,3-dihydro-1-methyl-5-phenyl-1H-benzodiazepin-2-yl)-2-methyl-1-oxo-2-[[(tricyclo-[3.3.1.1³,⁷]dec-2-yloxy)carbonyl]amino]propyl]amino]-

1-phenylethyl]amino]-4-oxobutanoic acid compd. with 1-deoxy-1-(methylamino)-D-glucitol, Tricyclo[3.3.1.1$^{3,7}$]dec-2-yl [2-[[1-(hydroxymethyl)-2-phenylethyl]amino]-1-methyl-2-oxo-1-(2-pyridinylmethyl}ethyl]carbamate, N-oxide, Tricyclo[3.3.1.1$^{3,7}$]dec-2-yl [1-[(2,3-dihydro-1-methyl-5-phenyl-1H-1,4-benzodiazepin-2-yl)methyl]-1-methyl-2-[(2-phenylethyl)amino]-2-oxoethyl]carbamate, Tricyclo[3.3.1.1$^{3,7}$]dec-2-yl [2-[[1-hydroxymethyl)-2-phenylethyl]amino]-1-methyl-2-oxo-1-(4-pyridinylmethyl)ethyl]carbamate, Tricyclo[3.3.1.1$^{3,7}$]dec-2-yl (±)-[1-methyl-2-oxo-2-[(2-phenylethyl)amino]-1-[(5,6,7,8-tetrahydro-5,5,8,8-tetramethyl-2-naphthalenyl)methyl]ethyl]carbamate, Tricyclo[3.3.1.1$^{3,77}$]dec-2-yl [1S-[1R*(R or S),2R*]]-[2-[[2-hydroxy-1-(hydroxymethyl)-2-phenylethyl]amino]-1-methyl-2-oxo-1-(1H-pyrrolo[2,3-b]pyridin-3-ylmethyl)ethyl]carbamate, Tricyclo[3.3.1.1$^{3,7}$][1S-[1R*(S or R),2R*]]-[2-[[2-hydroxy-1-(hydroxymethyl)-2-phenylethyl]amino]-1-methyl-2-oxo-1-(1H-pyrrolo[2,3-b]pyridin-3-ylmethyl)ethyl] carbamate, Tricyclo[3.3.1.1$^{3,7}$]dec-2-yl [1S-[1R*(R or S),2R*]]-[2-[[2-hydroxy-1-(hydroxymethyl)-2-phenylethyl]amino]-1-methyl-2-oxo-1-(1H-pyrrolo[3,2-c]pyridin-3-ylmethyl)ethyl]carbamate, Tricyclo[3.3.1.1 13,7][1S-[1R*(S or R),2R*]]-[2-[[2-hydroxy-1-(hydroxymethyl)-2-phenylethyl]amino]-1-methyl-2-oxo-1-(1H-pyrrolo[3,2-c]pyridin-3-ylmethyl)ethyl]carbamate, Carbamic acid, [-[(2,3-dimethyl)-1H-pyrrol-4-ylmethyl]-1-methyl-2-oxo-2-[(2-phenylethyl)amino]ethyl-, tricyclo[3.3.1.1$^{3,7}$]dec-2-yl ester, Carbamic acid, [1-[(2,3-dimethyl)-1H-pyrrol-4-ylmethyl]-2-[[1-(hydroxymethyl)-2-hydroxy-2-phenylethyl]amino]-1-methylethyl]-, tricyclo[3.3.1.1$^{3,7}$]dec-2-yl ester (mixture of isomers), Carbamic acid, [1-(imidazo[1,5-a]pyridin-3-ylmethyl)-2-oxo-2-[(2-phenylethyl)amino]ethyl]-, tricyclo[3.3.1.1$^{3,7}$]dec-2-yl ester, and Carbamic acid, [2-[[1-(hydroxymethyl)-2-hydroxy-2-phenylethyl]amino]-1-(imidazo[1,5-a]pyridin-3-ylmethyl)-1-methylethyl]-, tricyclo[3.3.1.1$^{3,7}$]dec-2-yl ester (mixture of isomers).

Other compounds useful in the method of treating cognitive disorders of the instant invention are those of formula

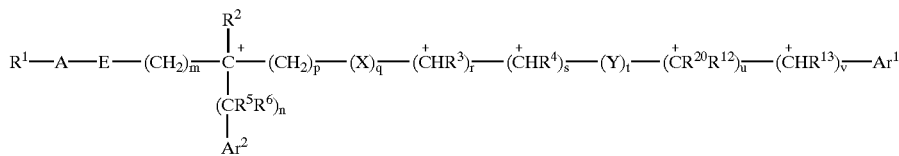

or a pharmaceutically acceptable salt thereof wherein:
$R^1$ is a cyclo or polycycloalkyl hydrocarbon or mono- or polyheterocyclic moiety wherein the hetero atom(s) can be N, O, and/or S, of from 3 to 12 carbon atoms with from 0 to 4 substituents each independently selected from a straight or branched alkyl of from 1 to 6 carbon atoms, halogen, CN, OR*, SR*, $CO_2R$*, $CF_3$, $NR^5R^6$, or $(CH_2)_nOR^5$ wherein R*, $R^5$, and $R^6$ are each independently hydrogen or a straight or branched alkyl of from 1 to about 6 carbon atoms;

m, n, p, q, r, s, t, u, and v are each independently an integer of from 0 to 6 with the proviso that q, r, and s are not all 1 when m, p, t, u, and v are all 0 except when X is not $CONR^9$ or A–E is not $(CH_2)_nCONH$—, —$SO_2NH$—, —$S(O)NH$—, —$NHCONH$, —$(CH_2)_n$—$OCO$—$NH$—, —$SCONH$—, —$O(CH_2)_nCO$— or —$HC$=$CHCONH$— wherein n is as above, A is a bond,
O,
S,
NR*,
—$(CH_2)_nCO$—Z,
—$SO_2$—Z,
—$SO$—Z,
—$NHCO$—Z, —(CH$_2$)$_{\overline{n}}$—O$\overset{\underset{\parallel}{O}}{C}$—Z, —$SCO$—Z,
—$O$—$(CH_2)_nCO$—Z,
—$HC$=$CHCO$—Z,
wherein Z is a bond, oxygen, sulphur, or —NR*—
wherein R* is as defined above;

E is a bond,
an amino acid residue,
—$(CHR^3)_r$—,
—$(CHR^3)_r$—$(CHR^4)_s$—,
—$CONH$—,
—$NHCO$—,
—$OCO$—,
—$COO$—,
—$CH_2N(R^3)$—,
—$CH_2O$—,
—$CH_2S$—,
—$C$=$C$—, —$\overset{\underset{\parallel}{S}}{C}$—$NR^3$,

—$SO_2NR^3$—,
—$NR^3SO_2$—,
—$NHCONH$—

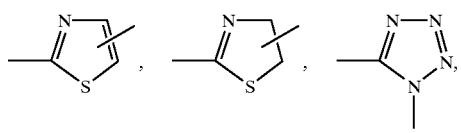

-continued

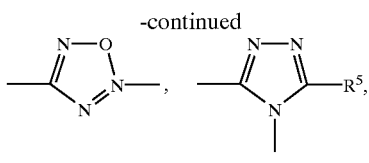

wherein
r and s are independently as defined above and $R^3$ and $R^4$ are as defined above;

$R^2$ and $R^{20}$ are each independently hydrogen, a straight or branched alkyl of from 1 to 6 carbon atoms, —HC=CH$_2$, —C≡CH, —(CH$_2$)$_n$CH=CH$_2$, —(CH$_2$)$_n$C≡CH, —(CH$_2$)$_n$Ar$^1$, —(CH$_2$)$_n$Ar$^2$, —(CH$_2$)$_n$OR*, —(CH$_2$)$_n$OAr, —(CH$_2$)$_n$CO$_2$R*, —(CH$_2$)$_n$NR$^5$R$^6$ wherein n,, R*, R$^5$, and R$^6$ are as defined above, and Ar$^1$ and Ar$^2$ are as defined below;

X and Y are each independently:
—CONH—,
—CONR$^9$,
—NHCO—,
—OCO—,
—COO—,
—CH$_2$N(R$^3$)—,
—CH$_2$O—,
—CH$_2$S—,
—OCH$_2$—,
—SCH$_2$—,
—C=C—,

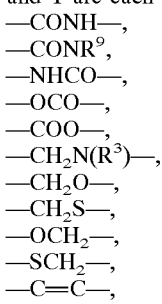

—SO$_2$NR$^3$—,
—NR$^3$SO$_2$—,
—NHCONH—,
—CH(OR*)CH$_2$—,
—COCH$_2$—,
—CH$_2$CO—,
—NR$^3$CH$_2$—,

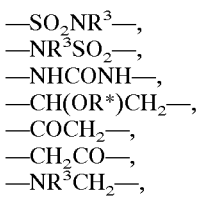

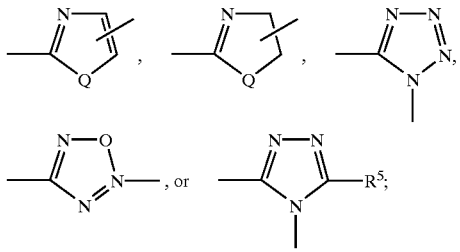

wherein
Q is O, S, or NR$^9$;
$R^3$ and $R^4$ are each independently the same as $R^2$ or —(CH$_2$)$_{n'}$—B—D wherein n' is an integer of from 0 to 3;
B is a bond,
—OCO(CH$_2$)$_n$—,
—O(CH$_2$)$_n$—,
—NHCO(CH$_2$)$_n$—,
—CONH(CH$_2$)$_n$—,
—NHCOCH=CH—,
—COO(CH$_2$)$_n$—,
—CO(CH$_2$)$_n$—,
—SO(CH$_2$)$_n$—,
—S(CH$_2$)$_n$—,
—SO$_2$(CH$_2$)$_n$—,

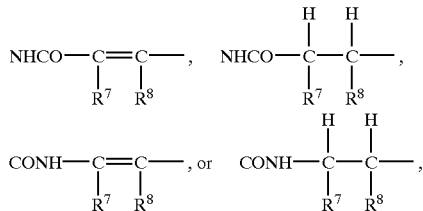

wherein $R^7$ and $R^8$ are each independently selected from hydrogen and $R^2$ or together form a ring (CH$_2$)$_m$ wherein m is an integer of from 1 to 5, D is
—COOR*,
—CH$_2$OR*,
—CHR$^2$OR*,
—CH$_2$SR*,
—CHR$^2$SR*,
—CONR$^5$R$^6$,
—CN,
—NR$^5$R$^6$,
—OH,
—H, and acid replacements such as tetrazole;

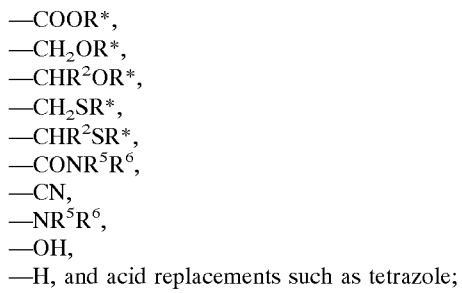

$R^{10}$ is OH, NH$_2$, CH$_3$, or Cl 1, 2, 4 oxadiazole

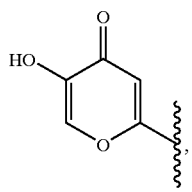

—PO$_3$H$_2$

HS—

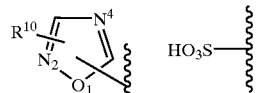

, $R^{11}$ is CN, CO$_2$H, or CF$_3$

-continued

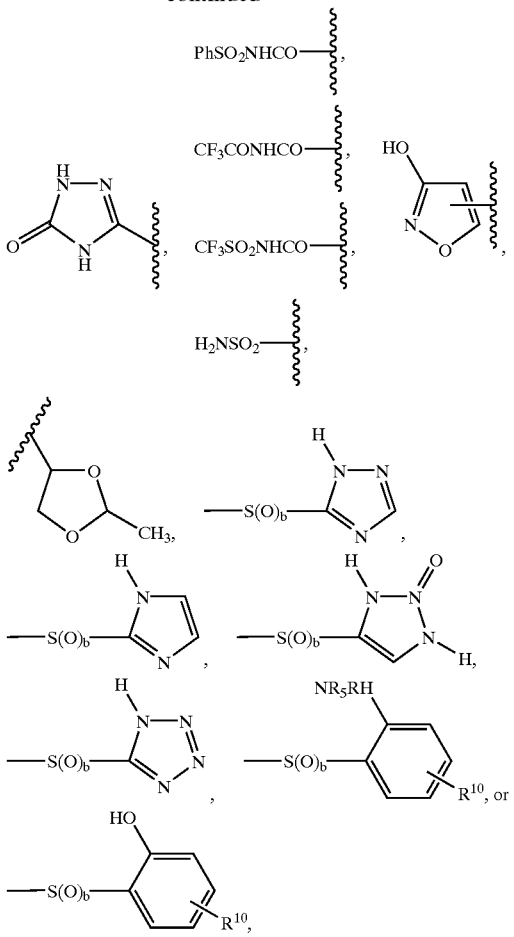

wherein b is an integer of from 0 to 2, wherein R*, $R^2$, $R^5$, and $R^6$ are as defined above; $R^9$ is H, or a straight or branched alkyl of from one to six carbon atoms, —$(CH_2)_nCO_2R*$, $(CH_2)_nOAr'$, $(CH_2)_nAr'$, $(CH_2)_nNR^5R^6$, wherein n, R*, $R^5$, and $R^6$ are as defined above or taken from $R^3$ and Ar is taken from $Ar^1$ as defined below;

$R^{12}$ and $R^{13}$ are each independently hydrogen or taken together form a double bond, or are —$(CH_2)_n$—B—D as defined above; and $Ar^1$ and $Ar^2$ are each independently a mono- or polycyclic unsubstituted or substituted carbo- or heterocyclic aromatic or carbo- or heteroaromatic moiety.

Especially useful are compounds selected from:

Carbamic acid, [2-[[1-(hydroxymethyl)-2-phenylethyl]amino]-1-(1H-indol-3-ylmethyl)ethyl]-, tricyclo[3.3.1.1$^{3,7}$]dec-2-yl ester, [S-(R*,S*)]-, Carbamic acid, [2-[[1-(hydroxymethyl)-2-phenylethyl]amino]-1-(1H-indol-3-ylmethyl)ethyl-, tricyclo[3.3.1.1$^{3,7}$]dec-2-yl ester, [S-(R*,R*)]-, Tricyclo[3.3.1.1$^{3,7}$]dec-2-yl[1-[[[1-hydroxymethyl)-2-phenylethyl)carbonyl]amino]-2-(1H-indol-3-yl)ethyl]carbamate, Carbamic acid, [2-[(2-hydroxy-2-phenylethyl)amino]-1-(1H-indol-3-ylmethyl)-1-methylethyl]-, tricyclo[3.3.1.1$^{3,7}$]dec-2-yl ester (hydroxy center is RS, other center is R), Carbamic acid, [2-[[1-(hydroxymethyl)-2-phenylethyl]amino]-1-(1H-indol-3-ylmethyl)-1-methylethyl]-, tricyclo[3.3.1.1$^{3,7}$]dec-2-yl ester, [R-(R*,S*)]-, 4-methylbenzenesulfonate (1:1) (salt), Benzenepropanol,β-[[2-(1H-indol-3-yl)-2-[[(tricyclo[3.3.1.1$^{3,7}$]dec-2-yloxy)carbonyl]amino]propyl]amino]-, acetate (ester), [R-(R*,S*)]-, 4-methylbenzenesulfonate (1:1) (salt), Carbamic acid, [[2-[acetyl[1-(hydroxymethyl)-2-phenylethyl]amino]-1-(1H-indol-3-ylmethyl)-1-methylethyl]-, tricyclo[3.3.1.1$^{3,7}$]dec-2-yl ester, [R-(R*,S*)]-, 5,13-Dioxa-2,8-diazatetradec-10-enoic acid, 3-(1H-indol-3-ylmethyl)-3-methyl-4,9,12-trioxo-7-phenyl-, tricyclo[3.3.1.1$^{3,7}$]dec-2-yl ester, [S-(R*,S*)]-, 5,13-Dioxa-2,8-diazatetradecanoic acid, 3-(1H-indol-3-ylmethyl)-3-methyl-4,9,12-trioxo-7-phenyl-, tricyclo[3.3.1.1$^{3,7}$]dec-2-yl ester, [R-(R*,R*)]-, Carbamic acid, [1-(1H-indol-3-ylmethyl)-1-methyl-2-[(1-oxo-4-phenylbutyl)amino]ethyl]-, tricyclo[3.3.1.1$^{3,7}$]dec-2-yl ester (R)-, Carbamic acid, [2-(benzoylamino)-1-(1H-indol-3-ylmethyl)-1-methylethyl]-, tricyclo[3.3.1.1$^{3,7}$]-dec-2-yl ester, (R)-, Carbamic acid, [1-(1H-indol-3-ylmethyl)-1-methyl-2-[(1-oxo-3-phenylpropyl)amino]ethyl]-, tricyclo[3.3.1.1$^{3,7}$]dec-2-yl ester, (R)-, Carbamic acid, [1-(1H-indol-3-ylmethyl)-1-methyl-2-[(2-phenylacetyl)amino]ethyl]-, tricyclo-[3.3.1.1$^{3,7}$]dec-2-yl ester, (R)-, Carbamic acid, [2-[[3-[[1-(hydroxymethyl)-2-phenylethyl]amino]-3-oxopropyl]amino]-1-(1H-indol-3-ylmethyl)-1-methyl-2-oxoethyl]-, [R,(R*,S*)]-, Carbamic acid, [1-(1H-indol-3-ylmethyl)-2-[[3-[[1-(hydroxymethyl)-2-phenylethyl]amino]-3-oxopropyl]amino]-1-methyl-2-oxoethyl]-, tricyclo-[3.3.1.1$^{3,7}$]dec-2-yl ester, [S-(R*,R*)]-, D-Phenylalaninamide, α-methyl-N-[(tricyclo-[3.3.1.1$^{3,7}$]dec-2-yloxy)carbonyl]-D-tryptophyl-β-alanyl-, L-Phenylalaninamide, α-methyl-N-[(tricyclo-[3.3.1.1$^{3,7}$]dec-2-yloxy)carbonyl]-D-tryptophyl-β-alanyl-, L-Phenylalaninamide, α-methyl-N-[(tricyclo-[3.3.1.1$^{3,7}$]dec-2-yloxy)carbonyl]-L-tryptophyl-β-alanyl-, D-Phenylalaninamide, α-methyl-N-[(tricyclo-[3.3.1.1$^{3,7}$]dec-2-yloxy) carbonyl]-L-tryptophyl-β-alanyl-, 12-Oxa-2,5,9-triazatridecanoic acid, 3-(1H-indol-3-ylmethyl)-3-methyl-4,8,11-trioxo-10-(phenylmethyl)-, tricyclo[3.3.1.1$^{3,7}$]dec-2-yl ester, [R,(R*,R*)]-, L-Phenylalanine, N-[N-[α-methyl-N-[(tricyclo-[3.3.1.1$^{3,7}$]dec-2-yloxy)carbonyl]-D-tryptophyl]-β-alanyl]-, phenylmethyl ester, Propanoic acid, 2-[[3-[[3-(1H-indol-3-yl)-2-methyl-1-oxo-2-[[(tricyclo[3.3.1.1$^{3,7}$]dec-2-yloxy)carbonyl]amino]propyl]amino]-1-oxopropyl]amino]-3-phenyl-, phenylmethyl ester, [S-(R*,R*)]-, D-Phenylalanine, N-[N-[α-methyl-N-[(tricyclo-[3.3.1.1$^{3,7}$]dec-2-yloxy)carbonyl]-D-tryptophyl]-β-alanyl]-, L-Phenylalanine, N-[N-[α-methyl-N-[(tricyclo-[3.3.1.1$^{3,7}$]dec-2-yloxy)carbonyl]-D-tryptophyl]-β-alanyl]-, L-Phenylalanine, N-[N-[α-methyl-N-[(tricyclo-[3.3.1.1$^{3,7}$]dec-2-yloxy)carbonyl]-L-tryptophyl]-β-alanyl]-, Benzenepropanoic acid, α-[[3-[[3-[(1H-indol-3-yl)-2-methyl-1-oxo-2-[[(tricyclo[3.3.1.1$^{3,7}$]dec-2-yloxy)carbonyl]amino]propyl]amino]-1-oxopropyl]amino]-, [S-(R*,S*)]-, Glycine, N-[2-methyl-N-[(tricyclo[3.3.1.1$^{3,7}$]dec-2-yloxy)carbonyl]-D-tryptophyl]-, phenylmethyl ester, Carbamic acid, [3-(1H-indol-3-ylmethyl)-2,5-dioxo-1-(2-phenylethyl)-3-pyrrolidinyl]-, tricyclo[3.3.1.1$^{3,7}$]dec-2-yl ester, (±)-, Carbamic acid, [1-(1H-imidazol-4-ylmethyl)-1-methyl-2-oxo-2-[(2-phenylethyl)amino]ethyl]-, 1,1-dimethylethyl ester, (±)-, Carbamic acid, [3-(1H-indol-3-yl)-1-methyl-1-[[(2-phenylethyl)amino]carbonyl]propyl]-, tricyclo-[3.3.1.1$^{3,7}$]dec-2-yl ester, (±)-, Carbamic acid, [1-[[[1-hydroxymethyl)-2-phenylethyl]amino)carbonyl]-3-(1H-indol-3-yl)-1-methylpropyl]-, tricyclo[3.3.1.1$^{3,7}$]dec-2-yl ester (hydroxymethyl center is S, other center is RS), 13-Oxa-2,5,β-triazatetradec-10-enoic acid, 3-[2-(1H-indol-3-yl)ethyl]-3-methyl-4,5,12-trioxo-7-phenyl-, tricyclo [3.3.1.1$^{3,7}$]dec-2-yl ester [TRP center is R/S mixture, other center is R], L-Phenylalaninamide, N-[[(1,1-dimethylethoxy)-carbonyl]-α-methyl]-L-tryptophyl]-L-methionyl-L-α-aspartyl-, Glycine, N-[2-methyl-N-[(tricyclo-[3.3.1.1$^{3,7}$]dec-2-yloxy) carbonyl]-D-tryptophyl]-L-phenylalanyl-, Carbamic acid, [1-[[[1-(hydroxymethyl)-2-phenylethyl] amino]carbonyl]-2-(1H-indol-3-yl)propyl]-, tricyclo [3.3.1.1$^{3,7}$]dec-2-yl ester (hydroxymethyl center S, other centers RS), 2,4-Heptadienoic acid, 6-[[3-(1H-indol-3-yl)-2-methyl-1-oxo-2-[[(tricyclo[3.3.1.1$^{3,7}$]dec-2-yloxy)-carbonyl] amino]propyl]amino]-7-phenyl-, [R,R*,S*-(E,E)]]-, Glycine, N-[2-methyl-N-[(tricyclo-[3.3.1.1$^{3,7}$])dec-2-yloxy) carbonyl]-D-tryptophyl]-, phenylmethyl ester, and Tricyclo[3.3.1.1$^{3,7}$]dec-2-yl-R-(R*,S*)]-[1-[4,5-dihydro-4-(phenylmethyl)-2-thiazolyl]-2-(1H-indol-3-yl)-1-methylethyl]carbamate.

Other compounds useful in the method of treating cognitive disorders of the instant invention are those of formula

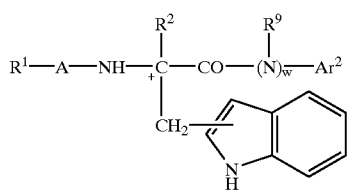

IV or a pharmaceutically acceptable salt thereof wherein:

$R^1$ is a cyclo- or polycycloalkyl hydrocarbon of from three to twelve carbon atoms with from zero to four substituents, each independently selected from the group consisting of: a straight or branched alkyl of from one to six carbon atoms, halogen, CN, OR*, SR*, $CO_2R^*$, $CF_3$, $NR^5R^6$, or —$(CH_2)_nOR^5$, wherein R* is hydrogen, straight or branched alkyl of from one to six carbon atoms, $R^5$ and $R^6$ are each independently hydrogen or alkyl of from one to six carbon atoms; and n is an integer from zero to six;

A is —$(CH_2)_nCO$—, —$SO_2$—, —SO—, —NHCO—,

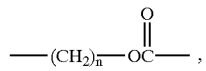

—SCO—, —O—$(CH_2)_nCO$— or —HC=CHCO— wherein n is an integer from zero to six;

$R^2$ is a straight or branched alkyl of from one to six carbon atoms, —HC=$CH_2$, —C≡—CH, —$(CH_2)_n$—CH=$CH_2$, —$(CH_2)_nC$≡CH, —$(CH_2)_nAr$, —$(CH_2)_nOR^*$, —$(CH_2)_nOAr$, —$(CH_2)_nCO_2R^*$, —$(CH_2)_nNR^5R^6$ wherein n, R, $R^5$, and $R^6$ are as defined above and Ar is a mono or polycyclic unsubstituted or substituted carbo- or heterocyclic aromatic or hydroaromatic moiety;

$R^9$ is H, or a straight or branched alkyl of from one to six carbon atoms, —$(CH_2)_nCO_2R^*$, $(CH_2)_nOAr'$, $(CH_2)_nAr'$, $(CH_2)_nNR^5R^6$, wherein n, R*, $R^5$, and $R^6$ are as defined above or taken from $R^3$ and Ar' is taken independently from Ar and w is zero or 1;

$Ar^2$ is

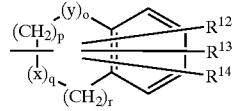

wherein x and y are each independently O, S, N, $CH_2$, —$CHR^{12}$, —$NR^{12}$—, —$NR^{12}CO$—, —C=N—, —C=C—, or —(C=O)— or a bond; o, p, q, and r are each independently an integer of from 0 to 3, provided that when o, p, q, and r are all simultaneously zero, $Ar^2$ becomes

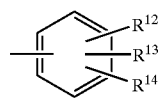

$R^{12}$, $R^{13}$, and $R^{14}$ are each independently halogen, $R^2$ as is defined above, —$(CH_2)_g$—B—D wherein g is an integer of from 0 to 6 wherein B is a bond, —OCO $(CH_2)_n$—,
—O$(CH_2)_n$—,
—NHCO $(CH_2)_n$—,
—CONH$(CH_2)_n$—,
—NHCOCH=CH—,
—COO$(CH_2)_n$—,
—CO$(CH_2)_n$—,
—S$(CH_2)_n$—,
—SO$(CH_2)_n$—,
—$SO_2(CH_2)_n$—,

NHCO—C=C—,
      |  |
      $R^7$ $R^{8'}$

CONH—C=C—,
      |  |
      $R^7$ $R^8$

H  H
        |  |
NHCO—C—C,
      |  |
      $R^7$ $R^8$

H  H
        |  |
CONHC—C—,
      |  |
      $R^7$ $R^8$

—$NHSO_2$—$(CH_2)_n$—, or
—$SO_2NH$—$(CH_2)_n$—,
wherein $R^7$ and $R^8$ are independently selected from hydrogen and $R^2$, or together form a ring $(CH_2)_m$ wherein m is an integer of from 1 to 5 and n is as defined above;

D is
—COOR*,
—$CH_2OR^*$,
—$CHR^2OR^*$,
—$CH_2SR^*$,
—$CHR^2SR^*$,

—CONR⁵R⁶,
—CN,
—NR⁵R⁶,
—OH,
—H, and acid replacements such as tetrazole,

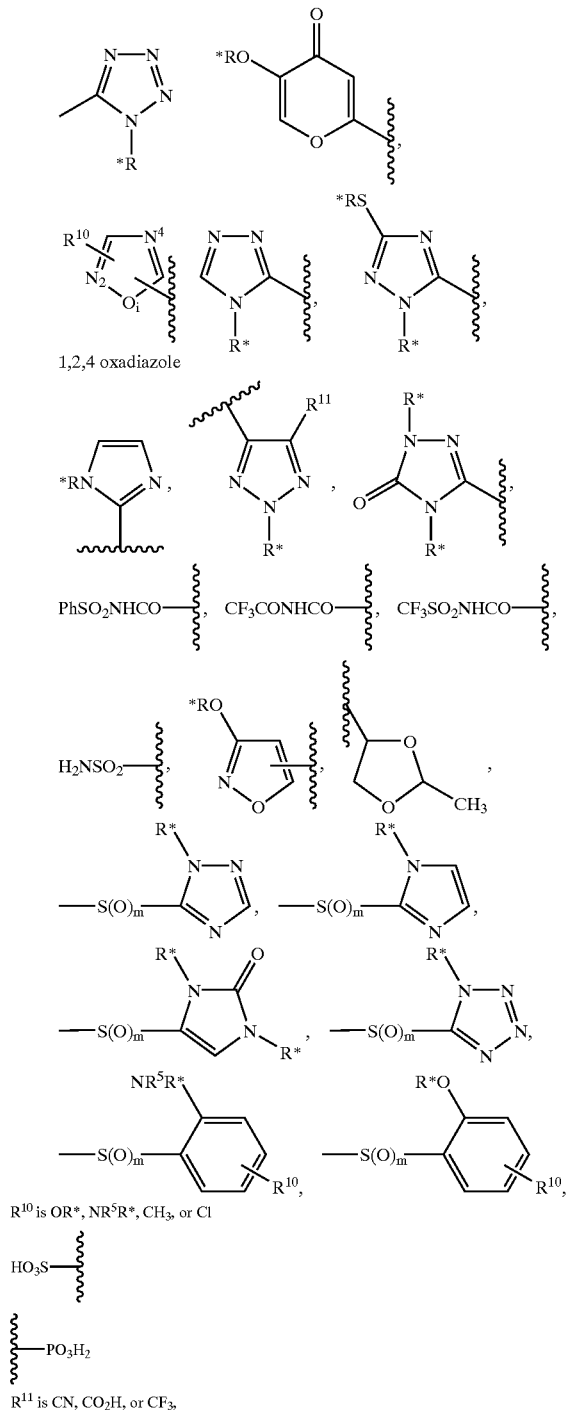

1,2,4 oxadiazole $R^{10}$ is OR*, NR⁵R*, CH₃, or Cl $R^{11}$ is CN, CO₂H, or CF₃, wherein s is an integer of from 0 to 2
wherein R*, $R^2$, $R^5$, and $R^6$ are as defined above.
Especially useful are compounds selected from:

carbamic acid, [2-[(2,3-dihydro-2-hydroxy-1H-inden-1-yl) amino]-1-(1H-indol-3-ylmethyl)-1-methyl-2-oxoethyl]-, 1,7,7-trimethylbicyclo-[2.2.1]hept-2-yl ester (bicyclo ring is 1S-endo (+-isomer), trp center is D, indene ring centers are unknown), carbamic acid, [2-[(2,3-dihydro-1-hydroxy-1H-inden-2-yl) amino]-1-1H-indol-3-ylmethyl)-2-methyl-2-oxoethyl]-, 1,7,7-trimethylbicyclo-[2.2.1]hept-2-yl ester, [1S*[1α,2β [S-(trans)],4β]]-(Bicyclo system is 1S-endo), carbamic acid, [2-[(2,3-dihydro-1-hydroxy-1H-inden-2-yl) amino]-1-(1H-indol-3-ylmethyl)-1-methyl-2-oxoethyl]-, 1,7,7-trimethylbicyclo-[2.2.1]hept-2-yl ester, [1S-[1α,2β [S*(1S*,2S*)],4α]]-[Bicyclo system is 1S-endo, all other centers are R], carbamic acid, [1-(1H-indol-3-ylmethyl)-1-methyl-2-oxo-2- [(1,2,3,4-tetrahydro-1-oxo-2-naphthalenyl)amino]ethyl]-, 1,7,7-trimethylbicyclo[2.2.1]hept-2-yl ester (Bicyclo system 1S-endo; TRP center R; naphthyl center (−) or (+)), (Isomer II), carbamic acid, [1-(1H-indol-3-ylmethyl)-1-methyl-2-oxo-2- [(1-2,3,4-tetrahydro-1-oxo-2-naphthalenyl)amino] ethyl]-, 1,7,7-trimethylbicyclo[2.2.1.1]hept-2-yl ester (Bicyclo system 1S-endo; TRP center R; naphthyl center (+) or (−)), (Isomer I), carbamic acid, [1-(1H-indol-3-ylmethyl)-1-methyl-2-oxo-2- [(1,2,3,4-tetrahydro-1-naphthalenyl)amino]ethyl]-, tricyclo[3.3.1.1³,⁷]-dec-2-yl ester, (±)-, carbamic acid, [1-1H-indol-3-ylmethyl)-1-methyl-2-oxo-2- [(1,2,3,4-tetrahydro-2-naphthalenyl)amino]ethyl]-, tricyclo[3.3.1.1³,⁷]-dec-2-yl ester, (±)-, carbamic acid, [1-(1H-indol-3-ylmethyl)-1-methyl-2-oxo-2- (1,2,3,4-tetrahydro-2-isoquinolinyl)ethyl)]-, tricyclo [3.3.1.1³,⁷]-dec-2-yl ester, (R)-, 4-[[1,2,3,4-tetrahydro-2-[[3-(1H-indol-3-yl)-2-methyl-1-oxo-2-[[(tricyclo[3.3.1.1³,⁷]dec-2-yloxy)carbonyl]amino] propyl]amino]-1-naphthalenyl]amino]-4-oxobutanoate tricyclo[3.3.1.1³,⁷]dec-2-yl-[2-[(1-azido-1,2,3,4-tetrahydro-2-naphthalenyl)amino]-1(1H-indol-3-ylmethyl)-1-methyl-2-oxoethyl]carbamate, methyl 3-[[2-[[3-(1H-indol-3-yl)-2-methyl-1-oxo-2- [[(tricyclo[3.3.1.1³,⁷]dec-2-yloxy)carbonyl]amino] propyl]amino]-1,2,3,4-tetrahydro-1-naphthalenyl] amino]-3-oxopropanoate, methyl 3-[[2-[[3-(1H-indol-3-yl)-2-methyl-1-oxo-2- [[(tricyclo[3.3.1.1³,⁷]dec-2-yloxy)carbonyl]amino] propyl]amino]-1,2,3,4-tetrahydro-1-naphthalenyl] amino]-3-oxopropanoate, and methyl 1-[[1,2,3,4-tetrahydro-2-[[3-(1H-indol-3-yl)-2-methyl-1-oxo-2-[[(tricyclo[3.3.1.1³,⁷]dec-2-yloxy) carbonyl]amino]propyl]amino]-1-naphthalenyl]amino]-4-oxo-2-butanoate Other compounds useful in the method of treating cognitive disorders of the instant invention are those of formula

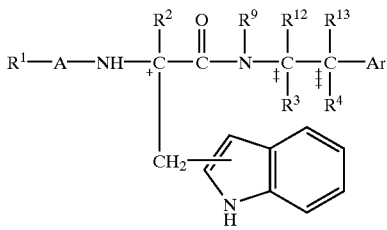

V or a pharmaceutically acceptable salt thereof wherein:
$R^1$ is a cycloalkyl or polycycloalkyl hydrocarbon of from three to twelve carbon atoms with from zero to four substituents each independently selected from the group consisting of a straight or branched alkyl of from one to about six carbon atoms, halogen, CN, OR*, SR*, CO$_2$R*, CF$_3$, NR$^5$R$^6$, and —(CH$_2$)$_n$OR$^5$ wherein R* is hydrogen, straight or branched alkyl of from one to six carbon atoms, —(CH$_2$)$_n$Ar, —COAr, —(CH$_2$)$_n$OCOAr, or —(CH$_2$)$_n$NR$^5$COAr and R* may also independently be R as defined below, and R must be present at least once in formula I, and R** is attached to formula I through a metabolically labile bond and can include

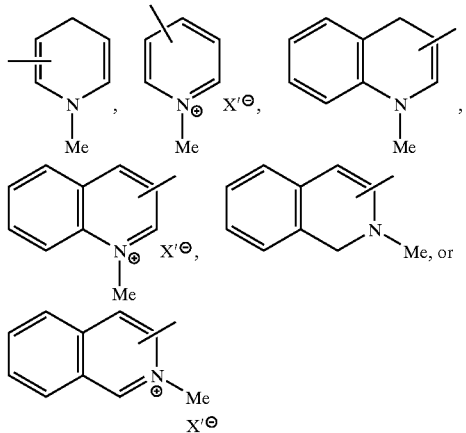

R$^5$ and R$^6$ are each independently hydrogen or alkyl of from one to about six carbon atoms and n is an integer from zero to six;

and, R** is —(CH$_2$)$_n$NR$^5$R$^6$, —(CH$_2$)$_n$—B—D* wherein D* is O—COR*, CO$_2$Ar$^2$, (CH$_2$)$_n$Ar$^2$, OCOAr$^2$, NR$^5$COAr$^2$, COAr$^2$, CO$_2$CH(R)—CO$_2$R*, CO$_2$—(CH$_2$)$_n$OCOR* where Ar$^2$ is independently taken from Ar, where m is as defined below, CONHCH(R)CO$_2$R* where R is a side chain of a biologically significant amino acid, R is hydrogen only when B is not a bond, —CO$_2$CH$_2$CH$_2$N$^+$(R*)$_3$X$^{1-}$ when X$^{1-}$ is a pharmaceutically acceptable counter anion, A is —(CH$_2$)$_n$CO—, —SO$_2$—, —S(=O)—, —NHCO—, —(CH)$_n$—C(=O)—,

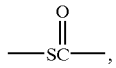

—O—(CH$_2$)$_n$CO— or —HC=CHCO— wherein n is an integer from zero to six;

R$^2$ is a straight or branched alkyl of from one to about six carbon atoms, —HC=CH$_2$, —C≡CH, —(CH$_2$)$_n$—CH=CH$_2$, —(CH$_2$)$_n$C≡CH, —(CH$_2$)$_n$Ar, —(CH$_2$)$_n$OR*, —(CH$_2$)$_n$OAr, —(CH$_2$)$_n$CO$_2$R*, or —(CH$_2$)$_n$NR$^5$R$^6$ wherein n, R*, R$^5$ and R$^6$ are as defined above and Ar is as defined below;

R$^3$ and R$^4$ are each independently selected from hydrogen, R$^2$ and —(CH$_2$)$_{n'}$—B—D wherein:
n' is an integer of from zero to three; B is a bond,
—OCO(CH$_2$)$_n$—,
—O(CH$_2$)$_n$—,
—NHCO (CH$_2$)$_n$—,
—CONH (CH$_2$)$_n$—,
—NHCOCH=CH—,
—COO(CH$_2$)$_n$—,
—CO(CH$_2$)$_n$—,
—S—(CH$_2$)$_n$—,
—S(=O)—(CH$_2$)$_n$—,
—SO$_2$—(CH$_2$)$_n$—,
—NHSO$_2$—(CH$_2$)$_n$—,
—SO$_2$NH—(CH$_2$)$_n$—,

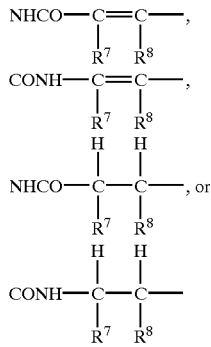

wherein R$^7$ and R$^8$ are each independently selected from hydrogen and R$^2$ or together form a ring (CH$_2$)$_m$ wherein m is an integer of from 1 to 5 and n is as defined above;

D is hydrogen,
—COOR*,
—CH$_2$NR$^5$R*,
—CHR$^2$NR$^5$R*,
—CH$_2$OR*,
—CHR$^2$OR*,
—CH$_2$SR*,
—CHR$_2$SR*,
—CONR$^5$R$^6$,
—CONR$^5$R*,
an acid replacement selected from

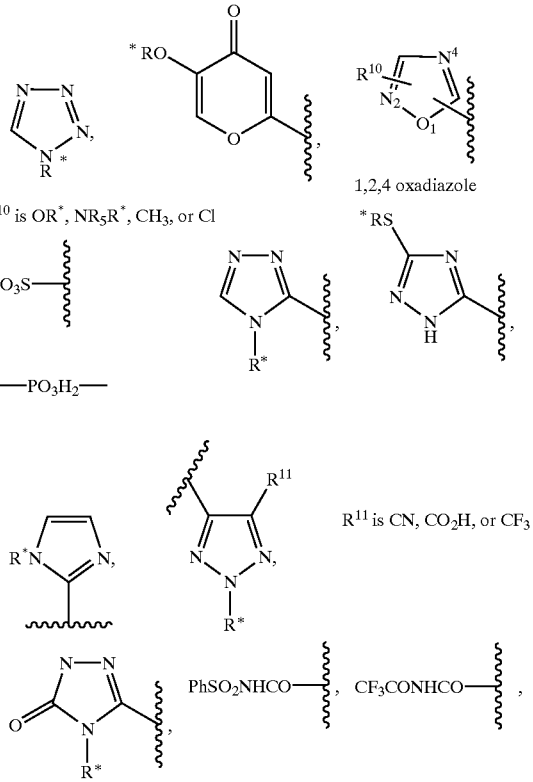

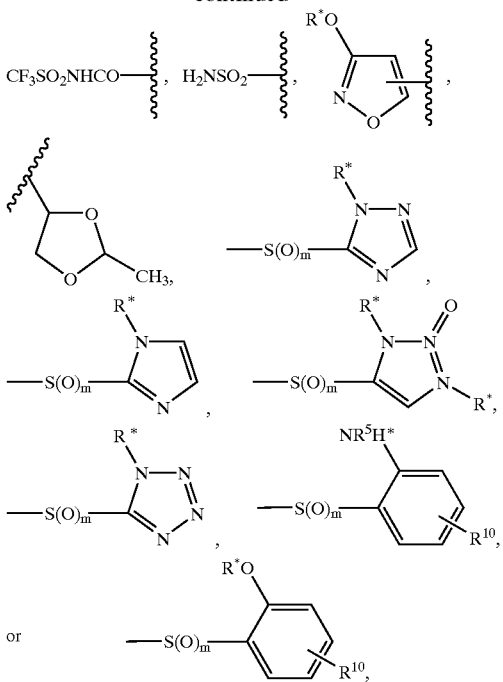

wherein m is an integer of from 0 to 2 wherein R*, $R^2$, $R^5$, and $R^6$ are as defined above;

$R^9$ is hydrogen or a straight or branched alkyl of from one to about six carbon atoms, —$(CH_2)_nCO_2R^*$, —$(CH_2)_nNR^5R^*$, wherein n, R*, and $R^5$ are as defined above or taken from $R^3$;

$R^{12}$ and $R^{13}$ are each independently hydrogen or are each independently taken with $R^3$ and $R^4$, respectively, to form a moiety doubly bonded to the carbon atom; and Ar is a mono- or polycyclic unsubstituted or substituted carbo- or heteroaromatic or carbo- or heterohydroaromatic moiety.

Especially useful are compounds selected from:

L-Aspartic acid, N-[N-[α-methyl-N-[(tricyclo[3.3.1.1$^{3,7}$]-dec-2-yloxy)carbonyl]-D-tryptophyl]-L-phenylalanyl]-, L-Glutamic acid, N-[N-[α-methyl-N-[(tricyclo[3.3.1.1$^{3,7}$]-dec-2-yloxy)carbonyl]-D-tryptophyl]-L-phenylalanyl]-, L-Glutamic acid, N-[N-[α-methyl-N-[(tricyclo-[3.3.1.1$^{3,7}$]-dec-2-yloxy)carbonyl]-D-tryptophyl]-L-phenylalanyl]-, dimethyl ester, 2-[[3-(1H-Indol-3-yl)-2-methyl-1-oxo-2[[tricyclo-[3.3.1.1$^{3,7}$]dec-2-yloxy)carbonyl]amino]propyl]-amino]-3-phenylpropyl[R-(R*,S*)]-1,4-dihydro-1-methyl-3-pyridinecarboxylate, 2-[[3-(1H-indol-3-yl)-2-methyl-1-oxo-2[[(tricyclo-[3.3.1.1$^{3,7}$]dec-2-yloxy)carbonyl]amino]propyl]-amino]-3-phenylpropyl[R-(R*,S*)]-trigonelline iodide 2-[3-[3-(1H-indol-3-yl)-2-methyl-1-oxo-2-[[tricyclo-[3.3.1.1$^{3,7}$]dec-2-yloxy)carbonyl]amino]propyl]amino]-3-phenylpropyl[R-(R*,S*)]-3-pyridinecarboxylate, butanoic acid, 4-[[2-[[3-(1H-indol-3-yl)-2-methyl-1-oxo-2-[[(tricyclo[3.3.1.1$^{3,7}$]dec-2-yloxy)carbonyl]amino] propyl]amino]-1-phenylethyl]amino]-4-oxo-, (2,2-dimethyl-1-oxopropoxy)methyl ester, [R-(R*,R*)]-, butanoic acid, 4-[[2-[[3-(1H-indol-3-yl)-2-methyl-1-oxo-2-[[(tricyclo[3.3.1.1$^{3,7}$]dec-2-yloxy)carbonyl]amino] propyl]amino]ethyl]amino]-4-oxo-, chloromethyl ester, [R-(R*,R*)]-, Pentanedioic acid, [4-[[2-[[3-(1H-indol-3-yl)-2-methyl-1-oxo-2-[[(tricyclo[3.3.1.1$^{3,7}$]dec-2-yloxy)carbonyl]amino] propyl]amino]-1-phenylethyl]amino]-1,4-dioxobutoxy] methyl ester, [R-(R*,R*)]-, butanoic acid, 4-[[2-[[3-(1H-indol-3-yl)-2-methyl-1-oxo-2-[[(tricyclo[3.3.1.1$^{3,7}$]dec-2-yloxy)carbonyl]amino] propyl]amino]-1-phenylethyl]amino]-4-oxo-2,3-dihydro-1H-inden-5-yl ester, [R-(R*,R*)]-, and butanoic acid, 4-[[2-[[3-(1H-indol-3-yl)-2-methyl-1-oxo-2-[[(tricyclo[3.3.1.1$^{3,7}$]dec-2-yloxy)carbonyl]amino] propyl]amino]-1-phenylethyl]amino]-4-oxo-, [R-(R*, R*)]-.

Other compounds useful in the method of treating cognitive disorders of the instant invention are those of formula

VI

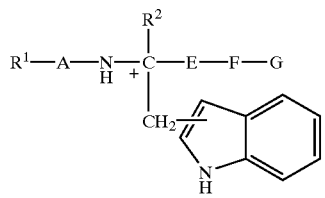

or a pharmaceutically acceptable salt thereof wherein:

$R^1$ is a cyclo- or polycycloalkyl hydrocarbon of from three to twelve carbon atoms with from zero to four substituents, each independently selected from the group consisting of: a straight or branched alkyl of from one to six carbon atoms, halogen, CN, OR*, SR*, $CO_2R^*$, $CF_3$, $NR^5R^6$, or —$(CH_2)_nOR^5$, wherein R* is hydrogen, straight or branched alkyl of from one to six carbon atoms, $R^5$ and $R^6$ are each independently hydrogen or alkyl of from one to six carbon atoms; and n is an integer from zero to six;

A is —$(CH_2)_nCO$—, —$SO_2$—, —SO—, —NHCO—,

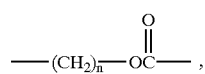

—SCO—, —O—$(CH_2)_nCO$— or —HC=CHCO— wherein n is an integer from zero to six;

$R^2$ is a straight or branched alkyl of from one to six carbon atoms, —HC=$CH_2$, —C≡CH, —$CH_2$—CH=$CH_2$, —$(CH_2)_nC≡CH$, —$(CH_2)_nAr$, —$(CH_2)_nOR^*$, —$(CH_2)_nOAr$, —$(CH_2)_nCO_2R^*$, —$(CH_2)_nNR^5R^6$ wherein n, R' $R^5$ and $R^6$ are as defined above and Ar is a mono- or polycyclic unsubstituted or substituted carbo- or heterocyclic aromatic or hydroaromatic moiety;

E is —CONH—, —NHCO—, —OCO—, —COO—, —$(CH_2)_mNR^3$—, —$(CH_2)_mO$—, —$(CH_2)_mS$—, —C=C,

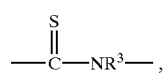

—$SO_2NR^3$—, —$NR^3SO_2$—, —NHCONH—, —$CH_2CO$—, —$COCH_2$—, —$(CH_2)_mNHCO$—, —$(CH_2)_m$ CONH— wherein m is an integer of from 1–5,

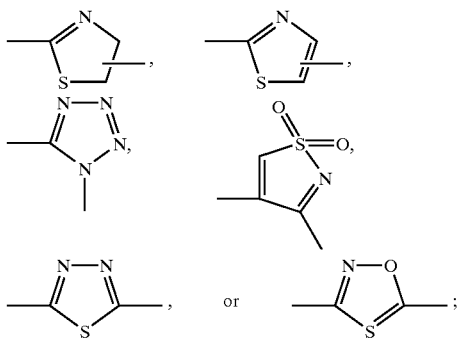

F is a bond, —CH(R)CO— wherein R is —(CHR³)ₚ—(CHR⁴)_q-D, wherein D is as defined below, wherein p and q are each independently 0, 1, or 2 and wherein F is a desamino biologically significant amino acid, excluding Tyr, Phe, Trp, His;

R³ and R⁴ are each independently selected from R² and —(CH₂)_{n'}—B—D wherein:

n' is an integer of from zero to three;

B is a bond,
—OCO(CH₂)ₙ—,
—O(CH₂)ₙ—,
—NHCO(CH₂)ₙ—,
—CONH(CH₂)ₙ—,
—NHCOCH=CH—,
—COO(CH₂)ₙ—,
—CO(CH₂)ₙ—,
—S—(CH₂)ₙ—,
—S(=O)—(CH₂)ₙ—,
—SO₂—(CH₂)ₙ—,
—NHSO₂—(CH₂)ₙ—,
—SO₂NH—(CH₂)ₙ—,

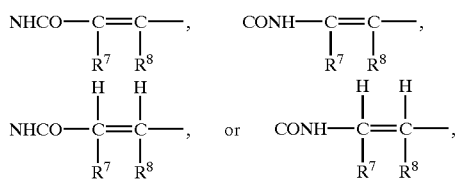

wherein R⁷ and R⁸ are independently selected from hydrogen and R² or together form a ring (CH₂)_m wherein m is an integer of from 1 to 5 and n is as defined above;

D is —COOR*,
—CH₂OR
—CHR²OR*r
—CH₂SR*,
—CHR²SR*,
—CONR⁵R⁶,
—CN,
—NR⁵R⁶r
—OH,
—H or an acid replacement such as tetrazole, or

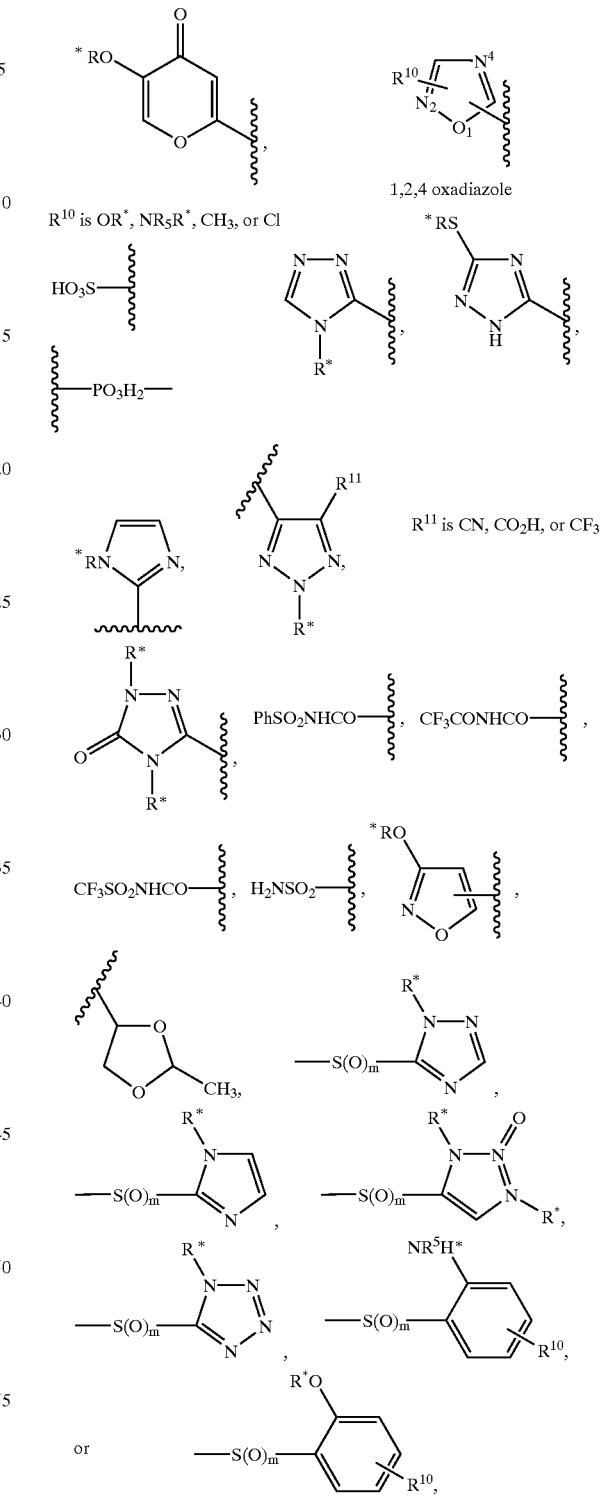

wherein s is an integer of from 0 to 2,
wherein R*, R², R⁵, and R⁶ are as defined above and
G is R³ as defined above, and
G cannot be hydrogen when F is a bond.
Especially useful are compounds selected from:

(R)-N-[3-(1H-indol-3-yl)-2-methyl-1-oxo-2-[[(tricyclo[3.3.1.1$^{3,7}$]dec-2-yloxy)carbonyl]amino]propyl]glycine,
(R)-4-[[3-(1H-indol-3-yl)-2-methyl-1-oxo-2-[[(tricyclo[3.3.1.1$^{3,7}$]dec-2-yloxy)carbonyl]amino]propyl]amino]butanoic acid,
Methyl (R)-4-[[3-(1H-indol-3-yl)-2-methyl-1-oxo-2-[[(tricyclo[3.3.1.1$^{3,7}$]dec-2-yloxy)carbonyl]amino]propyl]amino]butanoate,
Phenylmethyl (R)-3-[[3-(1H-indol-3-yl)-2-methyl-1-oxo-2-[[(tricyclo[3.3.1.1$^{3,7}$]dec-2-yloxy)carbonyl]amino]propyl]amino]propanoate,
Methyl N-[α-methyl-N-[(tricyclo[3.3.1.1$^{3,7}$]-dec-2-yloxy)carbonyl]-D-tryptophyl]-β-alanine,
Phenylmethyl N-[2-methyl-N-[(tricyclo-[3.3.1.1$^{3,7}$]-dec-2-yloxy)carbonyl]-D-tryptophyl]glycine,
N-[(α-methyl-N-[(tricyclo[3.3.1.1$^{3,7}$]dec-2-yloxy)carbonyl]-D-tryptophyl]-β-alanine,
Tricyclo[3.3.1.1$^{3,7}$]dec-2-yl [1S-[1R*(S*),2R*]]-[2-[[1-(hydroxy-methyl)-2-methyl-butyl]amino]-1-(1H-indol-3-ylmethyl)-1-methyl-2-oxoethyl]carbamate,
Tricyclo[3.3.1.1$^{3,7}$]dec-2-yl [R-(R*,S*)]-[2-[[1-(hydroxymethyl)-3-methylbutyl]amino]-1-(1H-indol-3-ylmethyl)-1-methyl-2-oxoethyl]carbamate,
Methyl N-[α-methyl-N-[(tricyclo-[3.3.1.1$^{3,7}$]dec-2-yloxy)carbonyl]-D-tryptophyl]-L-methionine,
N-[α-methyl-N-[(tricyclo[3.3.1.1$^{3,7}$]dec-2-yloxy)carbonyl]-D-tryptophyl]-L-methionine,
Methyl N-[N-[(α-methyl-N-[(tricyclo-[3.3.1.1$^{3,7}$]dec-2-yloxy)carbonyl]-D-tryptophyl]-L-methionyl]-β-alanine,
N-[S-methyl-N-[α-methyl-N-[(tricyclo[3.3.1.1$^{3,7}$]-dec-2-yloxy)carbonyl]-D-tryptophyl]-D-cysteinyl]-β-alanine,
S-methyl-N-[α-methyl-N-[(tricyclo[3.3.1.1$^{3,7}$]dec-2-yloxy)carbonyl]-D-tryptophyl-D-cysteine,
N-[α-Methyl-[N-[(tricyclo[3.3.1.1$^{3,7}$]dec-2-yloxy)carbonyl]-D-tryptophyl]-γ-(methylsulfinyl)-L-α-aminobutanoic acid, and
N-[α-methyl-N-[(tricyclo[3.3.1.1$^{3,7}$]dec-2-yloxy)carbonyl]-D-tryptophyl-γ-(methylsulfonyl)-L-α-aminobutanoic acid.

Other compounds useful in the method of treating cognitive disorders of the instant invention are those of formula VI

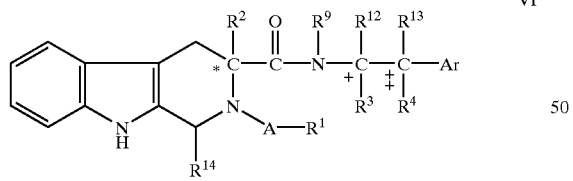

or a pharmaceutically acceptable salt thereof wherein:

$R^1$ is tert.-butyl, a cycloalkyl or polycycloalkyl hydrocarbon of from three to twelve carbon atoms with from zero to four substituents each independently selected from the group consisting of a straight or branched alkyl of from one to about six carbon atoms, halogen, CN, OR*, SR*, $CO_2R^*$, $CF_3$, $NR^5R^6$, and $—(CH_2)_nOR^5$ wherein R* is hydrogen or a straight or branched alkyl of from one to six carbon atoms, $R^5$ and $R^6$ are each independently hydrogen or alkyl of from one to about six carbon atoms and n is an integer from zero to six;

A is $—(CH_2)_nCO—$, $—SO_2—$, $—S(=O)—$, $—NHCO—$,

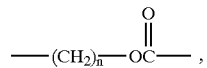

$—SCO—$, $—O—(CH_2)_nCO—$, $—HC=CHCO—$, or

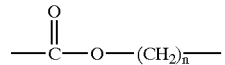

wherein n is an integer from zero to six;

$R^2$ is hydrogen, a straight or branched alkyl of from one to about six carbon atoms, $—HC=CH_2$, $—C≡CH$, $—CH_2—CH=CH_2$, $—CH_2C≡CH$, $—(CH_2)_nAr$, $—(CH_2)_nOR^*$, $—(CH_2)_nAr$, $—(CH_2)_nCO_2R^*$, or $—(CH_2)_nNR^5R^6$ wherein n, R*, $R^5$ and $R^6$ are as defined above and Ar is as defined below;

$R^3$, $R^4$ and $R^{14}$ are each independently selected from hydrogen, $R^2$ and $—(CH_2)_{n'}-B-D$ wherein:

n' is an integer of from zero to three;

B is a bond,
$—OCO(CH_2)_n—$,
$—O(CH_2)_n—$,
$—NHCO(CH_2)_n—$,
$—CONH(CH_2)_n—$,
$—NHCOCH=CH—$,
$—COO(CH_2)_n—$,
$—CO(CH_2)_n—$,
$—S(CH_2)_n—$,
$—SO(CH_2)_n—$,
$—SO_2(CH_2)_n—$,
$—NHSO_2(CH_2)_n—$,
$—SO_2NH(CH_2)_n—$,

wherein $R^7$ and $R^8$ are independently selected from hydrogen and $R^2$ or together form a ring $(CH_2)_m$ wherein m is an integer of from 1 to 5 and n is as defined above;

D is
$—COOR^*$,
$—CH_2OR^*$,
$—CHR^2OR^*$,
$—CH_2SR^*$,
$—CHR^2SR^*$,
$—CONR^5R^6$,
$—CN$,
$—NR^5R^6$
$—OH$,

—H, and acid replacements such as tetrazole,

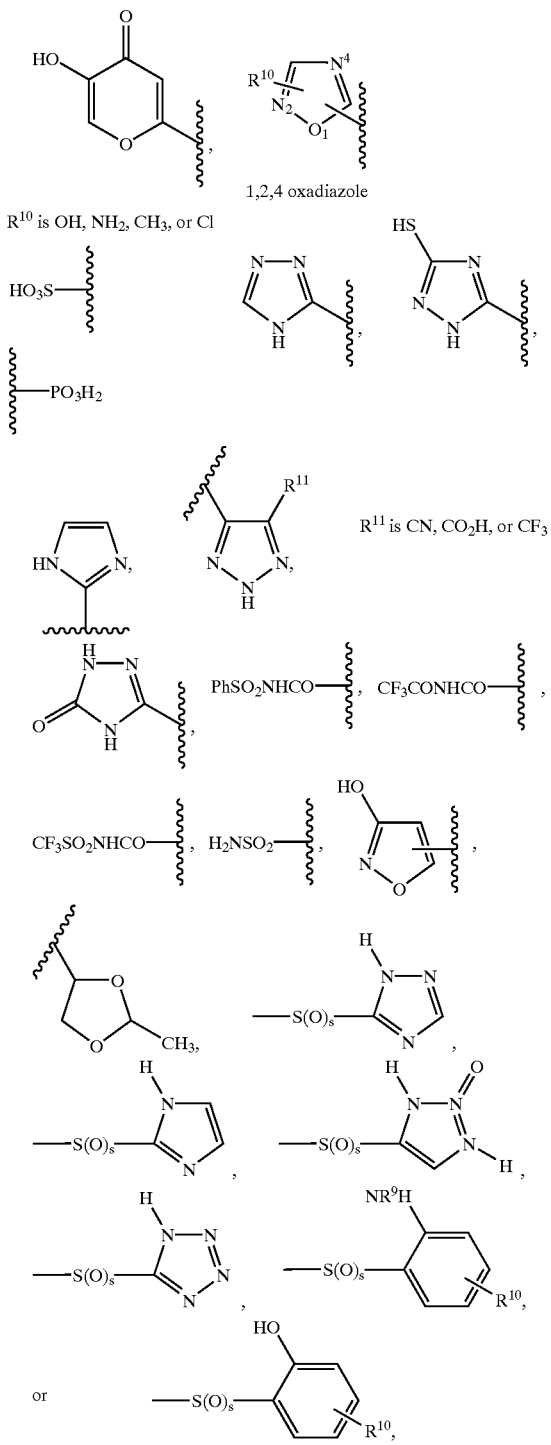

wherein R*, R², R⁵, and R⁶ are as defined above;
R⁹ is hydrogen or a straight or branched alkyl of from one to about six carbon atoms, —(CH₂)$_n$CO₂R*, —(CH₂)$_n$OAr', —(CH₂)$_n$Ar' or (CH₂)$_n$NR⁵R⁶, wherein n, R*, R⁵, and R⁶ are as defined above or taken from R³ and Ar' is taken from Ar as defined below;
R¹² and R¹³ are each independently hydrogen or are each independently taken with R³ and R⁴ respectively to form a moiety doubly bonded to the carbon atom; and Ar is a mono- or polycyclic unsubstituted or substituted carbo- or heterocyclic aromatic or hydroaromatic moiety.
Especially useful are compounds selected from:

(+/−)1,3,4,9-tetrahydro-3-methyl-3-[[2-phenylethyl)amino]carbonyl]-2H-pyrido[3,4-b]indole-2-carboxylic acid, tricyclo[3.3.1.1$^{3,7}$]dec-2-yl ester,
(R)-1,3,4,9-tetrahydro-3-methyl-3-[[2-phenylethyl)amino]carbonyl]-2H-pyrido[3,4-b]indole-2-carboxylic acid, tricyclo[3.3.1.1$^{3,7}$]dec-2-yl ester,
(S)-1,3,4,9-tetrahydro-3-methyl-3-[[2-phenylethyl)amino]carbonyl]-2H-pyrido[3,4-b]indole-2-carboxylic acid, tricyclo[3.3.1.1$^{3,7}$]dec-2-yl ester,
1,3,4,9-tetrahydro-3-[[[1-(hydroxymethyl)-2-phenylethyl]amino]carbonyl]-3-methyl-2H-pyrido[3,4-b]indole-2-carboxylic acid, tricyclo-[3.3.1.1$^{3,7}$]dec-2-yl ester (mixture of diastereomers),
(R)-1,3,4, 9-tetrahydro-3-[[[1-(hydroxymethyl)-2-phenylethyl]amino]carbonyl]-3-methyl-2H-pyrido[3,4-b]indole-2-carboxylic acid,tricyclo[3.3.1.1$^{3,7}$]dec-2-yl ester,
(S)-1,3,4,9-tetrahydro-3-[[[1-(hydroxymethyl)-2-phenylethyl]amino]carbonyl]-3-methyl-2H-pyrido[3,4-b]indole-2-carboxylic acid, tricyclo-[3.3.1.1$^{3,7}$]dec-2-yl ester,
1,3,4,9-tetrahydro-3-[[[1-(hydroxymethyl)-2-hydroxy-2-phenylethyl]amino]carbonyl]-3-methyl-2H-pyrido[3,4-b]indole-2-carboxylic acid, tricyclo-[3.3.1.1$^{3,7}$]dec-2-yl ester,
3-[[(2-amino-2-phenylethyl)amino]carbonyl]-1,3,4,9-tetrahydro-3-methyl]-2H-pyrido[3,4-b]indole-2-carboxylic acid, tricyclo[3.3.1.1$^{3,7}$)]dec-2-yl ester, (mixtures of diastereomers),
3-[[[2-(3-carboxy-1-oxopropyl)-amino]-2-phenylethyl]amino]carbonyl]-1,3,4,9-tetrahydro-3-methyl-2H-pyrido[3,4-b]indole-2-carboxylic acid, tricyclo[3.3.1.1$^{3,7}$)]dec-2-yl ester, [R-(R*,R*)] and [R-(R*,S*)]-,
3-[[[2-(R)-(3-carboxy-1-oxopropyl)amino]-2-phenylethyl]amino]carbonyl]-1,3,4,9-tetrahydro-3-(S)-methyl-2H-pyrido[3,4-b]indole-2-carboxylic acid, tricyclo[3.3.1.1$^{3,7}$]dec-2-yl ester,
3-[3-[3-[2-[2-[1,4-dioxo-4-(phenylmethoxy)butyl]amino]-2-phenylethyl]amino]carbonyl]-1,3,4,9-tetrahydro-3-methyl]-2H-pyrido[3,4-b]indole-2-carboxylic acid, tricyclo[3.3.1.1$^{3,7}$]dec-2-yl ester (mixture of diastereomers).
3-[[(2-hydroxy-2-phenylethyl)amino]carbonyl]-1,3,4,9-tetrahydro-3-methyl]-2H-pyrido[3,4-b]indole-2-carboxylic acid, tricyclo[3.3.1.1$^{3,7}$]dec-2-yl ester,
butanedioic acid, mono[2-[[[2,3,4,9-tetrahydro-3-methyl-2-[(tricyclo[3.3.1.1$^{3,7}$]dec-2-ylox)carbonyl]-1H-pyrido[3,4-b]indole-3-yl]carbonyl]amino]-1-phenethyl] ester.
3-[[[2-[(3-carboxyacetyl)amino]-2-phenethyl]amino]carbonyl]-1,3,4,9-tetrahydro-3-methyl-2H-pyrido[3,4-b]indole-2-carboxylic acid, [tricyclo[3.3.1.1$^{3,7}$]dec-2-yl ester (mixture of diastereomers),
3-[[[2-[(3-carboxy-1-oxo-2-propenyl)amino]-2-phenylethyl]amino]carbonyl]1,3,4,9-tetrahydro-3-methyl-2H-pyrido[3,4-b]indole-2-carboxylic acid, [tricyclo[3.3.1.1$^{3,7}$]dec-2-yl ester (mixture of diastereomers),
3-[[[1-[[(3-carboxy-1-oxopropyl)amino]methyl]-1-phenethyl]amino]carbonyl]-1,3,4,9-tetrahydro-3-methyl-2H-pyrido[3,4-b]indole-2-carboxylic acid, [tricyclo-[3.3.1.1$^{3,7}$]dec-2-yl ester (mixture of diastereomers),
(+/−)-1,3,4,9-tetrahydro-3-[[(2-phenethyl)amino]carbonyl]-2H-pyrido[3,4-b]indole-2-carboxylic acid, [tricyclo[3.3.1.1$^{3,7}$]]dec-2-yl ester, 3-[[(1-carboxy-2-phenethyl)amino]carbonyl]-1,3,4,9-tetrahydro-2H-pyrido[3,4-b]indole-2-carboxylic acid, 1,1-dimethylethyl ester, (+/−)-1,3,4,9-tetrahydro-3-methyl-N-(2-phenylethyl)-2-[(tricyclo[3.3.1.1$^{3,7}$])dec-2-ylamino)sulfonyl]1H-pyrido[3,4-b]indole-3-carboxamide, 3-[[[3-carboxy-1-(phenylmethyl)propyl]amino]carbonyl)-1,3,4,9-tetrahydro-3-methyl-2H-pyrido[[3,4-b]indole-2-carboxylic acid, tricyclo-[[3.3.1.1$^{3,7}$]dec-2-yl ester, 1,3,4,9-tetrahydro-3-methyl-3-[[[2-[[1-oxo-3-(1H-tetrazol-5-yl)propyl]amino]-2-phenethyl]amino]carbonyl]-2H-pyrido[3,4-b]indole-2-carboxylic acid, tricyclo[3.3.1.1$^{3,7}$]dec-2-yl ester, and 3-[[[2-[[(2-carboxy-1-cyclopropyl)carbonyl]amino]-2-phenethyl]amino]carbonyl)-1,3,4,9-tetrahydro-3-methyl-2H-pyrido[3,4-b]indole-2-carboxylic acid ethyl ester, tricyclo[3.3.1.1$^{3,7}$]dec-2-yl ester.

Other CCD$_B$ antagonists (gastrin antagonists) include but are not limited to:

L-365-091 which is 1-((3-((((4-chlorophenyl)amino)carbonyl)amino)-2,3-dihydro-2-oxo-5-phenyl-1H-1,4-benzodiazepin-1-yl)acetyl)-pyrrolidine; and (S)-5-[(10,11-dihydrodibenzo[a,d]cyclohepten-5-yl)amino]4-[(1H-indol-2yl)carbonyl]amino]-5-oxo-pentanoic acid.

L-365,260 which is (R)-N-(2,3-dihydro-1-methyl-2-oxo-5-phenyl-1H-1,4-benzodiazepine-3-yl)-N'-(3-methylphenyl)urea, LY-262,690 which is trans-1-Pyrazolidinecarboxamide, 5-(2-chlorophenyl)-3-oxo-4-phenyl-N-[4-(trifluoromethyl)phenyl]-, LY-262,691 which is trans-5-(3-chlorophenyl)-3-oxo-4-phenyl-N-[4-(bromo)phenyl]-1-pyrazolidinecarboxamide, and trans-1-pyrazolidinecarboxamide-N-(4-bromophenyl)-5-(2-chlorophenyl)-3-oxo-phenyl-.

Other compounds useful in the instant invention are pyrazolidinones of formula

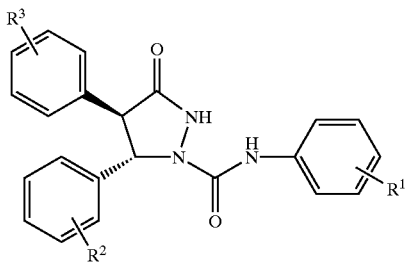

or a pharmaceutically acceptable salt thereof wherein
R$^1$ is 2,3-dichloro,
3,4—(CH$_2$)$_4$,
4,CF$_3$, or
4-Br;
R$^2$ is hydrogen,
2-chloro,
2,3-dichloro, or
CN; and
R$^3$ is hydrogen -trans or -cis.

These are disclosed in *Drugs of the Future* 16(7):631–740 (1991). The compounds are made as described in Synthetic Examples 1–3 below.

Other compounds useful in the methods of treatment of the instant invention are quinazolinones disclosed in U.S. Pat. No. 5,075,313 of formula

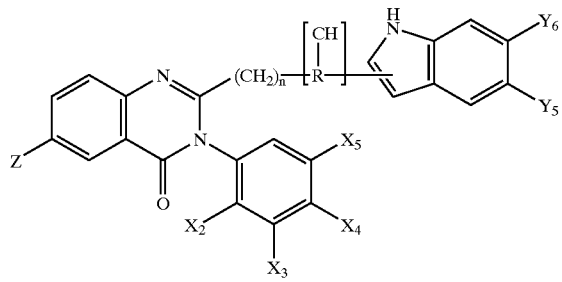

in which
n is 1 or 2 and m is 0 or 1;
R is hydrogen, C$_1$–C$_4$ alkyl, benzyl, or phenyl;
Z is hydrogen or halo;
X$_2$, X$_3$, X$_4$, and X$_5$ are independently selected from the group consisting of hydrogen, halo, trifluoromethyl, C$_1$–C$_6$ alkoxy, C$_1$–C$_6$ alkyl, C$_1$–C$_6$ alkylthio, and —NR$_2$R$_3$, in which R$_2$ and R$_3$ are independently hydrogen, C$_1$–C$_4$ alkyl, benzyl, or phenyl, or R$_2$ and R$_3$ taken together with the nitrogen atom to which they are bonded from a 5- or 6-membered ring; or X$_r$ and X$_{r+1}$, in which r is 2, 3, or 4,taken together from a divalent C$_3$–C$_5$ alkylene group or methylenedioxy; and Y$_5$ and Y$_6$ are independently selected from the group consisting of hydrogen, C$_1$–C$_6$ alkyl, C$_1$–C$_6$ alkoxy, halo, and trifluoromethyl; and pharmaceutically acceptable salts thereof.

Methodology

A test carried out using the mouse light/dark box and the rat T-maze reinforced alternation task. The results indicate that Compound 1 CI-988 improves basal cognition and inhibits the impairments in performance caused by cholinergic deficits.

On repeated exposure to the light/dark box mice habituate by moving more rapidly from the light to the dark side. The habituation occurs over a 4 to 6 day period, with a reduction in latency of movement from about 14 sec to 2 to 4 sec by the 4th day of the test. The daily administration of Compound 1 (0.01 µg/kg, SC) significantly improved performance. At this dose Compound 1 showed no anxiolytic activity. The scopolamine (0.25 mg/kg) induced impairment of performance was almost completely antagonized by Compound 1 (0.01 µg/kg).

In the twice daily administration of Compound 1 (0.1 mg/kg, IP) had no effect on the learning of this task. However, the deficit induced by twice daily administration of scopolamine (0.25 mg/kg) was antagonized by coadministration of Compound 1 (0.1 mg/kg, IP).

See FIGS. 1 to 5 below.

The days (1–6) are along the X axis and the time in seconds is along the Y axis (latency white to black) and Day 6 scopolamine was 0.25.

Five mice were tested o p <0.001 indicates improved habituation, comparison is with 1 day.

* p <0.05 to p <0.001 is improved performance, compared to control.

+ p <0.001 is scopolamine impairment.

Δ p <0.001 is inhibition of scopolamine impairment.

Figure 1:
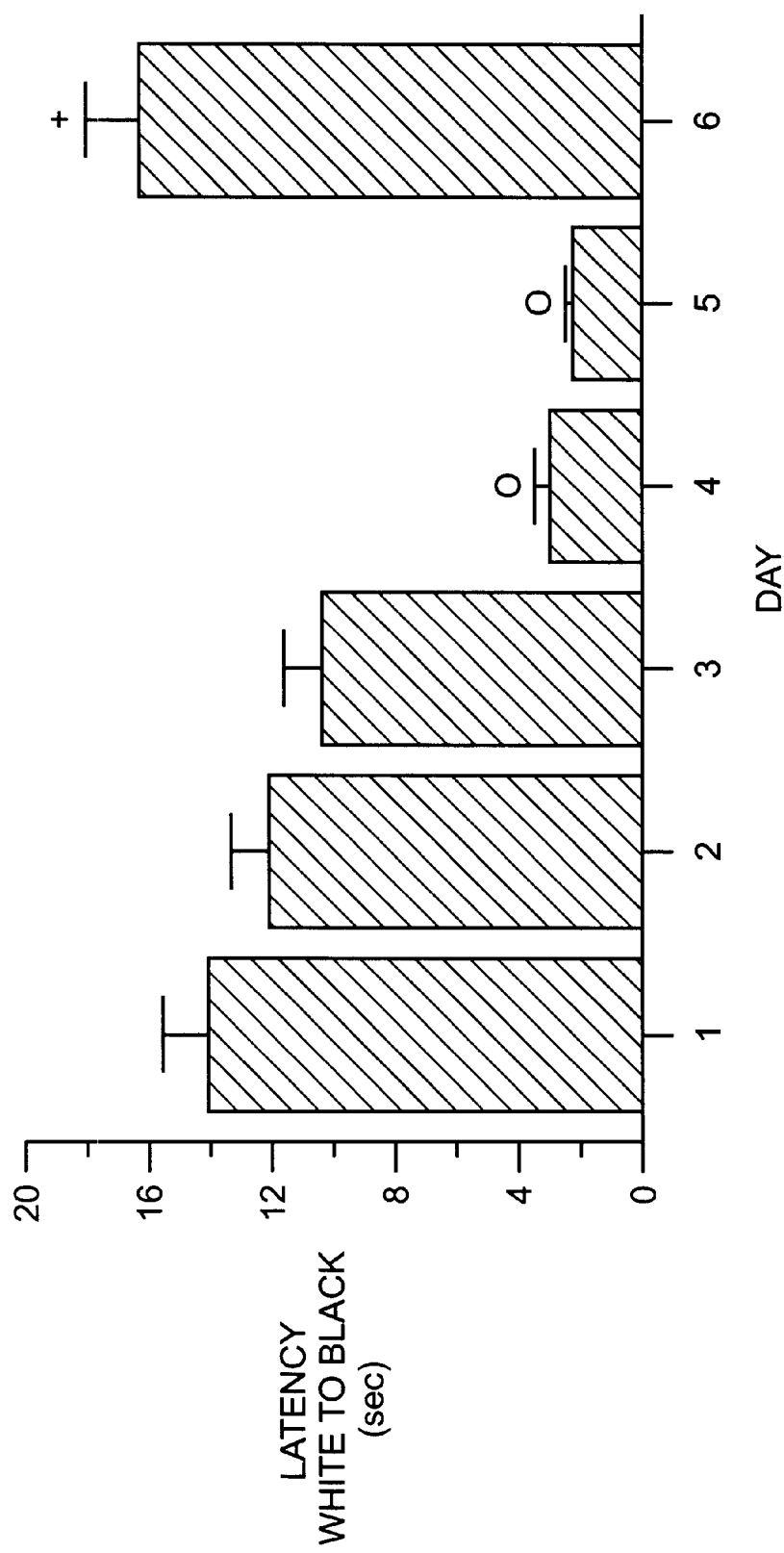
FIGS. 1 and 2 show the influence of Compound 1 on mouse habituation patterns and on acute scopolamine impairment. The compounds was administered at a dose of 0.00001 mg/kg SC once daily.

FIG. 1 is the control.

Figure 2:
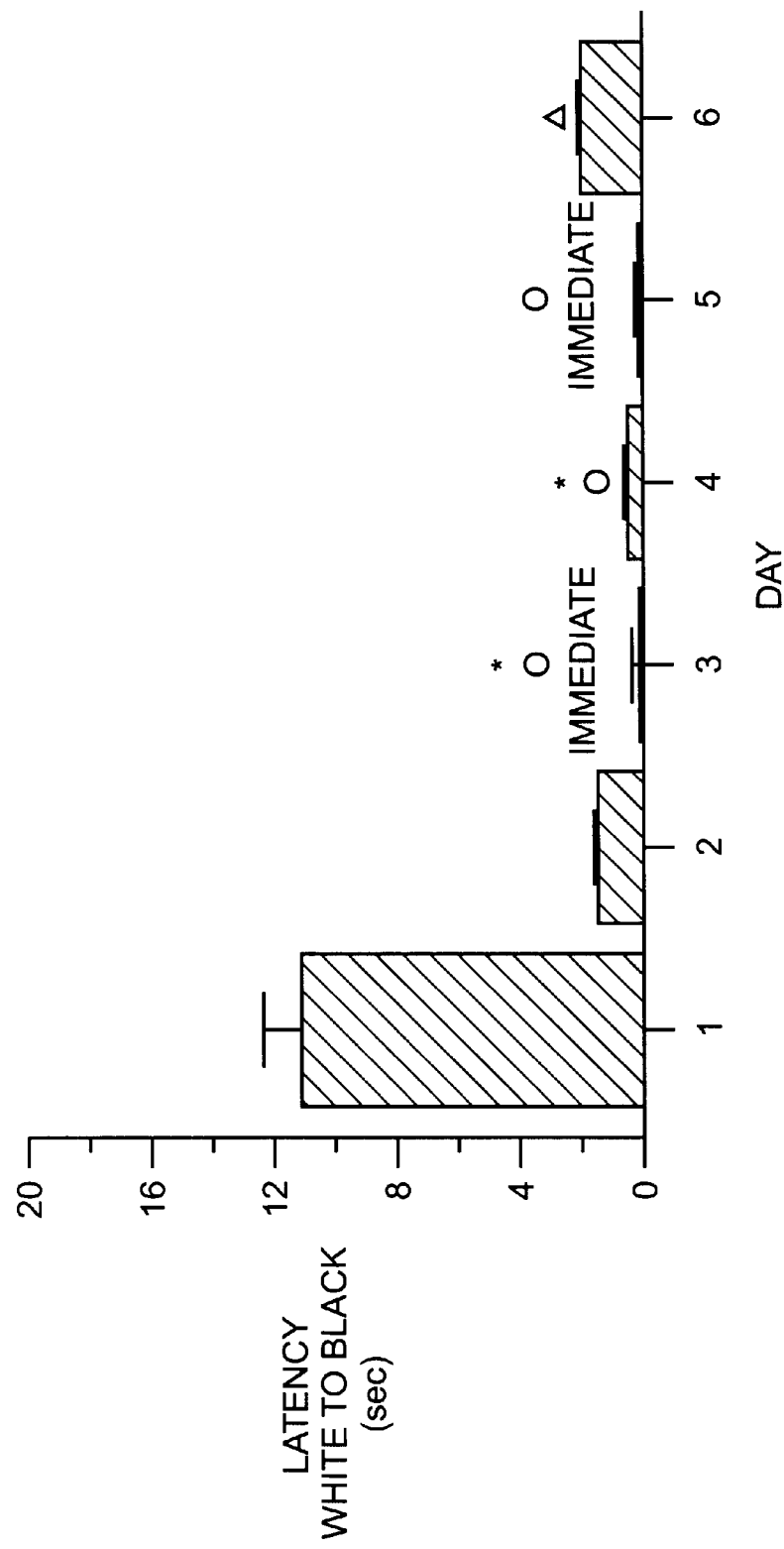

FIG. 2 is Compound 1.

Figure 3:
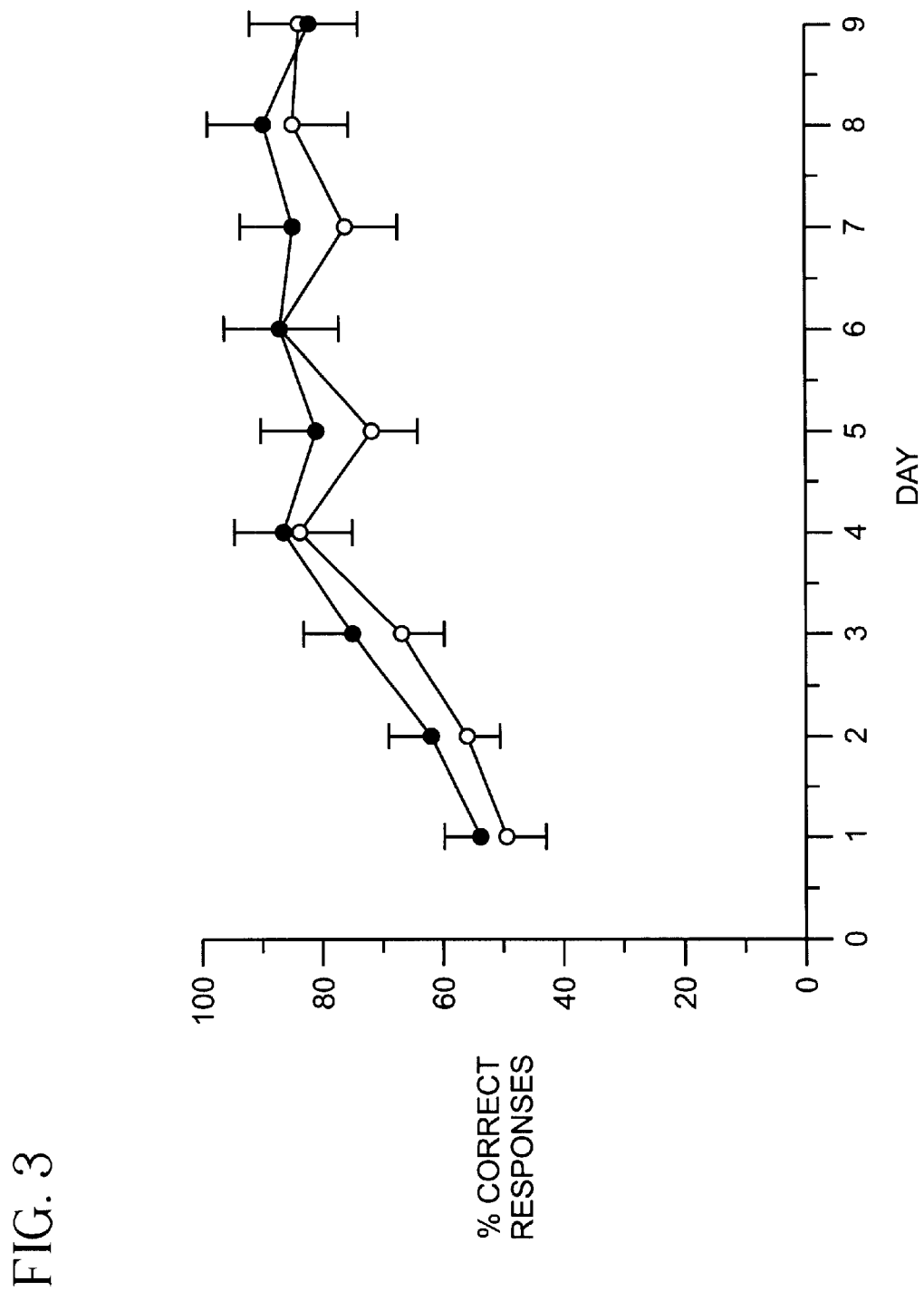
Figure 4:
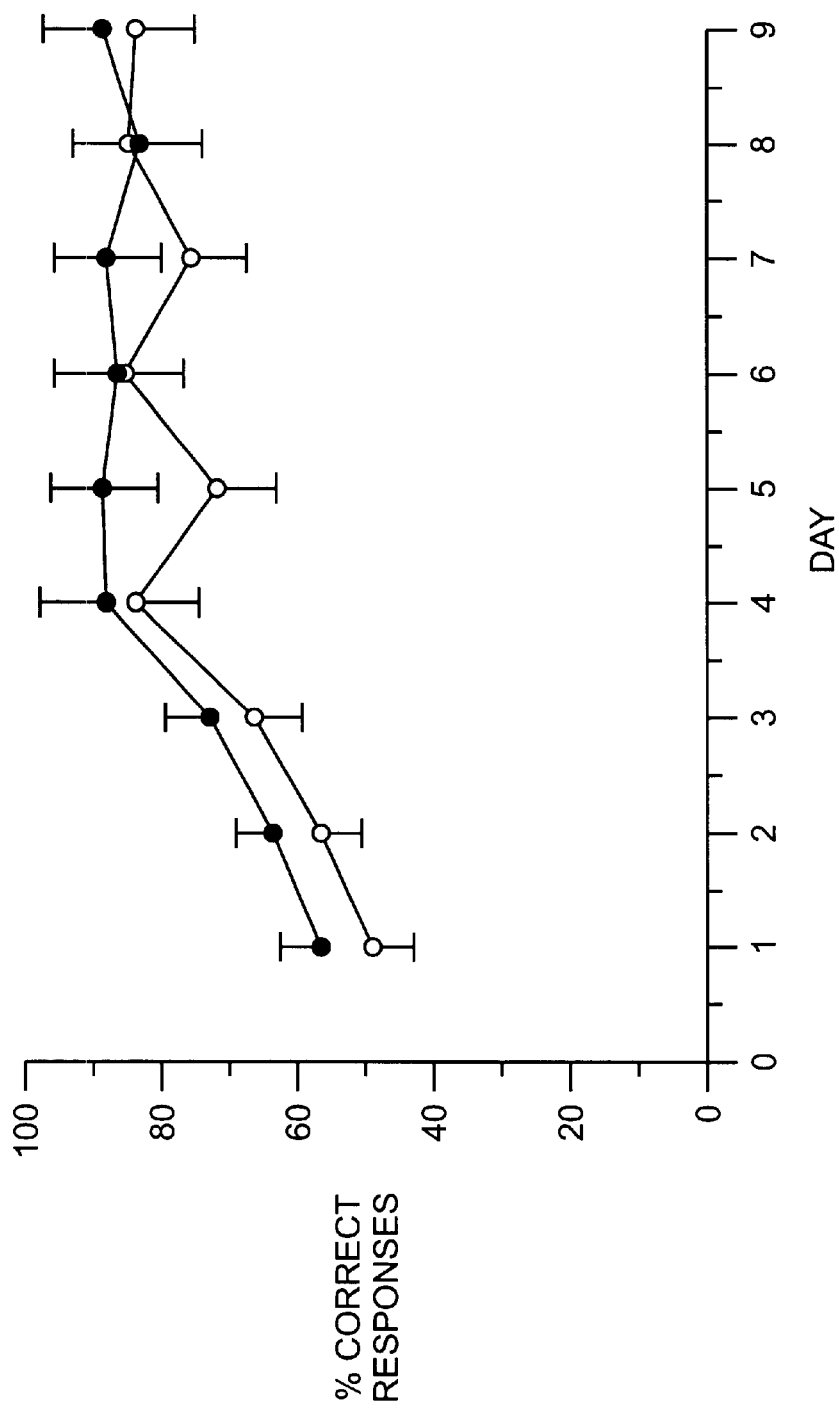

FIGS. 3 and 4 show the effect of Compound 1 on the performance of a reinforced alternation task.

The X axis is the day and the Y axis is the percent correct responses.

The number of mice tested was six.

0 - - - 0 is the control.

●- - -● is Compound 1.

In FIG. 3 Compound 1 was given at 0.01 mg/kg IP BID.

In FIG. 4 Compound 1 was given at 1.0 mg/kg IP BID.

Figure 5:
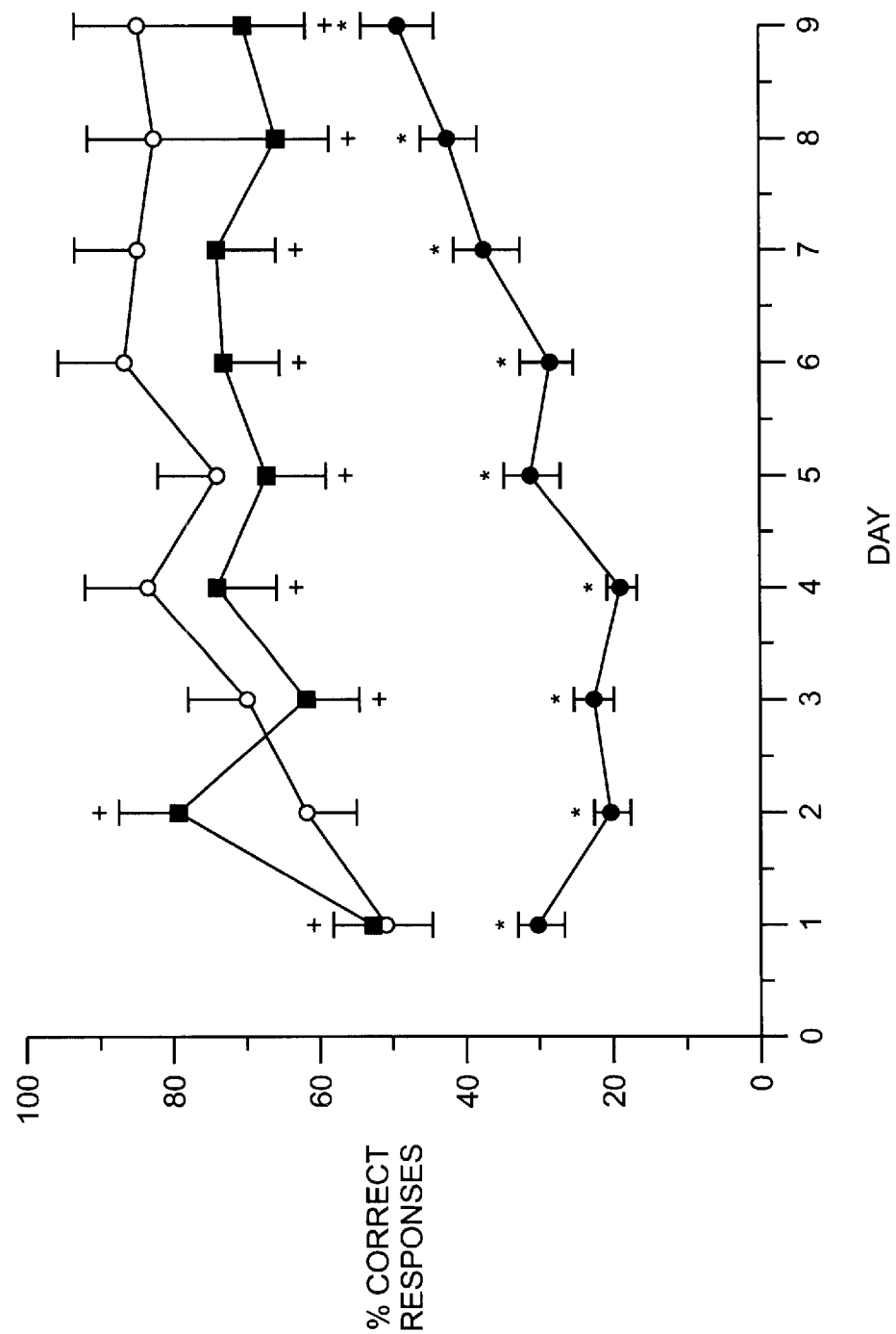

FIG. 5 shows the effect of Compound 1 on scopolamine— the induced deficits in performance on a T-maze reinforced alternation task. The X axis is the day and the Y axis is the percent correct responses.

The number of mice tested was six.

0 - - - 0 is the control vehicle.

●- - -● scopolamine at 0.25 mg/kg IP BID.

■- - -■ is scopolamine and Compound 1 at 0.1 mg/kg IP BID.

* p <0.05 to p <0.001 is scopolamine impairment.

+ p <0.05 to p <0.001 is inhibition of scopolamine impairment.

Since the $CCK_B$ antagonist CI-988 exhibited activity in an art recognize models of $CCD_B$ receptor antagonists will be effective in the treatment of cognitive disorders in man.

Certain $CCK_B$ antagonists were tested in the antagonists will be effective in the treatment of cognitive disorders in man.

Examples of formulations of the subject compounds and of salts thereof are illustrated by the following examples.

EXAMPLE 1

Injectables 1 mg to 100 mg/mL

CI-988

Water for Injection USP q.s.

The compound or a suitable salt thereof is dissolved in water and passed through a 0.2-micron filter. Aliquots of the filtered solution are added to ampoules or vials, sealed and sterilized.

EXAMPLE 2

Capsules 5 mg, 100 mg, 200 mg, 300 mg or 400 mg

CI-988, 250 g

Lactose USP, Anhydrous q.s. or 250 g

Sterotex Powder HM, 5 g

Combine the compound and the lactose in a tumble blend for 2 minutes, blend for 1 minute with the intensifier bar, and then tumble blend again for 1 minute. A portion of the blend is then mixed with the Sterotex Powder, passed through a #30 screen, and added back to the remainder of the blend. The mixed ingredients are then blended for 1 minute, blended with the intensifier bar for 30 seconds, and tumble blended for an additional minute. The appropriately sized capsules are filled with 141 mg, 352.5 mg, or 705 mg of the blend, respectively, for the 50 mg, 125 mg, and 250 mg containing capsules.

EXAMPLE 3

Tablets 50 mg, 100 mg, 200 mg, 300 mg, 400 mg, 500 mg or 600 mg

CI-988

Corn Starch NF, 200 g

Cellulose, Microcrystalline, 46 g

Sterotex Powder HM, 4 g

Purified Water q.s. or 300 mL

Combine the corn starch, the cellulose, and the compound together in a planetary mixer and mix for 2 minutes. Add the water to this combination and mix for 1 minute. The resulting mix is spread on trays and dried in a hot air oven at 50° C. until a moisture level of 1 to 2 percent is obtained. The dried mix is then milled with a Fitzmill through a #RH2B screen, and added back to the milling mixture and the total blended for 5 minutes by drum rolling. Compressed tablets of 150 mg, 375 mg, and 750 mg, respectively, of the total mix are formed with appropriate sized punches the 50 mg, 125 mg, or 500 mg containing tablets.

Synthetic Example 1

Trans-5-(2-chlorophenyl)-3-oxo-4-phenyl-N-[4-(bromophenyl]-1-pyrazolidinecarboxamide Step 1. Preparation of αphenyl-2-chlorocinnamic acid Method used: Org. Syn. Coll. IV:777 (1963)

Phenylacetic acid (54.46 g, 0.4 M) was dissolved in acetic anhydride (80 mL). O-chlorobenzaldehyde (56.23 g, 0.4 M) was added slowly, with stirring. This was followed by the slow addition of triethylamine (40 mL). The reaction mixture was stirred at reflux for 5 hours. The reaction mixture was steam distilled until the distillate was no longer cloudy. The distillate was discarded. The aqueous residue was cooled. The solution was decanted from the gummy solid. This solid was dissolved in a 10% $K_2CO_3$ solution. The basic solution was charcoaled then filtered through a pooled Super cell. The filtrate was made acidic (pH 1) with 10% HCl, cooled, and the solid filtered. The product was recrystallized from 50% ethanol/$H_2O$ to yield 52.14 g of white solid, mp 158–161° C.

Step 2. Preparation of αphenyl-2-chlorocinnamic acid methyl ester

αPhenyl-2-chlorocinnamic acid (26.29 g (0.102 M) was dissolved in methanol (300 cc). Anhydrous HCl was bubbled through the reaction mixture with stirring for 15 minutes. The reaction mixture was refluxed for 2 hours, then HCl was bubbled through the reaction mixture for another 15 minutes. The reaction was stirred at reflux overnight. The methanol was removed in vacuo and the residue taken up in ether. The ether solution was washed with $H_2O$, saturated $NaHCO_3$ solution, and brine. It was then dried over $MgSO_4$. The ether solution was concentrated in vacuo to yield an oil that quickly solidified to yield 27.13 g of product, mp 67–69° C.

Step 3. Preparation of 4-(O'-chlorophenyl)-5-phenyl-3-pyrazolidine

The ester from Step 2 (27.05 g, 0.0993 M) was dissolved in ethanol (75 cc). Eighty-five percent hydrazine hydrate (5.76 g, 0.0993 M) was added. The reaction mixture was stirred at reflux for 24 hours, then cooled. H₂O was added slowly with stirring. The product oiled out. The ethanol water was decanted from the oil. The oil was taken up in ether. The ether solution was washed with cold water, then dried over MgSO₄. The ether solution was concentrated in vacuo. A small amount of ether was added to the residue. The white solid was filtered and dried in vacuo to yield 9.56 g of product, mp 123–124° C.

Step 4. Preparation of trans-5-(2-chlorophenyl)-3-oxo-4-phenyl-N-[4-(bromophenyl]-1-pyrazolidinecarboxamide The pyrazolidone obtained in Step 3 (2.73 g, 0.01 M) was dissolved in THF (100 mL). p-Bromophenyl isocyanate (1.98 g, 0.01 M) was added. The reaction mixture was stirred overnight at room temperature. The clear solution was concentrated in vacuo to yield 4.73 g of a white solid. The sol id was boiled in isopropyl ether. The insoluble solid was filtered from the warm ether and dried to yield 3.71 g of the product, mp 189–190° C.

Analysis for $C_{22}H_{17}BrClN_3O_2$ (MW 470.762):

Calcd.: C, 56.13; H, 3.64; N, 8.91.

Found: C, 56.43; H, 3.87; N, 8.71.

IR NMR and MS consistent for the desired product.

Synthetic Example 2

Trans-5-(2-chlorophenyl)-3-oxo-4-phenyl-N-[4-(trifluoromethyl)phenyl]-1-pyrazolidinecarboxamide Substituting ααα trifluoro-p-tolyl isocyanate (1.87 g, 0.01 M) for p-bromophenyl isocyanate in Step 4, one obtains 3.6 g of the product, mp 193–194° C.

Analysis for $C_{23}H_{17}ClF_3N_3O_2$ (MW 459.859):

Calcd.: C, 60.07; H, 3.73; N, 9.14.

Found: C, 60.16; H, 3.81; N, 9.09.

IR, NMR and MS consistent for the desired product.

Synthetic Example 3

3-nitrophenol (50.0 g, 360 mmol), isopropyl iodide (76.19 g, 450 mmol), and K₂CO₃ (60 g) were combined and heated at reflux under N₂ overnight in acetone (400 mL). After solvent removal in vacuo, the residue was partitioned between EtOAc and H₂O. The separated organic layer was washed with 1 N NaOH, brine, dried over Na₂SO₄, and concentrated in vacuo to provide 56 g (86%) of 3-isopropoxynitrobenzene as a clear yellow oil.

A mixture of the above product (8.5 g, 50 mmol), PtO₂ (0.3 g), and EtOH (200 mL) was hydrogenated (40 psi H₂) at room temperature for 1.5 hours in a Paar shaker. The mixture was filtered through Celite and concentrated in vacuo to furnish 7.08 g of the desired aniline. This material was combined with isatoic anhydride (7.35 g, 45 mmol) and heated at 90° C. for 2 hours. Upon cooling and addition of hexanes, the product crystallized to give 10.19 g (83%) of 2-amino-N-(3-isopropoxyphenyl)benzamide as a white solid. An analytical sample was obtained by recrystallization from 20% EtOAc/hexanes, mp 79–86° C.; ¹H NMR (CDCl₃) δ1.36 (6H, d, J=6.1 Hz), 4.59 (1H, h, J=6.1 Hz), 5.2 (2H, bs), 6.6–6.8 (3H, m), 7.0–7.1 (1H, m), 7.2–7.4 (3H, m), 7.47 (1H, d, J=7.7 Hz), 7.80 (1H, bs); IR (CHCl₃) 1664, 1611, 1524, 1490 cm⁻¹; MS (FD) 270 (M⁺). Anal. ($C_{16}H_{18}N_2O_2$) C, H, N.

A solution of 3-[(2,2-dimethyl-4,6-dioxo-1,3-dioxan-5-yl)methyl]-5-bromoindole (4.12 g, 12 mmol) prepared according to the method of Farlow, et al (Farlow, D. S.; Flaugh, M. E.; Horvath, S. D.; Lavignino, E. R.; Pranc, P. Two Efficient Syntheses of Indole-3-Propionic Esters and Acids. Further Applications of Meldrum's Acid. *Org. Prep. Proced. Int.* 13:39–48 (1981), the above benzamide (3.48 g, 13 mmol) and pyridinium p-toluenesulfonate (1.64 g, 6.5 mmol) in 50 mL of pyridine was heated at reflux for 3.5 days. The reaction mixture was concentrated in vacuo, chromatographed (SiO₂, 30% EtOAc/hexanes), and crystallized to give 2.13 g (36%) of compound 22, mp 179–181° C.; ¹H NMR (CDCl₃) δ1.31 (3H, d, J=6.0 Hz), 1.34 (3H, d, J=6.1 Hz), 2.8 (2H, m), 3.2 (2H, m), 4.53 (1H, h, J=6.0 Hz), 6.7–7.6 (9H, m), 7.8 (2H, m), 8.2–8.4 (2H, m); IR (KBr) 1671 cm⁻¹; MS (FAB) 502, 504 (M⁺+H). Anal. ($C_{27}H_{24}N_3O_2Br$) C, H, N.

What is claimed is:

1. A method of treating the symptoms of cognitive decline which comprises administering to a mammal in need of such treatment a therapeutically effective amount of a compound in unit dosage form of formula

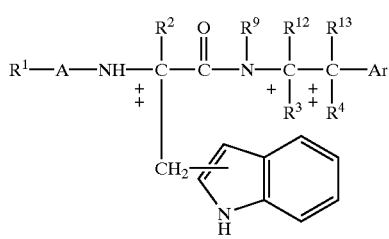

I or a pharmaceutically acceptable salt thereof wherein:

R¹ is a cycloalkyl or polycycloalkyl hydrocarbon of from three to twelve carbon atoms with from zero to four substituents each independently selected from the group consisting of a straight or branched alkyl of from one to about six carbon atoms, halogen, CN, OR*, SR*, CO₂R*, CF₃, NR⁵R⁶, and —(CH₂)ₙOR⁵ wherein R* is hydrogen or a straight or branched alkyl of from one to six carbon atoms, R⁵ and R⁶ are each independently hydrogen or alkyl of from one to about six carbon atoms and n is an integer from zero to six;

A is —(CH₂)ₙCO—, —SO₂—, —S(=O)—, —NHCO—,

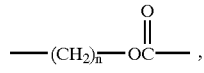

—SCO—, —O—(CH₂)ₙCO— or —HC=CHCO— wherein n is an integer from zero to six;

R² is a straight or branched alkyl of from one to about six carbon atoms, —HC=CH₂, —C≡CH, —CH₂—CH=CH₂, —CH₂C≡CH, —(CH₂)ₙAr, —(CH₂)ₙOR*, —(CH₂)ₙOAr, —(CH₂)ₙCO₂R*, or —(CH₂)ₙNR⁵R⁶ wherein n, R*, R⁵ and R⁶ are as defined above and Ar is as defined below;

R³ and R⁴ are each independently selected from hydrogen, R² and —(CH₂)ₙ'B'D wherein:

n' is an integer from zero to three;

B is a bond,
—OCO(CH₂)ₙ—,
—O(CH₂)ₙ—,
—SO₂NH(CH₂)ₙ—,
—NHSO₂ (CH₂)ₙ—,
—NHCO(CH₂)ₙ—,
—CONH(CH₂)ₙ—, —NHCOCH=CH—,
—COO(CH$_2$)$_n$—,
—CO(CH$_2$)$_n$—,
—S—(CH$_2$)$_n$—,
—S(=O)—(CH$_2$)$_n$—,
—SO$_2$—(CH$_2$)$_n$—,
—CONH—C=C—,

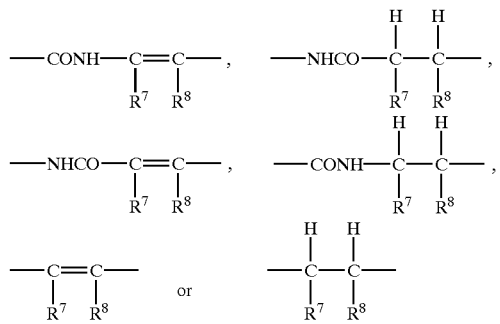

wherein R$^7$ and R$^8$ are independently selected from hydrogen and R$^2$ or together form a ring (CH$_2$)$_m$ wherein m is an integer of from 1 to 5 and n is as defined above;

D is —COOR*,
—CH$_2$OR*,
—CHR$^2$OR*,
—CH$_2$SR*,
—CHR$^2$SR*,
—CONR$^5$R$^6$,
—CN,
—NR$^5$R$^6$,
—OH,
—H and acid replacements tetrazole, and

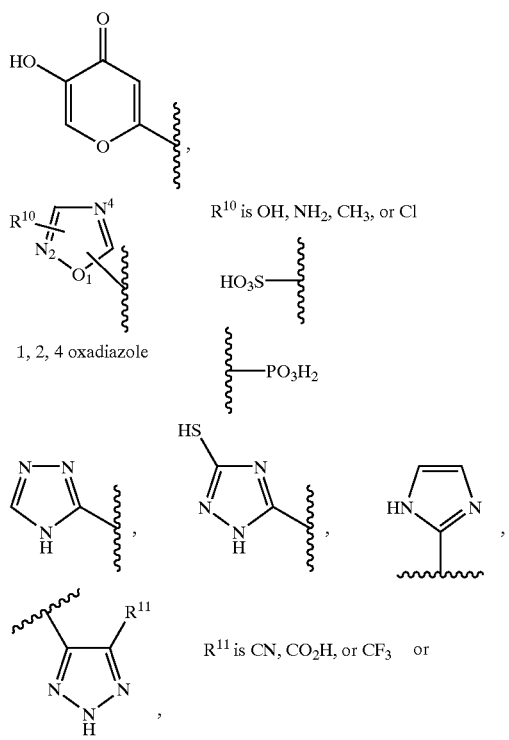

1, 2, 4 oxadiazole

R$^{10}$ is OH, NH$_2$, CH$_3$, or Cl

R$^{11}$ is CN, CO$_2$H, or CF$_3$ or

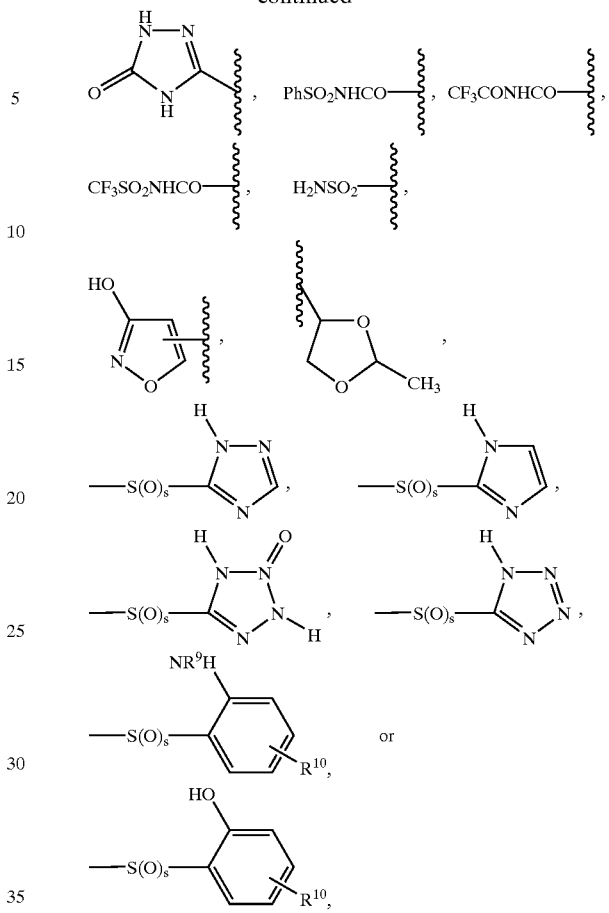

wherein R*, R$^2$, R$^5$, and R$^6$ are as defined above;
R$^9$ is hydrogen or a straight or branched alkyl of from one to about six carbon atoms, —(CH$_2$)$_n$CO$_2$R*, —(CH$_2$)$_n$OAr', —(CH$_2$)$_n$Ar' or (CH$_2$)$_n$NR$^5$R$^6$, wherein n, R*, R$^5$, and R$^6$ are as defined above or taken from R$^3$ and Ar' is taken from Ar as defined below;
R$^{12}$ and R$^{13}$ are each independently hydrogen or are each independently taken with R$^3$ and R$^4$ respectively to form a moiety doubly bonded to the carbon atom; and
Ar is a mono- or polycyclic unsubstituted or substituted carbo- or heterocyclic aromatic or hydroaromatic moiety.

2. A method according to claim 1 which comprises administering to a mammal in need of such treatment a therapeutically effective amount of a compound in unit dosage form selected from:

1. [1S-[1α,2β[S*[S*(E)]],4α]]-4-[[2-[[3-(1H-indol-3-yl)-2-methyl-1-oxo-2-[[[(1,7,7-trimethylbicyclo[2.2.1]hept-2-yl)oxy]carbonyl]amino]propyl]amino]-1-phenylethyl]amino]-4-oxo-2-butenoic acid,

2. [1S-[1α,2β[S*(S*)],4α]]-4-[[2-[[3-(1H-indol-3-yl)-2-methyl-1-oxo-2-[[[(1,7,7-trimethylbicyclo[2.2.1]hept-2-yl)oxy]carbonyl]amino]propyl]methylamino]-1-phenylethyl]amino]-4-oxobutanoic acid,

3. [1S-[1α,2β[S*(S*)],4α]]-4-[[2-[[3-(1H-indol-3-yl-2-methyl-1-oxo-2-[[[(1,7,7-trimethylbicyclo[2.2.1]hept-2-yl)amino]carbonyl]amino]propyl]amino]-1-phenylethyl]amino]-4-oxobutanoic acid,

4. [R-(R*,R*)]-4-[[2-[[3-(1H-indol-3-yl)-2-methyl-1-oxo-2-[(tricyclo[3.3.1.1$^{3,7}$]dec-2-ylsulfonyl)amino]propyl]amino]-1-phenylethyl]amino]-4-oxobutanoic acid,

5. [R-(R*,S*)]-4-[[2-[[3-(1H-indol-3-yl)-2-methyl-1-oxo-2-[(tricyclo[3.3.1.1³,⁷]dec-2-ylsulfonyl)amino]propyl]amino]-3-phenylpropyl]amino]-4-oxobutanoic acid,

6. [1R-[1α[R*(S*)],2β]] and [1S-[1α[S*(R*)],2β]]-4-[[2-[[2-[[[(2-fluorocyclohexyl)oxy]carbonyl]amino]-3-(1H-indol-3-yl)-2-methyl-1-oxopropyl]amino]-3-phenylpropyl]amino]-4-oxobutanoic acid,

7. [1R-[1α[R*(S*)],2β]] and [1S-[1α[S*(R*)],2β]]-4-[[2-[[2-[[[(2-fluorocyclohexyl)oxy]carbonyl]amino]-3-(1H-indol-3-yl)-2-methyl-1-oxopropyl]methylamino]-3-phenylpropyl]amino]-4-oxobutanoic acid,

8. [1R-[1α[R*(S*)],2β]] and [1S-[1α[S*(R*)],2β]]-4-[[2-[[3-(1H-indol-3-yl)-2-methyl-1-oxo-2-[[[[2-(trifluoromethyl)-cyclohexyl]oxy]carbonyl]amino]propyl]amino]-3-phenylpropyl]amino]-4-oxobutanoic acid,

9. [1R-[1α[R*(S*)],2β]] and [1S-[1α[S*(R*)],2β]]-4-[[2-[[3-(1H-indol-3-yl)-2-methyl-1-oxo-2-[[[[2-(trifluoromethyl)cyclohexyl]oxy]carbonyl]amino]propyl]methylamino]-3-phenylpropyl]amino]-4-oxobutanoic acid,

10. [R-(R*,S*)]-4-[[2-[[3-(1H-indol-3-yl)-2-methyl-1-oxo-2-[[(tricyclo[3.3.1.1³,⁷]dec-2-yloxy)carbonyl]amino]propyl]methylamino]-3-phenylpropyl]amino]-4-oxobutanoic acid,

11. [1S-[1α,2β[S*(R*)],4α]]-[1-(1H-indol-3-ylmethyl)-1-methyl-2-oxo-2-[[2-[[1-oxo-3-(1H-tetrazol-5-yl)propyl]amino]-1-(phenylmethyl)ethyl]amino]ethyl]carbamic acid, 1,7,7-trimethylbicyclo[2.2.1]hept-2-yl ester,

12. [1S-[1α,2β[S*,R*)]-[1-(1H-indol-3-ylmethyl)-1-methyl-2-oxo-2-[[2-[[1-oxo-3-(1H-tetrazol-5-yl)propyl]amino]-2-phenylethyl]amino]ethyl]carbamic acid, 1,7,7-trimethylbicyclo[2.2.1]hept-2-yl ester,

13. N-[2-methyl-N-[(tricyclo[3.3.1.1³,⁷]dec-2-yloxy)carbonyl]-D-tryptophyl]-L-phenylalanyl-glycine,

14. N-[2-methyl-N-[(tricyclo[3.3.1.1³,⁷]dec-2-yloxy)carbonyl]-D-tryptophyl]-L-phenylalanyl-β-alanine,

15. (R)-tricyclo[3.3.1.1³,⁷]dec-2-yl [1-(1H-indol-3-ylmethyl)-1-methyl-2-[methyl(2-phenylethyl)amino]-2-oxo-ethylcarbamate,

16. (±)-trans-2-chlorocyclohexyl [1-(1H-indol-3-ylmethyl)-1-methyl-2-oxo-2-[(2-phenylethyl)amino]ethyl]carbamate,

17. 2-chorocyclohexyl [2-[[1-(hydroxymethyl)-2-phenylethyl]amino]-1-(1H-indol-3-ylmethyl)-1-methyl-2-oxoethyl]carbamate,

18. 2-[[2-[[[(2-chlorocyclohexyl)oxy]carbonyl]amino]-3-(1H-indol-3-yl)-2-methyl-1-oxopropyl]amino]-3-phenylpropyl butanedioate,

19. 2-[[2-[[[(2-methylcyclohexyl)oxy]carbonyl]amino]-3-(1H-indol-3-yl)-2-methyl-1-oxopropyl]amino]-3-phenylpropyl butanedioate,

20. (±)-tricyclo[3.3.1.1³,⁷]dec-2-yl[1-(1H-indol-3-ylmethyl)-1-methyl-2-oxo-2-[(2-phenylethyl)amino]ethyl]carbamate,

21. tricyclo[3.3.1.1³,⁷]dec-2-yl[2-[[1-(hydroxymethyl)-2-phenylethyl]amino]-1-(1H-indol-3-ylmethyl)-1-methyl-2-oxoethyl]carbamate,

22. 2-[[3-(1H-indol-3-yl)-2-methyl-1-oxo-2-[[(tricyclo[3.3.1.1³,⁷]dec-2-yloxy)carbonyl]amino]propyl]amino]-3-phenylpropyl butanedioate,

23. 2-[[3-(1H-indol-3-yl)-2-methyl-1-oxo-2-[[(tricyclo[3.3.1.1³,⁷]dec-2-yloxy)carbonyl]amino]propyl]amino]-2-phenylethyl butanedioate,

24. [R-(R*,R*)]-4-[[2-[[3-(1H-indol-3-yl)-2-methyl-1-oxo-2-[[(tricyclo[3.3.1.1³,⁷]dec-2-yloxy)carbonyl]amino]propyl]amino]-2-phenylethyl]amino]-4-oxobutanoic acid,

25. [1S-[1α,2β[S*(S*)],4α]]-4-[[2-[[3-(1H-indol-3-yl)-2-methyl-1-oxo-2-[[[(1,7,7-trimethylbicyclo-2.2.1]hept-2-acid,

26. [R-[R*,S*-(E)]]-4-[[2-[[3-(1H-indol-3-yl)-2-methyl-1-oxo-2-[[(tricyclo[3.3.1.1³,⁷]dec-2-yloxy)carbonyl]amino]propyl]amino]-3-phenylpropyl]amino]-4-oxo-2-butenoic acid,

27. [R-(R*,S*)]-4-[[2-[[3-(1H-indol-3-yl)-2-methyl-1-oxo-2-[[(tricyclo[3.3.1.1³,⁷]dec-2-yloxy)carbonyl]amino]propyl]amino]-3-phenylpropyl]amino]-4-oxobutanoic acid,

28. (R)-tricyclo[3.3.1.1³,⁷]dec-2-yl [1-(1H-indol-3-ylmethyl)-1-methyl-2-[methyl(2-phenylethyl)amino]-2-oxoethylcarbamate,

29. [R-(R*,S*)]-[[2-[[3-(1H-indol-3-yl)-2-methyl-1-oxo-2-[[(tricyclo[3.3.1.1³,⁷]dec-2-yloxy)carbonyl]amino]propyl]amino]-3-phenylpropyl]sulfinyl]acetic acid, ethyl ester,

30. [R-(R*,S*)]-[[2-[[3-(1H-indol-3-yl)-2-methyl-1-oxo-2-[[(tricyclo[3.3.1.1³,⁷]dec-2-yloxy)carbonyl]amino]propyl]amino]-3-phenylpropyl]sulfonyl]acetic acid, ethyl ester,

31. [R-(R*,S*)]-[[2-[[3-(1H-indol-3-yl)-2-methyl-1-oxo-2-[(tricyclo[3.3.1.1³,⁷]dec-2-yloxy)carbonyl]amino]propyl]amino]-3-phenylpropyl)sulfinyl]acetic acid,

32. [R-[R*,R*-(E)]]-4-[[2-[[3-(1H-indol-3-yl)-2-methyl-1-oxo-2-[[(tricyclo[3.3.1.1³,⁷]dec-2-yloxy)]carbonyl]amino]propyl]amino]-1-phenylethyl]amino]-4-oxo-2-butenoic acid,

33. [R-(R*,S*)]-[[2-[[2-[3-(1H-indol-3-yl)-2-methyl-1-oxo-2-[[(tricyclo[3.3.1.1³,⁷]dec-2-yloxy)]carbonyl]amino]propyl]amino]-3-phenylpropyl]thio]acetic acid,

34. [1S-[1α,2β[S*[S*(E)]],4α]]-4-[[2-[[3-(1H-indol-3-yl)-2-methyl-1-oxo-2-[[[(1,7,7-trimethylbicyclo[2.2.1]hept-2-acid, methyl ester, (Bicyclo system is 1S-endo),

35. [1S-[1α,2β[S*[S*(E)]],4α]]-4-[[2-[[3-(1H-indol-3-yl)-2-methyl-1-oxo-2-[[[(1,7,7-trimethylbicyclo[2.2.1]hept-2-acid, (Bicyclo system is 1S-endo),

36. [R-(R*,R*)]-3-[[2-[[3-(1H-indol-3-yl)-2-methyl-1-oxo-3-[[(tricyclo[3.3.1.1³,⁷]dec-2-yloxy)carbonyl]amino]propyl]amino]-1-phenylethyl]amino]-3-oxopropylcarbamic acid,

37. [R-(R*,S*)]-3-(1H-indol-3-ylmethyl)-3-methyl-4,10-dioxo-6-(phenylmethyl)-11-oxo-8-thia-2,5-diazatridecanoic acid, tricyclo[3.3.1.1³,⁷]-dec-2-yl or ester,

38. [R-(R*,S*)]-β-[[3-(1H-indol-3-yl)-2-methyl-1-oxo-2-[[(tricyclo[3.3.1.1³,⁷]dec-2-yloxy)]carbonyl]amino]propyl]amino]benzenebutanoic acid,

39. [R-(R*,S*)]-N-[3-[[3-(1H-indol-3-yl)-2-methyl-1-oxo-2-[[(tricyclo[3.3.1.1³,⁷]dec-2-yloxy)carbonyl]amino]propyl]amino]-4-phenylbutyl]glycine,

40. [R-[R*,S*-(E)]]-4-[[2-[[3-(1H-indol-3-yl)-2-methyl-2-[[(bicyclo[3.3.1]non-9-yloxy)carbonyl]amino]ethyl]carbamate,

41. mono [R-(R*,R*)]-2-[[3-(1H-indol-3-yl)-2-methyl-1-oxo-2-[[(tricyclo[3.3.1.1³,⁷]dec-2-yloxy)carb butanedioate,

42. 3-[[3-[[3-(1H-indol-3-yl)-2-methyl-1-oxo-2-[[(tricyclo[3.3.1.1³,⁷]dec-2-yloxy)]carbonyl]amino]propyl]amino]-1-oxo-2-phenylpropyl]amino]propanoic acid (TRP is R, other center is RS), methyl-2-[[[(2-methyl-1-cyclohexyl)oxy]carbonyl]ami acid, (-)-Isomer, methyl-2-[[[(2-methyl-1-cyclohexyl)oxy]carbonyl]

amino]-1-oxopropyl]amino]-3-phenylpropyl]amino]-4-oxobutanoic acid, (−)-Isomer,

45. [1R-[1α[R*(S*)],2β]]-4-[[2-[[3-(1H-indol-3-yl)-2-methyl-2-[[[(2-methyl-1-cyclohexyl)oxy]carbonyl acid, (−)-Isomer,

46. [1R-[1α[R*(S*)],2β]]-4-[[2-[[3-(1H-indol-3-yl)-2-methyl-2-[[[(2-methyl-1-cyclohexyl)oxy]carb acid, (−)-Isomer,

47. 2-methylcyclohexyl-[1R-[1α[R*(S*)]],2β]-[2-[[1-(hydroxymethyl)-2-phenylethyl]amino]-1-(1H-indol-3-ylmethyl)-1-methyl-2-oxoethyl]carbamate,

48. [R-[R*,S*-(E,E)]]-6-[[3-(1H-indol-3-yl)-2-methyl-1-oxo-2-[[(tricyclo[3.3.1.1$^{3,7}$]dec-2-yloxy)carbonyl]amino] propyl]amino]-7-phenyl-2,4-heptadienoic acid,

49. [R-(R*,R*)]-[2-[[2-[[1,4-dioxo-4-(1H-tetrazol-5-ylamino)butyl]amino]-2-phenyl-ethyl]amino]-1-(1H-indol-3-ylmethyl)-1-methyl-2-oxoethyl]carbamic acid,

50. tricyclo[3.3.1.1$^{3,7}$]dec-2-yl-[S-[R*,S*-(E)]]-12-(1H-indol-3-ylmethyl)-12-methyl-3,11-dioxo-9-(phenylmethyl)-2-oxa-7,10,13-triazatetradec-4-en-14-oate,

51. [R-(R*,S*)]-3-[[2-[[3-(1H-indol-3-yl)-2-methyl-1-oxo-2-[[(tricyclo[3.3.1.1$^{3,7}$]dec-2-yloxy)carbonyl)amino] propyl]amino]-3-phenylpropyl]amino]-3-oxopropanoic acid,

52. ethyl [R-(R*,S*)]-[[2-[[2-[3-(1H-indol-3-yl)-2-methyl-1-oxo-2-[[(tricyclo[3.3.1.1$^{3,7}$]dec-2-yloxy)carbonyl] amino]propyl]amino]-3-phenylpropyl]thio]acetate,

53. [R-(R*,S*)]-β-[[3-(1H-indol-3-yl)-2-methyl-1-oxo-2-[[tricyclo[3.3.1.1$^{3,7}$]dec-2-yloxy)carbonyl]amino]propyl] amino]-4-iodo-benzenebutanoic acid,

54. [R-(R*,R*)]-[2-[[3-(1H-indol-3-yl)-2-methyl-1-oxo-2-[[(1 (tricyclo[[(3.3.1.1$^{3,7}$]dec-2-yloxy)carbonyl]amino] propyl]amino]-1-phenylethoxy]acetic acid,

55. [[3-[[3-(1H-indol-3-yl)-2-methyl-1-oxo-3-[[tricyclo (3.3.1.1$^{3,7}$]dec-2-yloxy)carbonyl]amino]propyl]amino]-1-oxo-2-phenylpropyl]amino]acetic acid (TRP center is R, other center is RS),

56. (R)-[[[2-[[3-(1H-indol-3-yl)-1-oxo-2-methyl-2-[[(tricyclo[3.3.1.1$^{3,7}$]dec-2-yloxy)carbonyl]-amino] propyl]amino]-1-phenylethylidene]amino]oxy]acetic acid,

57. [R-(R*,S*)]-β-[[3-(1H-indol-3-yl)-2-methyl-1-oxo-2-[[(tricyclo[3.3.1.1$^{3,7}$]dec-2-yloxy)carbonyl]amino] propyl]amino]benzenebutanoic acid,

58. [R-(R*,S*)]-N-[3-[[3-(1H-indol-3-yl)-2-methyl-1-oxo-2-[[(tricyclo[3.3.1.1$^{3,7}$]dec-2-yloxy)carbonyl]propyl] amino]-4-phenylbutyl]glycine,

59. 2-[[[2-[[3-(1H-indol-3-yl)-2-methyl-1-oxo-2-[[(tricyclo[3.3.1.1$^{3,7}$]dec-2-yloxy)carbonyl]amino] propyl]amino]-1-phenylethyl]amino]carbonyl] cyclopropanecarboxylic acid (cyclopropane ring is trans-(±), other centers are R),

60. carbamic acid, [1-(1H-indol-3-ylmethyl)-1-methyl-2-oxo-2-[[2-[[1-oxo-3-(1H-tetrazol-5-yl)propyl]amino]-2-phenylethyl]amino]ethyl]-, tricyclo[3.3.1.1$^{3,7}$]dec-2-yl ester, [R, (R*,S*)]-,

61. benzeneheptanoic acid, α-[[3-(1H-indol-3-yl)-2-methyl-1-oxo-2-[[(tricyclo[3.3.1.1$^{3,7}$]dec-2-yloxy) carbonyl]amino]propyl]amino]-,[R-(R*,S*)]-,

62. methyl-(±)-β-[[[(2-phenylethyl)amino]carbonyl]-1β-[[(tricyclo[3.3.1.1$^{3,7}$]dec-2-yloxy)carbonyl]amino]-1H-indole-3-butanoate,

63. [R-(R*,S*)]-4-[[2-(1H-indol-3-yl)-2-methyl-1-oxo-2-[[tricyclo[3.3.1.1$^{3,7}$]dec-2-yloxy-carbonyl]amino]propyl] amino]-3-phenylpropyl]-amino]-4-oxo-2-butenoic acid,

64. bicyclo[2.2.1]heptane-2-acetic acid, 3-[[[[2-[[1-(hydroxymethyl)-2-phenylethyl]amino]-1-(1H-indol-3-ylmethyl)-1-methyl-2-oxoethyl]-amino]carbonyl]oxy]-4,7,7-trimethyl-, [1R-[1α,2β,3α[R*(S*)],4α]]-,

65. butanoic acid, 4-[[2-[[3-(1H-indol-3-yl)-2-methyl-2-[[[(2-methyl-1-cyclohexyl)oxy]carbonyl]amino]-1-oxopropyl]amino]-1-phenylethyl]amino]-4-oxo-2-butenoic oxopropyl]amino]-1-phenylethyl]amino]-4-oxo-[1R-1α[R*(R*)]2β]]-((−)-isomer),

66. butanoic acid, 4-[[2-[[3-(1H-indol-3-yl)-2-methyl-2-[[[(2-methyl-1-cyclohexyl)oxy]-carbonyl]amino]-1-oxopropyl]amino]-1-phenylethyl]amino]-4-oxo-, [1R-[1α[R*(R*)],2β]]-((−)-isomer),

67. butanoic acid, 4-[[2-[[3-(1H-indol-3-yl)-2-methyl-2-[[[(2-methyl-1-cyclohexyl)oxy]carbonyl]-amino]-1-oxopropyl]amino]-3-phenylpropyl]amino]-4-oxo-[1R-[1α[R*(S*)],2β]]-((−)-isomer), and

68. 2-butenoic acid, 4-[[2-[[3-(1H-indol-3-yl)-2-methyl-2-[[[(2-methyl-1-cyclohexyl)oxy]carbonyl]-amino]-1-oxopropyl]amino]-3-phenylpropyl]amino]-4-oxo-[1R[1α[R*(S*)],2β]]-((−)-isomer).

69. [[3-[[3-(1H-indol-3-yl)-2-methyl-1-oxo-[[tricyclo[3.3.1.1$^{3,7}$]dec-2-yloxy)carbonyl]amino]propyl]amino]-1-oxo-2-phenylpropyl]amino]acetic acid,

70. [R-(R*,R*)]-[2-[[3-(1H-indol-3-yl)-2-methyl-1-oxo-2-[[(tricyclo[3.3.1.1$^{3,7}$]dec-2-yloxy)carbonyl]amino] propyl]amino]-1-phenylethoxy]-acetic acid,

71. [1R-[1α,2β[R*(R*)]]]-2-[[[2-[[3-(1H-indol-3-yl)-2-methyl-1-oxo-2-[[(tricyclo[3.3.1.1$^{3,7}$]dec-2-yloxy) carbonyl]amino]propyl]amino]-1-phenylethyl]amino] carbonyl]cyclopropane carboxylic acid,

72. [1S-[1α,2β[S*(S*)]]]-2-[[[2-[[3-(1H-indol-3-yl)-2-methyl-1-oxo-2-[[(tricyclo[3.3.1.1$^{3,7}$]dec-2-yloxy) carbonyl]amino]propyl]amino]-1-phenylethyl]amino] carbonyl]cyclopropane carboxylic acid,

73. [R-R*,R*)]-3-[2-[[3-(1H-indol-3-yl)-2-methyl-1-oxo-2-[[(tricyclo[3.3.1.1$^{3,7}$]dec-2-yloxy)carbonyl]amino] propyl]amino]-1-phenylethoxy]propanoic acid,

74. [R-(R*,R*)]-mono 2-[[3-(1H-indol-3-yl)-2-methyl-1-oxo-2-[[(tricyclo[3.3.1.1$^{3,7}$]dec-2-yloxy)carbonyl] amino]-3-1-phenylethyl butanedioic acid,

75. 3-[[3-[[3-(1H-indol-3-yl)-2-methyl-1-oxo-2-[[(tricyclo[3.3.1.1$^{3,7}$]dec-2-yloxy)carbonyl]-amino]propyl]amino]-1-oxo-2-phenylpropyl]-amino]propanoic acid,

76. [R-(R*,S*)]-β-[[3-(1H-indol-3-yl)-2-methyl-1-oxo-2-[[(tricyclo[3.3.1.1$^{3,7}$]dec-2-yloxy)-carbonyl]amino] propyl]amino]-4-iodobenzenebutanoic acid,

77. [1R-[1α[R*(S*)],2β]]-4-[[2-[[3-(1H-indol-3-yl)-2-methyl-2-[[[(2-methyl-1-cyclohexyl)oxy]-carbonyl] amino]-1-oxopropyl]amino]-3-phenylpropyl]amino]-4-oxo-2-butenoic acid,

78. [1R-[1α[R*(S*)],2β]]-4-[[2-[[3-(1H-indol-3-yl)-2-methyl-2-[[[(2-methyl-1-cyclohexyl)-oxy]carbonyl] amino]-1-oxopropyl]amino]-3-phenylpropyl]amino]-4-oxobutanoic acid, ((−)-isomer),

79. [1R-[1α[R*(R*)],2β]]-4-[[2-[[3-(1H-indol-3-yl)-2-methyl-2-[[[(2-methyl-1-cyclohexyl)-oxy]carbonyl] amino]-1-oxopropyl]amino]-1-phenylethyl]amino]-4-oxo-2-butenoic acid,

80. 1R-[1α[R*(R*)],2β]]-4-[[2-[[3-(1H-indol-3-yl)-2-methyl-2-[[[(2-methyl-1-cyclohexyl)oxy]carbonyl] amino]-1-oxopropyl]amino]-1-phenylethyl]amino]-4-oxobutanoic acid, ((−)-isomer),

81. [R-(R*,S*)]-lg/-[[3-(1H-indol-3-yl)-2-methyl-1-oxo-2-[[(tricyclo[3.3.1.1$^{3,7}$]dec-2-yloxy)carbonyl]amino] propyl]amino]benzeneheptanoic acid,

82. 2-[[[2-[[3-(1H-indol-3-yl)-2-methyl-1-oxo-2-[[(tricyclo[3.3.1.1$^{3,7}$]dec-2-yloxy)carbonyl]-amino] propyl]amino]-1-phenylethyl]amino]-carbonyl] cyclopropanecarboxylic acid (cyclopropyl ring is trans-(±), other centers are R),

83. 2-methylcyclohexyl [1R-[1α[R*(S*)]],2β]-[[1-(hydroxymethyl)-2-phenylethyl]amino]-1-(1H-indol-3-ylmethyl)-1-methyl-2-oxoethyl]carbamate,

84. [R-[R*,S*-(E<E)[[-6-[[3-(1H-indol-3-yl)-2-methyl-1-oxo-2-[[(tricyclo[3.3.1.1$^{3,7}$]dec-2-yloxy)carbonyl]amino]propyl]amino]-7-phenyl-2,4-heptadienoic acid,

85. tricyclo[3.3.1.1$^{3,7}$]dec-2-yl [2-[[1-(hydroxymethyl)-2-hydroxy-2-phenylethyl]amino]-1-(1H-indol-3-ylmethyl)-1-methylethyl]carbamate,

86. tricyclo[3.3.1.1$^{3,7}$]dec-2-yl [R-(R*,R*)]-[1-(1H-indol-3-ylmethyl)-1-methyl-2-oxo-2-[[2-[[1-oxo-3-(1H-tetrazol-5-yl)propyl]amino]-2-phenylethyl]amino]ethyl]carbamate,

87. [R-(R*,S*)]-2-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]sulfinyl]acetic acid,

88. [R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]sulfonyl]acetic acid,

89. ethyl [R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]sulfonyl]acetate,

90. 2-chlorocyclohexyl [2-[[1-(hydroxymethyl)-2-phenylethyl]amino]-1-(1H-indol-3-ylmethyl)-1-methyl-2-oxoethyl]carbamate.

91. [R-[R*,R*(E)]]-4-[[2-[[3-(1H-indol-3-yl)-2-methyl-1-oxo-2-[[(tricyclo[3.3.1.1$^{3,7}$]dec-2-ylamino)carbonyl]amino]propyl]amino]-1-phenylethyl]amino]-4-oxo-2-butenoic acid,

92. [R-(R*,R*)]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxobutanoic acid,

93. [R-(R*,S*)]-mono[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]butanedioate,

94. tricyclo[3.3.1.1$^{3,7}$]dec-2-yl [R-(R*,S*)-[2-[[1-(hydroxymethyl)-2-phenylethyl]amino]-1-(1H-indol-3-ylmethyl)-1-methyl-2-oxoethyl]carbamate,

95. [1S-[1α,2β[S*[S(E)]],4α]]-4-[[2-[[3-(1H-indol-3-yl)-2-methyl-1-oxo-2-[[[(1,7,7-trimethylbicyclo[2.2.1]hept-2-yl)oxy]-carbonyl]amino]propyl]amino]-1-phenylethyl]-amino]-4-oxo-2-butenoic acid,

96. [1S-[1α,2β[S*(S*)],4α]]-4-[[2-[[3-(1H-indol-3-yl)-2-methyl-1-oxo-[[[(1,7,7-trimethylbicyclo[2.2.1]hept-2-yl)oxy]carbonyl]-amino]propyl]amino]-1-phenylethyl]amino]-4-oxo-2-butenoic acid, (bicyclo system is 1S-endo),

97. [R-[R*,S*-(E)]]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-4-oxo-2-butenoic acid,

98. N-[2-methyl-N-[(tricyclo[3.3.1.1$^{3,7}$]dec-2-yloxy)carbonyl]-D-tryptophyl]-L-phenylalanyl-glycine,

99. [R-(R*,S*)[-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-4-oxobutanoic acid,

100. [R-(R*,R*)]-2-[[2-[[1,4-dioxo-4-(1H-tetrazol-5-ylamino)butyl]amino]-2-phenylethyl]amino]-1-(1H-indol-3-ylmethyl)-1-methyl-2-oxoethyl]carbamic acid,

101. [R-(R*,R*)]-3-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-3-oxopropanoic acid,

102. [R-(R*,S*)]-3-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-3-oxopropanoic acid,

103. [R-[R*,S*-(E)]]-4-[[2-[[3-(1H-indol-3-yl)-2-methyl-2-[[(bicyclo[3.3.1]non-9-yloxy)carbonyl]-amino]-1-oxopropyl]amino]-3-phenylpropyl]amino]-4-oxo-2-butenoic acid,

104. [R-(R*,S*)]-5-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-5-oxopentanoic acid,

105. ethyl [R-(R*,S*)]-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]sulfinyl]acetate,

106. [R-[R*,R*-(E)]]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxo-2-butenoic acid,

107. [R-(R*,S*)]-N-[3-[[3-(1H-indol-3-yl)-2-methyl-1-oxo-2-[[(tricyclo[3.3.1.1$^{3,7}$]dec-2-yloxy)carbonyl]amino]propyl]amino]-1-oxo-4-phenylbutyl]-β-alanine,

108. N-[N-[α-methyl-N-[(tricyclo[3.3.1.1$^{3,7}$]dec-2-yloxy)carbonyl]-D-tryotophyl]-L-phenylalanyl]-L-alanine,

109. [R-R*,S*)]-3-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]thio]propanoic acid,

110. [R-(R*,S*)]-[[2-[[2-[3-(1H-indol-3-yl)-2-methyl-1-oxo-2-[[(tricyclo[3.3.1.1$^{3,7}$]dec-2-yloxy)carbonyl]amino]propyl]amion]-3-phenylpropyl]thio]acetic acid,

111. [R-(R*,S*)]-β-[[3-(1H-indol-3-yl)-2-methyl-1-oxo-2-[[tricyclo[3.3.1.1$^{3,7}$]dec-2-yloxy)carbonyl]amino]propyl]amino]benzenebutanoic acid,

112. tricyclo[3.3.1.1$^{3,7}$]dec-2-yl [R-(R*,S*)]-3-(1H-indol-3-ylmethyl)-3-methyl-4,10-dioxo-6-(phenylmethyl)-11-oxa-8-thia-2,5-diazatridecanoic acid,

113. [2-[[2-hydroxy-1-(hydroxymethyl)-2-phenylethyl]amino]-1-(hydroxymethyl)-1-(1H-indol-3-yl-methyl)-2-oxoethyl]-, tricyclo[3.3.1.1$^{3,7}$]dec-2-yl ester,

114. N-[α-methyl-N-[(tricyclo[3.3.1.1$^{3,7}$]dec-2-yloxy)carbonyl]-L-tryptophyl]-D-3-(phenylmethyl)-β-alanine,

115. (1R-trans)-N-[α-methyl-N-[[(2-methylcyclohexyl)oxy]carbonyl]-L-tryptophyl]-D-3-(phenylmethyl)((1R,2R)-N-[[(2-methylcyclohexyl)oxy]carbonyl])(α/-Me)LTrp-(D-3-Bzl)bAla-β-alanine ((−)-isomer), and

116. (1S-trans)-N-[(α-methyl-N-[[(2-methylcyclohexyl)oxy]carbonyl]-D-tryptophyl]-L-3-(phenylmethyl)-β-alanine.

3. A method according to claim 1 wherein the compound administered is CI-988 or a pharmaceutically acceptable salt thereof.

4. A method according to claim 1 wherein an individual dose of 5 mg to 50 mg parenterally or of 5 mg to 600 mg enterally of the compound or a pharmaceutically acceptable salt thereof is administered.

* * * * *